United States Patent
Roghanizad

(10) Patent No.: US 12,313,477 B2
(45) Date of Patent: *May 27, 2025

(54) APPARATUS, SYSTEMS, AND METHODS FOR NON-INVASIVE THERMAL INTERROGATION

(71) Applicant: THERMASENSE CORP., Blacksburg, VA (US)

(72) Inventor: Ali R. Roghanizad, Blacksburg, VA (US)

(73) Assignee: THERMASENSE CORP., Blacksburg, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/132,508

(22) Filed: Apr. 10, 2023

(65) Prior Publication Data

US 2023/0251144 A1    Aug. 10, 2023

Related U.S. Application Data

(63) Continuation of application No. 17/624,207, filed as application No. PCT/US2020/040266 on Jun. 30, 2020, now Pat. No. 11,686,626.

(Continued)

(51) Int. Cl.
*G01K 7/42* (2006.01)
*G01K 13/02* (2021.01)
(Continued)

(52) U.S. Cl.
CPC .............. *G01K 7/427* (2013.01); *G01K 13/02* (2013.01); *G01N 25/18* (2013.01); *G01N 33/4833* (2013.01)

(58) Field of Classification Search
CPC ........ G01K 7/427; G01K 13/02; G01N 25/18; G01N 33/4833
See application file for complete search history.

(56) References Cited

U.S. PATENT DOCUMENTS 4,415,279 A    11/1983   Beuse et al.
4,779,994 A    10/1988   Diller et al.
(Continued)

FOREIGN PATENT DOCUMENTS

DE    102017116505    1/2019
JP    S55149025       11/1980
(Continued)

OTHER PUBLICATIONS

Translation of JP2015117921A.*
(Continued)

*Primary Examiner* — Mirellys Jagan
(74) *Attorney, Agent, or Firm* — NIXON & VANDERHYE P.C.

(57) ABSTRACT

Various non-invasive sensors are adapted to be placed on a surface of an object having a volume with an internal region. The internal region of the object has internal properties indicated by corresponding internal parameters and an internal temperature distribution that is a function of the internal parameters and surface thermal signals. Each non-invasive sensor includes a heat flux sensor having one or more heat flux sensor output terminals to provide a measured heat transfer signal for the surface of the object, and a temperature sensor having one or more temperature sensor output terminals to provide a measured temperature signal for the surface of the object. Systems including one or more of the sensors perform non-invasive sensing of the object including accurate and rapid determination of an internal temperature distribution of the internal region of the object as well as one or more other internal properties of the object.

60 Claims, 40 Drawing Sheets

Related U.S. Application Data

(60) Provisional application No. 62/869,208, filed on Jul. 1, 2019.

(51) Int. Cl.
   *G01N 25/18* (2006.01)
   *G01N 33/483* (2006.01)

(56) References Cited

U.S. PATENT DOCUMENTS

| | | | |
|---|---|---|---|
| 6,278,051 B1 * | 8/2001 | Peabody | H10N 10/00 374/30 |
| 6,280,397 B1 | 8/2001 | Yarden et al. | |
| 6,558,036 B2 | 5/2003 | Gysling et al. | |
| 7,299,090 B2 | 11/2007 | Koch | |
| 8,136,983 B2 | 3/2012 | Razzaghi | |
| 8,449,181 B2 | 5/2013 | Rud et al. | |
| 8,716,629 B2 | 5/2014 | Klewer et al. | |
| 8,801,272 B2 | 8/2014 | Bieberich et al. | |
| 8,945,020 B2 | 2/2015 | Cheung et al. | |
| 9,101,271 B2 | 8/2015 | Sattler | |
| 9,360,377 B2 | 6/2016 | Converse | |
| 9,970,828 B2 | 5/2018 | Ude | |
| 10,190,968 B2 | 1/2019 | Hedtke et al. | |
| 10,234,338 B2 | 3/2019 | Rieder et al. | |
| 10,317,295 B2 | 6/2019 | Rud et al. | |
| 10,386,246 B2 | 8/2019 | Disselnkoetter et al. | |
| 10,393,598 B1 | 8/2019 | Cherry et al. | |
| 10,405,755 B2 | 9/2019 | Shrubsole et al. | |
| 10,670,546 B2 | 6/2020 | Rud et al. | |
| 10,976,204 B2 | 4/2021 | Rud | |
| 11,051,700 B2 | 7/2021 | Koch et al. | |
| 11,067,520 B2 | 7/2021 | Rud et al. | |
| 11,073,429 B2 | 7/2021 | Rud | |
| 11,085,589 B2 | 8/2021 | Rud et al. | |
| 11,141,076 B1 | 10/2021 | Diller et al. | |
| 11,320,316 B2 | 5/2022 | Rud et al. | |
| 11,630,072 B2 | 4/2023 | Rud et al. | |
| 2002/0150143 A1 | 10/2002 | Tokita et al. | |
| 2002/0191675 A1 | 12/2002 | Tokita et al. | |
| 2006/0056487 A1 | 3/2006 | Kuroda et al. | |
| 2010/0088060 A1 | 4/2010 | Padiy | |
| 2010/0113894 A1 | 5/2010 | Padiy | |
| 2011/0317737 A1 | 12/2011 | Klewer et al. | |
| 2012/0109571 A1 | 5/2012 | Shimizu | |
| 2012/0114013 A1 | 5/2012 | Tsuchida | |
| 2012/0128024 A1 | 5/2012 | Tsuchida et al. | |
| 2013/0317388 A1 | 11/2013 | Bieberich et al. | |
| 2014/0278201 A1 | 9/2014 | Shimizu | |
| 2015/0204733 A1 * | 7/2015 | Newell | G01K 7/16 374/141 |
| 2015/0257652 A1 | 9/2015 | Van Duren | |
| 2016/0047697 A1 | 2/2016 | Decker et al. | |
| 2016/0069752 A1 | 3/2016 | Shimizu | |
| 2016/0081629 A1 | 3/2016 | Rostalski et al. | |
| 2016/0313193 A1 | 10/2016 | Nakagawa et al. | |
| 2017/0049397 A1 | 2/2017 | Sun et al. | |
| 2017/0074730 A1 * | 3/2017 | Rieder | G01K 7/427 |
| 2017/0100042 A1 | 4/2017 | Shrubsole et al. | |
| 2017/0184523 A1 | 6/2017 | Ikeda et al. | |
| 2017/0212065 A1 * | 7/2017 | Rud | G01K 7/427 |
| 2018/0038722 A1 | 2/2018 | Ozaki et al. | |
| 2018/0049646 A1 | 2/2018 | Ellis et al. | |
| 2019/0175024 A1 | 6/2019 | Lan et al. | |
| 2020/0037884 A1 | 2/2020 | Ishida | |
| 2020/0085310 A1 | 3/2020 | Zahner et al. | |
| 2020/0103293 A1 | 4/2020 | Rud et al. | |
| 2020/0225096 A1 | 7/2020 | Ude et al. | |
| 2020/0390336 A1 | 12/2020 | Mensch et al. | |
| 2020/0408580 A1 | 12/2020 | Gebhardt et al. | |
| 2021/0108917 A1 * | 4/2021 | Hazuku | G01B 21/085 |
| 2021/0181032 A1 | 6/2021 | Gebhardt et al. | |
| 2021/0244285 A1 | 8/2021 | Mansholt et al. | |
| 2022/0260432 A1 * | 8/2022 | Leibig | G01K 1/18 |

FOREIGN PATENT DOCUMENTS

| | | |
|---|---|---|
| JP | 2002-372464 | 12/2002 |
| JP | 2010-8429 | 1/2010 |
| JP | 2015117921 A * | 6/2015 |
| JP | 2015197313 A * | 11/2015 |
| JP | 2016-161415 | 9/2016 |
| JP | 2017-120224 | 7/2017 |
| WO | 2015/092627 | 6/2015 |
| WO | 2016202971 | 12/2016 |
| WO | 2018/180800 | 10/2018 |

OTHER PUBLICATIONS

Translation of JP2015197313A.*
U.S. Appl. No. 17/624,207, filed Dec. 30, 2021, Roghanizad.
Office Action dated Dec. 20, 2022 for U.S. Appl. No. 17/624,207, 21 pages.
International Search Report for PCT/US2020/040266 dated Sep. 25, 2020, 3 pages.
Written Opinion of the ISA for PCT/US2020/040266 dated Sep. 25, 2020, 18 pages.
International Preliminary Report on Patentability for PCT/US2020/040266 mailed Jul. 2, 2021, 37 pages.
Office Action for CA Application No. 3,142,176 dated Jan. 14, 2022, 4 pages.
Extended European Search Report for EP Application 20835336.7 dated Jul. 21, 2022.
Office Action for AU Application No. 2020300996 dated Jan. 18, 2022, 3 pages.
Notice of Acceptance for AU Application No. 2020300996 dated May 6, 2022, 4 pages.
J. Okajima et al, "Estimation of Blood Perfusion Rate and its Temperature Dependency in Human Abdominal Area Under Heating Condition" Proceedings of the 15th International Heat Transfer Conference, IHTC-15, Aug. 10-15, 2014, pp. 1065-1075.
A. V. Mudaliar et al, "A Phantom Tissue System for the Calibration of Perfusion Measurements" Journal of Biomechanical Engineering, vol. 130, Oct. 2008, 10 pages.
F.S. Castellana et al., "Steady-State Analysis and Evaluation of a New Thermal Sensor for Surface Measurements of Tissue Perfusion" Annals of Biomedical Engineering, vol. 11, 1983, pp. 101-115.
H.J. Li et al, "Measurement of Blood Perfusion Using the Temperature Response to Constant Surface Flux Heating" International Journal of Thermophysics, vol. 23, No. 6, Nov. 2002, pp. 1631-1644.
A. Alkhwaji et al, "New Mathematical Model to Estimate Tissue Blood Perfusion, Thermal Contact Resistance and Core Temperature" Journal of Biomechanical Engineering, vol. 134, Aug. 2012, 8 pages.
A. Al-Khwaji et al, "Modeling and Estimating Simulated Burn Depth Using the Perfusion and Thermal Resistance Probe" Journal of Medical Devices, vol. 7, Sep. 2013, 9 pages.
T. O'Brien et al, "The Development of a Thin-Filmed Noninvasive Tissue Perfusion Sensor to Quantify Capillary Pressure Occlusion of Explanted Organs" IEEE Transactions on Biomedical Engineering, vol. 64, No. 7, Jul. 2017, pp. 1631-1637.
Office Action for JP Application No. 2021-576264 mailed Sep. 5, 2022 and English translation, 10 pages.
Office Action for JP Application No. 2021-576264 mailed Mar. 3, 2023 and English translation, 16 pages.
Office Action for EP Application No. 20835336.7 dated Jul. 6, 2023, 5 pages.
Office Action for KR Application No. 10-2021-7043288 dated Jul. 24, 2023.
Office Action for IN Application No. 202217003963 dated Sep. 6, 2023, 6 pages.
Office Action for AU Application No. 2022218630 dated Sep. 30, 2023, 4 pages.
Office Action for SG Application No. 11202113927Y issued Oct. 18, 2023, 9 pages.

(56) References Cited

OTHER PUBLICATIONS

Notice of Allowance for KR Application No. 10-2021-7043288 issued Oct. 23, 2023 and English translation, 5 pages.
Office Action for JP Application No. 2021-576264 issued Nov. 6, 2023 and English translation, 11 pages.
E.P. Scott et al, "A Methodology for the Noninvasive Estimation of Thermal Properties" Heat Transfer 1994, Proceedings of The Tenth International Heat Transfer Conference, vol. 2, Ed. G. F. Hewitt, Taylor and Francis, N. Y., 1994, pp. 291-296.
K.I. Baker et al., "Unsteady Surface Heat Flux and Temperature Measurements" ASME Paper No. 93-HT-33, ASME National Heat Transfer Conference, Aug. 8-11, 1993, 9 pages.
T. Loulou et al, "An inverse heat conduction problem with heat flux measurements" International Journal for Numerical Methods in Engineering, 2006, 67 (11), pp. 1587-1616.
P.L. Ricketts et al, "Non-invasive blood perfusion measurements using a combined temperature and heat flux surface probe" International Journal of Heat and Mass Transfer, vol. 51, 2008, pp. 5740-5748.
E.P. Scott et al, "Development of methodologies for the estimation of blood perfusion using a minimally invasive thermal probe" Meas. Sci. Technol., vol. 9, 1998, pp. 888-897.
T.B. O'Reilly et al, "Development of Noninvasive Blood Perfusion Probe" Advances in Heat and Mass Transfer in Biotechnology, HTD-vol. 337/BED-vol. 34, ASME 1996, pp. 67-73.
A. Al-khwaji et al, "Monitoring and Quantifying Burn Wounds on Pig Skin using Thermal Measurements" The International Journal of Engineering and Information Technology (IJEIT), vol. 3, No. 1, Dec. 2016, pp. 5-12.
P.L. Ricketts et al, "Noninvasive Blood Perfusion Measurement on the Liver of an Anesthetized Rat" Proceedings of the ASME 2007 Summer Bioengineering Conference (SBC2007), Jun. 20-24, 2007, pp. 1-2.
A. Ballmer et al, "Perfusion Measurements using a Non-Invasive Thermal Probe in a Phantom Test Stand" Proceedings of IMECE'03, 2003 ASME International Mechanical Engineering Congress, Nov. 15-21, 2003, pp. 1-2.
A.V. Mudaliar et al, "Noninvasive Blood Perfusion Measurements of an Isolated Rat Liver and an Anesthetized Rat Kidney" Journal of Biomechanical Engineering, vol. 130, ASME, Dec. 2008, 8 pages.
P.S. Robinson et al, "Testing of a Noninvasive Probe for Measurement of Blood Perfusion" Journal of Medical Devices, vol. 2, ASME, Mar. 2008, 5 pages.
A.V. Cardinali et al, "Validation of a Noninvasive Thermal Perfusion System Using a Canine Medial Saphenous Fasciocutaneous Free Tissue Flap Model" Proceedings of IMECE2002, ASME International Mechanical Engineering Congress & Exposition, Nov. 17-22, 2002, pp. 1-8.
Mitchner, M.D., 1991, "Measurements of Thermal Properties and Blood Perfusion Using the Heat Flux Microsensor", Master of Science in Mechanical Engineering Thesis, Virginia Polytechnic Institute and State University, Blacksburg, VA., 143 pages.
P.S. Robinson et al., "Validation of Methodologies for the Estimation of Blood Perfusion Using a Minimally Invasive Probe" Advances in Heat and Mass Transfer in Biotechnology—1998, HTD-vol. 362/BED-vol. 40, ASME 1998, pp. 109-115.
Mudaliar, A.V., 2007, "Development of a Phantom Tissue for Blood Perfusion Measurements and Noninvasive Blood Perfusion Estimation in Living Tissue", PhD Dissertation. Virginia Polytechnic Institute and State University, Blacksburg, VA., 175 pages.
Office Action for EP Application No. 20835336.7 dated Jul. 9, 2024, 29 pages.
Office Action for SG Application No. 11202113927Y dated Sep. 30, 2024, 9 pages.
Office Action for PH Application No. 1-2021-553176 mailed Jan. 28, 2025, 8 pages.
Office Action for EP Application No. 20835336.7 issued Feb. 24, 2025, 7 pages.
Office Action for BR Application No. BR1120210243674 issued Mar. 18, 2025, 8 pages.

* cited by examiner

APPARATUS, SYSTEMS, AND METHODS FOR NON-INVASIVE THERMAL INTERROGATION

CROSS-REFERENCE TO RELATED APPLICATIONS

This application is a continuation of U.S. application Ser. No. 17/624,207, filed Dec. 30, 2021, which is the U.S. national phase of International Application No. PCT/US2020/040266 filed Jun. 30, 2020 which designated the U.S. and claims priority to U.S. Provisional Patent Application Ser. No. 62/869,208 filed Jul. 1, 2019, the entire contents of each of which are hereby incorporated by reference.

BACKGROUND

Temperature sensors and other thermal sensing systems are important in many different technological fields and applications. Of particular importance are temperature sensors and other thermal sensing systems that are non-invasive. The technology in this application is directed to non-invasive thermal interrogation apparatus, systems, and methods that provide improved reliability, accuracy, cost, complexity, size, ease of manufacture, ease of use, computational time, processing power required, response time, and applicability across different industries.

Non-Invasive Thermal Interrogation (NITI) provides non-destructive testing and monitoring using thermal sensing. Non-Invasive Thermal Interrogation (NITI) is conducted using simultaneous combinations of surface temperature signals and surface heat transfer (e.g., heat flux) signals. When measured simultaneously on an object or system surface, the surface temperature and surface heat flux signals may be used to non-invasively determine internal parameters (e.g., thermal conductivity, density, heat capacity, convection coefficient, steady-state thermal resistance, etc.) and internal temperature distribution (e.g., an internal temperature profile) of the internal region of the object or system. The internal temperature distribution of the object or system is typically a function of the internal parameters. Depending on the object or system undergoing NITI and/or NITI application, the internal parameters may vary. The internal parameters and internal temperature distribution are defined as internal properties of the object or system.

Because NITI allows for the non-destructive testing and monitoring of an object or system whenever thermal signals are present, NITI may be utilized in many diverse applications. In cases where sufficient thermal signals are not present, they can be generated at the object or system surface.

SUMMARY

At least some examples provide a system for non-invasive sensing of an object having a volume with a surface and an internal region. The system comprises a non-invasive sensor including: a heat flux sensor having one or more heat flux sensor output terminals, and a temperature sensor having one or more temperature sensor output terminals. The non-invasive sensor may be placed on or near the surface of the object. The internal region of the object has internal properties indicated by corresponding internal parameters and an internal temperature distribution. Control circuitry, coupled to the one or more heat flux sensor output terminals and the one or more temperature sensor output terminals, is adapted to: receive a measured temperature signal from the temperature sensor at one or more specified times; receive a measured heat flux signal from the heat flux sensor at the one or more specified times; determine a measure of heat transfer leaving or entering the object at the surface based on the measured heat flux signal at the one or more specified times; determine a value for each of the internal parameters at the one or more specified times; determine an internal temperature distribution of the internal region of the object at the one or more specified times based on the measured temperature signal, the measured heat flux signal, and the values of the internal parameters; and generate information indicating the internal temperature distribution of the internal region of the object at the one or more specified times.

At least some examples provide a system for non-invasive sensing of an object having a volume with a surface and an internal region. The system includes a non-invasive sensor including: a heat flux sensor having one or more heat flux sensor output terminals, and a temperature sensor having one or more temperature sensor output terminals. The non-invasive sensor is adapted to be placed on or near the surface of the object, and the internal region of the object has internal properties indicated by corresponding internal parameters and an internal temperature distribution. Control circuitry, coupled to the one or more heat flux sensor output terminals and the one or more temperature sensor output terminals, is adapted to: receive a measured temperature signal from the temperature sensor at one or more specified times; receive a measured heat flux signal from the heat flux sensor at the one or more specified times; determine estimated values for one or more of the internal parameters at the one or more specified times based on the measured temperature signal and the measured heat flux signal; and generate information indicating one or more of the estimated values determined for the internal parameters at the one or more specified times.

At least some examples provide a system for non-invasive sensing of an object having a volume with a surface and an internal region. The system comprises a first non-invasive, heat flux sensor-temperature sensor pair and a second non-invasive, heat flux sensor-temperature sensor pair. Each of the first and second non-invasive, heat flux sensor-temperature sensor pairs includes a heat flux sensor having one or more heat flux sensor output terminals and a temperature sensor having one or more temperature sensor output terminals. The first and second non-invasive, heat flux sensor-temperature sensor pairs may be placed at different locations on or near the surface of the object. The internal region of the object has internal properties indicated by corresponding internal parameters and an internal temperature distribution. Control circuitry, coupled to the one or more heat flux sensor output terminals and the one or more temperature sensor output terminals of each of the first and second non-invasive, heat flux sensor-temperature sensor pairs, is configured to: receive a first measured temperature signal from the temperature sensor in the first non-invasive, heat flux sensor-temperature sensor pair at one or more specified times; receive a first measured heat flux signal from the heat flux sensor in the first non-invasive, heat flux sensor-temperature sensor pair at the one or more specified times; receive a second measured heat flux signal from the heat flux sensor in the second non-invasive, heat flux sensor-temperature sensor pair at the one or more specified times; determine a value for each of the internal parameters at the one or more specified times; determine an internal temperature distribution at the one or more specified times based on the measured temperature signals from the temperature sensors in the first and second non-invasive, heat flux sensor-temperature sensor pairs at the one or more specified times, the measured heat flux signals from the heat flux sensors in the first and second non-invasive, heat flux sensor-temperature sensor pairs at the one or more specified times, and the values of the internal parameters at the one or more specified times; and generate information indicating the internal temperature distribution at the one or more specified times.

At least some examples provide a system for non-invasive sensing of an object having a volume with a surface and an internal region, comprising a first non-invasive, heat flux sensor-temperature sensor pair and a second non-invasive, heat flux sensor-temperature sensor pair. Each of the first and second non-invasive, heat flux sensor-temperature sensor pairs includes a heat flux sensor having one or more heat flux sensor output terminals and a temperature sensor having one or more temperature sensor output terminals. The first and second non-invasive, heat flux sensor-temperature sensor pairs may be placed at different locations on or near the surface of the object. The internal region of the object has internal properties indicated by corresponding internal parameters and an internal temperature distribution. Control circuitry, coupled to the one or more heat flux sensor output terminals and the one or more temperature sensor output terminals of each of the first and second non-invasive, heat flux sensor-temperature sensor pairs, is configured to: receive a first measured temperature signal from the temperature sensor in the first non-invasive, heat flux sensor-temperature sensor pair at one or more specified times; receive a first measured heat flux signal from the heat flux sensor in the first non-invasive, heat flux sensor-temperature sensor pair at the one or more specified times; receive a second measured temperature signal from the temperature sensor in the second non-invasive, heat flux sensor-temperature sensor pair at the one or more specified times; receive a second measured heat flux signal from the heat flux sensor in the second non-invasive, heat flux sensor-temperature sensor pair at the one or more specified times; determine an initial value for each of the internal parameters at the one or more specified times; determine one or more internal parameters of the object at the one or more specified times based on the measured temperature signals from the temperature sensors in the first and second non-invasive, heat flux sensor-temperature sensor pairs at the one or more specified times and the measured heat flux signals from the heat flux sensors in the first and second non-invasive, heat flux sensor-temperature sensor pairs at the one or more specified times, and the values of the internal parameters at the one or more specified times; and generate information indicating one or more internal parameters of the object at the one or more specified times.

At least some examples provide a non-invasive sensor that may be placed on or near a surface of an object having a volume with an internal region, where the internal region of the object has internal properties indicated by corresponding internal parameters and an internal temperature distribution. The non-invasive sensor comprises a non-invasive, heat flux sensor-temperature sensor pair that includes a heat flux sensor having one or more heat flux sensor output terminals to provide a measured heat flux signal for the surface of the object, and a temperature sensor having one or more temperature sensor output terminals to provide a measured temperature signal for the surface of the object. The heat flux sensor and temperature sensor are configured to be subject to the same thermal conditions.

At least some examples provide a non-invasive sensor that may be placed on or near a surface of an object having a volume with a surface and an internal region. The non-invasive sensor comprises a first non-invasive, heat flux sensor-temperature sensor pair and a second non-invasive, heat flux sensor-temperature sensor pair. Each of the first and second non-invasive, heat flux sensor-temperature sensor pairs includes a heat flux sensor having one or more heat flux sensor output terminals and a temperature sensor having one or more temperature sensor output terminals. The first and second non-invasive, heat flux sensor-temperature sensor pairs are adapted to be placed at different locations on or near the surface of the object, where the internal region of the object has internal properties indicated by corresponding internal parameters and an internal temperature distribution.

Further aspects, features and advantages of the technology presented in this application will be apparent from the following description of examples, which is to be read in conjunction with the accompanying drawings.

DESCRIPTION OF EXAMPLES

Figure 1:
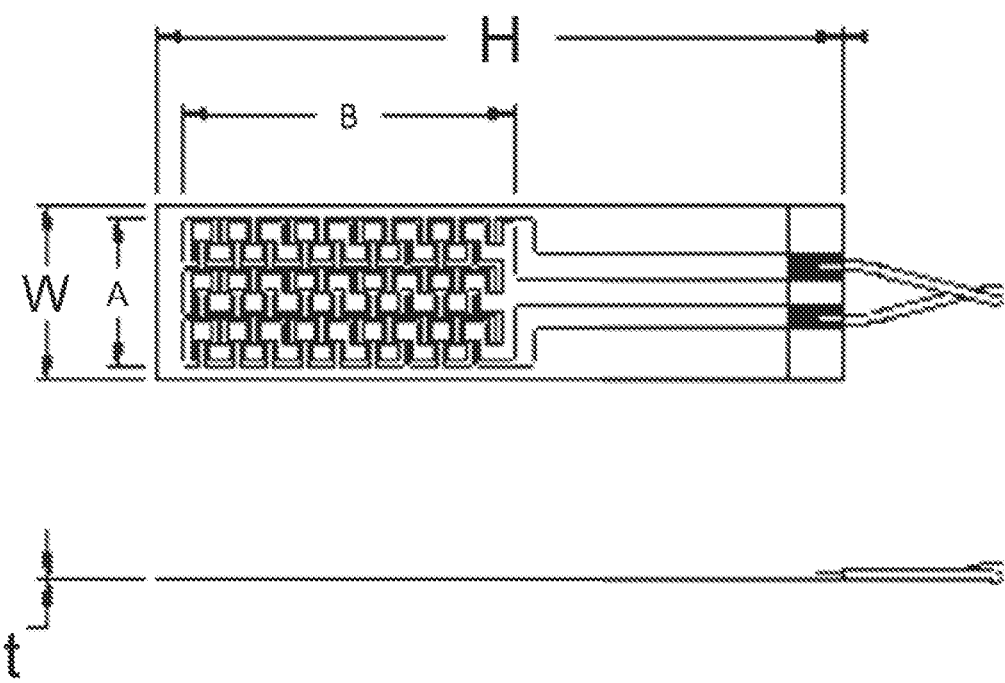
FIG. 1 shows an example of a heat flux sensor having a thickness t, a width W, and a length H in accordance with an example heat flux sensor embodiment.

Some specific examples will be discussed below. It will be appreciated that the invention is not limited to these particular examples.

The following description sets forth example embodiments for purposes of explanation and not limitation. But it will be appreciated by those skilled in the art that other example embodiments may be employed apart from these specific details. In some instances, detailed descriptions of well-known methods, interfaces, circuits, and devices are omitted so as not to obscure the description with unnecessary detail. Individual blocks are shown in some figures. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs). Software program instructions and/or data may be stored on a non-transitory, computer-readable storage medium, one or more clouds, one or more servers, and when the instructions are executed by a computer or other suitable processor control, the computer or processor performs the functions associated with those instructions.

The term signal is used herein to encompass any signal that transfers energy and/or information from one position or region to another in an electrical, electronic, electromagnetic, magnetic, or mechanical (e.g., ultrasonic signals) form. Signals may be conducted from one position or region to another by electrical or magnetic conductors, but the term signals also includes light and other electromagnetic forms of signals and other signals transferred through non-conductive regions due to electrical, electronic, electromagnetic, magnetic, or elastic effects. Signals include both analog and digital signals. An analog electrical signal includes information in the form of a continuously variable physical quantity, such as voltage. A digital electrical signal includes information in the form of discrete values of a physical characteristic, which could also be, for example, voltage.

A component, layer, or other structure is thermally conductive or thermally conducting if it sufficiently conducts thermal energy (e.g., thermal energy transferred by conduction, radiation, and/or convection) from one position or region to another that operations in the other position or region can be affected by the thermal energy. The term sensing means obtaining information from a physical stimulus, and therefore, sensing includes actions such as detecting, measuring, and so forth. Thermal sensing is sensing of a thermal stimulus such as heat, temperature, or random kinetic energy of molecules, atoms, or smaller components of matter. A thermal sensor is an electronic device that performs thermal sensing and generates signals related to thermal energy. If thermal energy includes information, then a thermal sensor or combinations of thermal sensors that detect the thermal energy may be able to sense the information. Depending on the context, different forms and/or types of thermal energy and related thermal signals, as used in this application, may be regarded as heat transfer, heat transfer signals, temperature, and temperature signals.

Unless the context indicates otherwise, the terms circuitry and circuit refer to structures in which one or more electronic components have sufficient electrical connections to operate together or in a related manner. In some instances, an item of circuitry can include more than one circuit. An item of circuitry that includes a processor may sometimes be separated into hardware and software components; in this context, software refers to stored data that controls operation of the processor or that is accessed by the processor while operating, and hardware refers to components that store, transmit, and operate on the data. Circuitry can be described based on its operation or other characteristics. For example, circuitry that performs control operations is sometimes referred to as control circuitry, and circuitry that performs processing operations is sometimes referred to as processing circuitry.

In general, sensors, processors, and other such items may be included in a system in which they are operated automatically or partially automatically. The term system refers to a combination of two or more parts or components that can perform an operation together. A system may be characterized by its operation.

An integrated structure is a structure with electrical components and connections produced by microfabrication or similar processes. An integrated structure may, for example, be on or over a substrate on which it was produced or another suitable support structure. Other components could be on the same support structure with an integrated structure, such as discrete components produced by other types of processes.

Thermal based sensing and monitoring is typically performed with only temperature sensors and/or temperature signals. For example, in order to determine the internal temperature of an object or system, invasive temperature probes are inserted at a prescribed depth of interest. An example uses invasive temperature probes that are inserted in thermowells to measure internal flow temperature within a pipe or conduit. Thermowell placement typically requires complicated procedures where the pipe or conduit surface is drilled and/or otherwise penetrated in order to place the thermowell within the internal fluid flow. A temperature sensor (e.g., thermocouple, resistance temperature device (RTD), thermistor, thermometer, etc.) is then inserted within the thermowell where it is protected from the fluid flow. Due to heat capacity of the thermowell, the response time of temperature sensors within them is slowed. Additionally, because thermowell walls may conduct heat out of (or into) the pipe or conduit, temperature sensor accuracy may be negatively impacted. Typically, this approach in measuring fluid flow temperature is more accurate than, for example, measuring surface temperature measurements of the pipe or conduit. However, due to the invasive nature of such technology, a number of design considerations typically take place before their use. These design considerations can be complicated and costly for many applications. For example, the material and/or design characteristics of the thermowell may differ based on application and need to adhere to extensive standards (e.g., American Society for Testing and Materials (ASTM) standards). Furthermore, the invasive nature of thermowells results in complicated long term maintenance, e.g., due to corrosion and/or prolonged exposure to high energy fluid flow which can cause structural stress and vibrations.

Another thermal based sensing example of where invasive probes are used for object and/or system internal temperature measurement is core body temperature measurement. For example, in healthcare, the current methods utilized and accepted as accurate methods of real-time core body temperature measurement are, for example, esophageal, rectal, and pulmonary artery based temperature measurements. All of these methods utilize invasive and often uncomfortable probes that are placed at different locations within the body. Because of their invasive nature, such methods can lead to infection and/or other complications. The invasive nature of such methods also limits the scope of where and when measurements can be made. For example, invasive probes are rarely used unless the patients have undergone anesthesia or other similar procedures. Invasive probes are also not suitable for wearable technologies or devices.

Given the limitations of invasive internal temperature measurement technologies, an alternative approach may be to make internal temperature measurements of an object or system based on surface and/or other external temperature readings (e.g., ambient temperature). This approach, however, typically results in inaccurate measurements and may require complex hardware and software systems in an attempt to determine internal temperature measurements based on such non-invasive temperature measurements. In some embodiments, multiple temperature sensors may be used on or near an object or system surface and/or internally within a device that is placed on or near the surface of the object or system. In addition, one or more thermally calibrated components (e.g., insulation pieces, precise temperature sensors, etc.) may be required. This further results in complicated and/or complex measurement systems. Other embodiments may include one or more control systems, one or more heaters, one or more coolers, and/or multiple temperature sensors. These embodiments may be, for example, designed to create and determine a zero heat-flux environment for internal temperature measurement. Such non-invasive approaches are typically slow and inaccurate, especially in changing or extreme thermal conditions. Furthermore, in some cases, for accurate internal temperature measurements, sensor and/or device placement may be limited to specific areas on an object or system surface. For example, with regard to core body temperature measurement, sensor and/or device placement may be limited to certain auxiliary locations on the body (e.g., armpit or forehead). Additionally, due to hardware complexity, embodiments may be associated with large form factors, resulting in an inconvenience for many applications. For example, with regard to core body temperature measurement, large form factors are impractical for wearable applications. With regard to non-invasive internal pipe or conduit temperature measurement, large form factors may prevent sensor and/or device mounting in certain locations, e.g., in between a pipe surface and surrounding thermal insulation. Finally, the complexity of such systems may result in manufacturing difficulty as well as increased manufacturing costs.

Other thermal based sensing applications may use temperature based signals to determine internal fluid flow via thermal anemometry. This approach requires internal probing in order to make measurements of fluid flow that correspond to measured temperature signals via established correlations. To the contrary, thermal dispersion flow meters are non-invasive systems that use temperature sensors on the surface of a pipe or conduit in between which a heater provides thermal energy into the pipe/conduit surface. The temperature difference between the temperature sensors placed before and after the heating element is correlated to internal fluid flowrate. However, thermal dispersion flow meters do not function properly with pipes made of thermally insulating materials. Furthermore, they are susceptible to inaccuracies when used in differing conditions because the specific amount of thermal energy (i.e., heat transfer) entering the pipe or conduit via the heater is unknown and can only be estimated with underlying assumptions. Thus, thermal dispersion flow meters are typically calibrated for specific conditions and use cases.

Other thermal based technologies may be used to predict (e.g., analytically determine) object or system surface heat transfer (e.g., heat flux) using surface and/or internal temperature measurements. Such techniques may be further used to determine internal properties of an object or system based on the predicted surface heat transfer (e.g., heat flux) and surface or internal temperature signals. However, these techniques may have a number of limitations such as poor accuracy, low resolution, prolonged processing time, and noise amplification due to a mathematical integration required when determining heat transfer (e.g., heat flux) from measured temperature signals.

For example, determined surface heat transfer (e.g., heat flux) of an object or system may be compared with measured surface heat transfer (e.g., via a heat flux sensor) in order to determine internal properties of the object or system. Again, due to the limitations of heat transfer (e.g., heat flux) prediction based on temperature measurements, the values determined via such techniques for internal properties of an object or system may be inaccurate and impractical for application. Furthermore, when using such techniques, there may be a mismatch between the measured temperature (e.g., surface temperature), from which surface heat transfer is determined, and the measured heat transfer (e.g., surface heat flux) of an object or system. For example, a mismatch may occur when the heat transfer (e.g., heat flux) measured at the object or system surface, e.g., via a heat flux sensor, is not the same as the heat transfer (e.g., heat flux) occurring at the location of the surface temperature sensor. This can be caused by, for example, a surface temperature sensor that is located in proximity to a heat flux sensor where it is not subject to the same thermal (e.g., heat transfer and/or temperature) conditions experienced by the heat flux sensor. In other examples, a temperature sensor may be located on or near a heat flux sensor but in a location outside of the heat flux sensor sensing area, which may also result in a mismatch of measurements. Similar issues may arise when using a temperature sensor that, for example, is located on or near a heat flux sensor sensing area but causes inadequate contact between the heat flux sensor and object/system surfaces as a result of, for example, its design (e.g., thickness) and/or materials. In this example, the mismatch occurs because the measured temperature is not an accurate representation of the surface temperature and/or the measured heat transfer is not realistic of what is occurring at the object/system surface and/or experienced by the temperature sensor. In other examples, the materials used to construct the heat flux sensor and temperature sensor and/or their surroundings may be sufficiently different (e.g., different thermal resistance values) and cause a non-uniform response to uniform thermal conditions. This may also result in a mismatch between the heat flux sensor and temperature sensor outputs.

In another example, a thin-film thermocouple, which is an example thin temperature sensor, may be located on a heat flux sensor sensing area where adequate contact is established between the heat flux sensor and object/system surfaces. In this case, although the thin-film thermocouple temperature sensor does not create any of the example issues described above (e.g., inadequate contact due to thickness) and is subject to the same thermal (e.g., heat transfer and/or temperature) conditions as the heat flux sensor, it may experience thermal shunting where the measured temperature is inaccurate due to thermal energy being conducted to or from (i.e., leaving or entering) the thermocouple junction via the thermocouple materials and/or output terminals (e.g., thermocouple leads). In such cases, the measured temperature may be lower or greater than the actual temperature experienced at or near the heat flux sensor sensing area. All of these non-limiting and example conditions are potential issues for accurate determination of an object or system internal properties when using thermal based sensing technologies.

A problem with using heat transfer (e.g., heat flux) measurements in thermal based sensing technologies is inefficiency. Heat transfer is conventionally understood and explained as a consequence of temperature gradients. This conventional approach may lead to inefficient and inaccurate heat transfer (e.g., heat flux) measurement techniques as well as general confusion between the differences of heat transfer (e.g., heat flux) and temperature. For example, one way to measure heat transfer may use one or more temperature sensors, e.g., thermocouples, RTDs, negative or positive temperature coefficient (NTC) sensors, thermistors, etc. on either side of some sort of insulating material (i.e., thermal resistance layer) to create a layered heat flux gage, a type of one-dimensional planar (i.e., flat) gage. In this example method, a determination (e.g., average) of absolute temperature on either side of the insulating material is measured, and the difference between them is used to determine the amount of heat transfer occurring through the insulating material with a calibrated or otherwise determined thermal resistance value. In another example approach, a thermocouple may be placed on either side (e.g., top and bottom) of a calibrated insulating material (i.e., thermal resistance layer), forming a thermocouple pair. The thermocouple pair may be arranged so that, when connected in series, the output of the thermocouple pair is a differential voltage that is indicative (e.g., proportional) to the temperature difference across the thermal resistance layer and to the heat transfer (e.g., heat flux) occurring through the thermal resistance layer. These example approaches may result in slow, inaccurate, high cost, and large heat flux device(s) (i.e., heat flux channel(s)) that may require multiple calibrations and may be difficult to manufacture.

Another shortfall in thermal based sensing techniques is failure to determine or otherwise account for thermal contact resistance. This leads to erroneous surface temperature measurement which may influence the accuracy of thermal based sensing and monitoring. However, modeling and/or determination of thermal contact resistance when performing thermal based sensing may be difficult and unclear. This is in part due to the complexity and inaccuracies associated with determining thermal contact resistance using only temperature signals and/or methods that predict heat transfer based on temperature signals.

The technology described in this application solves these technical problems and provides the following example technical benefits. Most importantly, in addition to a measure of surface temperature, the technology described in this application provides a measure of the heat transfer (e.g., heat flux) entering or leaving an object and/or system surface as a part of a thermal based sensing and/or monitoring routine (i.e., technique). This measure of heat transfer (e.g., heat flux) is used as a direct input and/or a boundary condition in one or more thermal mathematical model(s) that may differ for different applications. The measure of heat transfer (e.g., heat flux) as an input and/or direct boundary condition, allows for accurate and robust thermal sensing and monitoring (i.e., interrogation) techniques.

The technology performs the measure of heat transfer (e.g., heat flux) via one or more heat flux sensor(s). For the purpose of this application, the term heat flux sensor refers to a sensor designed to measure heat transfer (e.g., heat flux) using differential voltage output signals that are a consequence of the heat transfer (i.e., thermal energy) flowing through the sensor. A non-limiting example of a measure of heat transfer is heat flux which is defined as the amount of thermal energy entering or leaving a surface per unit of area per unit of time and can be measured in SI units of $W/m^2$. A heat flux sensor typically has a calibration constant (i.e., sensitivity value) that directly relates the heat flux sensor differential voltage output signals to the heat transfer (e.g., heat flux) occurring through it. A calibration constant may vary with sensor operating temperature, the effects of which can be accounted for via a determined calibration curve that specifies a calibration constant based on sensor operating temperature. As pertains to this application, it is important to note the distinctions between a heat flux sensor and a heat flux device, a heat flux channel, etc. A heat flux sensor is typically thin and has a fast response time as a result of its design. This provides example benefits including increased accuracy, a smaller form factor, and robust measurement capability unrealized by other heat transfer measurement technologies.

Additionally, the technology described in this application ensures, regardless of the proximity of the temperature sensor to the heat flux sensor (e.g., next to, on, or near the heat flux sensor sensing area, etc.), that a mismatch does not exist between the measured temperature (e.g., surface temperature) and the measured heat transfer (e.g., surface heat flux) of an object or system (e.g., the heat flux sensor and temperature sensor are subject to the same thermal conditions). For example, when possible, the temperature sensor may be located on or near the heat flux sensor sensing area while maintaining adequate contact between the heat flux sensor and object/system surfaces and, if applicable, designing for possible effects related to thermal shunting and/or thermal homogeneity of materials used for construction. In other example embodiments, the temperature sensor may be located on or near (e.g., adjacent to) the heat flux sensor and/or the heat flux sensor sensing area and may be surrounded by and/or in contact with materials that ensure the same thermal (e.g., heat transfer and/or temperature) conditions between the heat flux sensor and temperature sensor.

Another major benefit of the technology in this application is the ability to easily and quickly determine thermal contact resistance between a temperature sensor and object or system surface. This improves the accuracy and validity of thermal sensing and monitoring, especially in example applications where the effects of thermal contact resistance are not negligible and/or unpredictable.

Another major benefit of the technology in this application is non-invasiveness and simplicity of use. For example, extensive design considerations or precautions required for invasive technologies are not needed. Furthermore, the technology is not restricted to applications where invasiveness is permissible.

Further benefits of the technology in this application include minimal processing time and reduced processing power required. This benefit is in part attributed to the use of a heat flux boundary condition as well as incorporating fast and refined methods of determining thermal contact resistance. Reduced calibration needs for sensors designed for heat transfer (e.g., heat flux) measurement is another benefit. For example, the technology in this application typically only requires one calibration constant (i.e., sensitivity value) for heat transfer measurement via a heat flux sensor.

The technology in this application is based on the simultaneous use of heat flux and temperature sensors to non-invasively determine one or more internal properties of an object and/or system. Object(s) and/or system(s) are not limited to solid objects but also include, for example, fluid (e.g., water, air, etc.) or other material(s), e.g., metallurgic powder, epoxies, carbon fiber composite materials, etc. For simplicity, the term object as used in this application includes a system. For example, a pipe with fluid flowing inside is an object. The term Non-Invasive Thermal Interrogation (NITI) is used herein to refer to sensor technology based on simultaneous combinations of surface heat flux and surface temperature measurements. When placed on an object, an NITI sensor measures one or more simultaneous combinations of surface heat transfer (e.g., heat flux) and surface temperature signals that are converted to digital form and processed to determine one or more internal properties of the object. For a given measurement, the term simultaneous combination as used in this application refers to one or more surface heat transfer (e.g., heat flux) and surface temperature signals measured within a range of time (i.e., within a specified amount of time). A range of time may include a single time (i.e., a specified time). For simplicity, the term specified time as used in this application is defined to include a range of time (i.e., within a specified amount of time) as well as a single time.

Non-limiting, example applications of the NITI technology include but are not limited to: internal temperature distribution measurement of an object (e.g., mammal, non-mammal, meat, pipe/conduit, power transformer, lumber/timber, wall, machine, battery, etc.), internal parameter measurement of an object (e.g., mammal, non-mammal, meat, pipe/conduit, power transformer, lumber/timber, wall, machine, battery, etc.), blood perfusion (flow) measurement of tissue, tissue ulcer prevention and/or monitoring, hemorrhage detection and/or monitoring, concussion detection and/or monitoring, hydration measurement of tissue, metabolic heat generation measurement, athlete performance monitoring, calorie expenditure measurement, sleep monitoring, circadian rhythm monitoring, ovulation prediction and/or detection of mammals, heatstroke monitoring and/or prevention, sickle cell anemia detection and/or monitoring, anemia detection and/or monitoring, cardiovascular heath, skin flap and/or graft monitoring, disease/illness prediction, monitoring, and/or detection (e.g., Alzheimer's, Parkinson's, cancer, etc.), flow rate measurement in pipes and/or conduits, energy measurement in pipes and/or conduits, pipe/conduit freezing prevention, pipe/conduit defrosting, HVAC frost/defrost detection, HVAC system monitoring, HVAC refrigerant level monitoring, leak detection (e.g., pipe/conduit water leak, HVAC refrigerant leak, etc.), hot water heater monitoring, heat exchanger monitoring, corrosion detection and/or measurement (e.g., pipe/conduit corrosion, etc.), fouling detection and/or measurement (e.g., pipe/conduit fouling, etc.), flow level detection, presence and/or motion detection, semiconductor hardware monitoring, heat sink performance monitoring, thermal interface material monitoring, thermal resistance measurement, building insulation measurement, density, heat capacity, volumetric heat capacity, thermal conductivity, thermal inertia, thermal effusivity, thermal diffusivity, etc. of object(s) and/or material(s) (e.g., metallurgic powder, epoxies, carbon fiber composite materials, etc.) measurement, hydration/water content measurement, convective heat transfer coefficient measurement, advection heat transfer coefficient measurement, heat treatment, thermal sanitation, thermal processing, thermal comfort, thermal performance of buildings, precision agriculture, smart farms, food processing, freezing of objects, thawing of objects, metallurgic processing, 3D printing, quality control of objects, smart buildings, efficiency monitoring, object overheating prevention, object (e.g., machine, gearbox, compressor, fan, electro-mechanical system, etc.) failure detection and/or prediction/prevention, advanced temperature control, battery performance monitoring (e.g., lithium-ion battery state of health overtime, etc.), battery calorimetry, internet of things (IoT), wearable sensors, predictive analytics, prescriptive analytics, descriptive analytics, artificial intelligence, and research and development.

The term internal temperature distribution of the internal region of an object (i.e., internal temperature distribution) as used in this application includes a single temperature at a specific depth in the object at one or more specified times, multiple temperatures as a function of depth in the object at the one or more specified times, a single average temperature at a specific depth in the object at one or more specified times, multiple average temperatures as a function of depth in the object at the one or more specified times, a single highest or lowest temperature in the object at one or more specified times, multiple highest or lowest temperatures in the object at the one or more specified times, a single highest or lowest average temperature in the object at one or more specified times, or multiple highest or lowest average temperatures in the object at the one or more specified times. Furthermore, the internal temperature distribution of the internal region of the object is defined to include measures of object surface temperature. For example, the internal temperature distribution may be evaluated at the object surface (i.e., depth (x) of 0) at one or more specified times.

The term internal parameters of the internal region of an object (i.e., internal parameters) as used in this application includes one or more thermal, physical, mechanical, etc. characteristics of the object. For example, internal parameters of the object may include the thermal conductivity of the object, the density of the object, the thermal heat capacitance of the object, the volumetric heat capacity of the object, the thermal diffusivity of the object, the thermal inertia of the object, the thermal effusivity of the object, the steady-state thermal resistance of the object, the internal or external convection coefficient of the object, the internal or external advection coefficient of the object, the thickness of the object, the volume of the object, the mass of the object, the cross-sectional area of the object, the porosity of the object, the state of the object (e.g., liquid, solid, gas, etc.), the depth of interest from the surface of the object, etc. Some internal parameters may be based on a combination of internal parameters (e.g., a quotient and/or product of two or more internal parameters). Furthermore, not all internal parameters of an object may be utilized and/or necessary for an NITI embodiment and/or application. For simplicity, the term internal parameters as used in this application includes one or more internal parameters that are necessary and/or desired for the NITI embodiment being performed for the object (i.e., corresponding internal parameters).

NITI Sensor Example Embodiments

Example sensor embodiments for NITI (i.e., NITI sensors) include one or more heat flux sensors and one or more temperature sensors. A heat flux sensor and a temperature sensor that are subject to the same thermal (e.g., heat transfer and/or temperature) conditions and make simultaneous measurements at one or more specified times are referred to as a heat flux sensor-temperature sensor pair (i.e., sensor pair). A NITI sensor may also include an external thermal device that is used with a control circuitry intended for NITI.

In other example sensor embodiments, an optional external thermal device creates a thermal energy source on one side of a NITI sensor that travels through the NITI sensor and into an object for which measurements are being made. In other example embodiments, an optional external thermal device creates a thermal energy sink (i.e., heatsink) on one side of a NITI sensor that causes heat transfer from an object, for which measurements are being made, through the NITI sensor, and into the heatsink. An external thermal device may be a heater and/or cooler (e.g., a Peltier device) that is used with a control circuitry intended for NITI to create a thermal event (heating and/or cooling) so that differing simultaneous combinations of heat transfer (e.g., heat flux) and temperature signals can be generated at an object surface, acquired (e.g., measured), and processed. An external thermal device may operate in any manner (steady, periodic, cycled, etc.). In some example embodiments, an external thermal device may be used to provide a periodic (e.g., sinusoidal) temperature and/or heat flux condition at the object surface over time. Further example embodiments use phase angle determination techniques with one of more of the NITI techniques described to determine one or more internal properties of the object.

Typically, the external thermal device is adapted to provide the thermal event to an area encompassing the entirety of the heat flux sensor-temperature sensor pair where, at a minimum, the entire heat flux sensor sensing area is subject to the thermal event. In other example embodiments, the external thermal device may be adapted to provide the thermal event to an area encompassing the entirety of the heat flux sensor-temperature sensor pair as well as object surface areas surrounding the heat flux sensor-temperature sensor pair. In other example embodiments, an external thermal device may provide a thermal event to multiple heat flux sensor-temperature sensor pairs. In other example embodiments, for example, when the object undergoing interrogation has a non-planar (e.g., curved) surface, an external thermal device may be designed provide a thermal event to the area including a heat flux sensor-temperature sensor pair and not the surrounding object surface, In other example sensor embodiments, an external thermal device may be used with a control circuitry intended for NITI to eliminate the heat transfer occurring between the object and NITI sensor surfaces. For example, an external thermal device (e.g., heater) could apply or remove heat (i.e., thermal energy) at the object surface and create a "zero heat-flux environment" between the contacting object and NITI sensor surfaces. In a zero heat-flux environment, the heat flux sensor component of the NITI sensor, outputs and maintains a minimal voltage (e.g., "0") and, when in steady-state conditions, the corresponding surface temperature measured by the NITI sensor at the object surface is indicative of the internal temperature distribution of the internal region of the object.

With regard to example NITI sensor and/or system embodiments described below, CHFT+/− refers to Combined Heat Flux and Temperature Sensor (i.e., heat flux sensor-temperature sensor pair) and the + or − indicates use of an external thermal device (e.g., heater, Peltier device, etc.) that is used with a control circuitry intended for NITI or not, respectively. DUO NITI refers to NITI sensor and/or system embodiments with multiple (e.g., two) NITI sensors (e.g., CHFT+ or CHFT−) operating in parallel. DUO NITI example embodiments may, for example, use differential and/or quotient based data processing methods to simplify and make more robust NITI measurements. Furthermore, DUO CHFT+ refers to DUO NITI example embodiments that only utilize two or more parallel CHFT+ embodiments. Similarly, DUO CHFT− refers to DUO NITI example embodiments that only utilize two or more parallel CHFT− embodiments. DUO CHFT+/− refers to DUO NITI example embodiments that utilize at least one CHFT+ example embodiment and at least one CHFT− example embodiment operating in parallel. As related to this application, CHFT+, CHFT−, DUO CHFT+/−, DUO CHFT+, and DUO CHFT− are non-limiting examples of NITI sensor embodiments that may be utilized in different NITI systems, some of which are described below.

Although heat flux device(s), heat flux channel(s), etc. may be used for NITI, heat flux sensor(s) are preferred for reasons described prior. All kinds of heat flux sensor(s) (i.e., heat flux gage(s), heat flux gauge(s), heat flux transducer(s), heat flux meter(s), heat flow meter(s), heat flow gage(s), heat flow gauge(s), etc.) that are manufactured using a variety of methods and technologies (e.g., thin-film technologies, thick-film technologies, thermopile technologies, differential thermopile technologies, thermoelectric technologies, Seebeck effect technologies, transverse Seebeck effect technologies, butt-weld technologies, Microelectromechanical System (MEMS) based technologies, Nanoelectromechanical System (NEMS) based technologies, Complementary metal-oxide-semiconductor (CMOS) based technologies, additive manufacturing technologies, screen printing technologies, ink-jet technologies, textile sensor technologies, wire-wound technologies, RTD based technologies, NTC based technologies, thermistor based technologies, semiconductor based technologies, etc.) may be used for NITI. In some example embodiments, the one or more heat flux sensors are based on differential thermopile technology as described by ASTM standard E2684 and further discussed in ASTM standard E2683. A differential thermopile is a type of passive electronic transducer that converts thermal energy into electrical energy (e.g., voltage and/or current). A differential thermopile is typically composed of several thermocouples connected in series or, less commonly, in parallel. Typically, the thermocouples (i.e., thermocouple junctions) are located on either side of one or more materials (i.e., thermal resistance layer). The individual thermocouples (i.e., thermocouple junctions) measure the temperature differential from their junction point to the point in which the thermocouple voltage output is measured. When in series, the voltage output of two thermocouples on either side of a thermal resistance layer (i.e., a differential thermocouple pair or thermocouple pair) is typically a differential voltage that is related (e.g., proportional) to the temperature difference across (e.g., through) the thermal resistance layer and to the heat transfer (e.g., heat flux) occurring through the thermal resistance layer. Adding more thermocouple pairs in series increases the magnitude of the differential voltage output, consequently resulting in higher heat flux sensor sensitivity. The differential voltage output is also affected by the thermocouple (i.e., thermoelectric) materials used. Hence, for a given temperature difference across a thermal resistance layer, some thermocouple materials may result in a higher differential voltage output than others. Thus, thermocouple material selection also impacts heat flux sensor sensitivity. Likewise, the materials and/or thickness used for the thermal resistance layer may affect heat flux sensor sensitivity as well as heat flux sensor response time. Differential thermopiles can be constructed with a single thermocouple pair, composed of at least two thermocouple junctions, or multiple thermocouple pairs. Differential thermopiles do not measure absolute temperature, but instead generate a differential voltage output indicative of (e.g., proportional to) a local temperature difference or temperature gradient. This temperature gradient, as previously mentioned, is a consequence of the heat transfer (e.g., heat flux) occurring through the differential thermopile and/or thermal resistance layer and, thus, indicates a measure of the heat transfer (e.g., heat flux) occurring through the differential thermopile and/or thermal resistance layer.

One example differential thermopile for heat transfer measurements is constructed using thin-film materials and polyimide (i.e., thermal resistance layer) to create a thin heat flux sensor with accurate readings and fast response time («1 second). Another example may be differential thermopiles constructed via one or more electrically conductive through holes (i.e., VIAs) in a thermal resistance layer. Other examples could include devices that are based on differential thermopile technology but are designed to convert thermal energy to electrical power via, for example, thermal energy harvesting (e.g., Thermoelectric Generators (TEGs)). In addition to thermal energy harvesting, these devices can be utilized as heat flux sensors given they can output a differential voltage indicative of (e.g., proportional to) the heat transfer (i.e., thermal energy) occurring through the device. However, due to different design criteria, current TEG technology is often expensive and have large form factor when compared to differential thermopiles that are designed for heat flux sensor applications. Thus, using such devices can result in difficulty of use and/or inaccuracy of heat transfer (e.g., heat flux) measurements as well as slow response time. Another example is textile based heat flux sensor(s) where a differential thermopile is constructed within fabric or other materials designed to be worn or otherwise in contact with or in proximity to, for example, the human body.

For simplicity, the measure of heat transfer measured by heat flux sensor(s) as used in this application is heat flux with units of $W/m^2$. This is an example and non-limiting measure of heat transfer that may be used for NITI and/or associated topics (e.g., heat flux sensor design, thermal contact resistance effects, data processing methods, etc.).

FIG. 1 shows an example of a heat flux sensor based on differential thermopile technology having a thickness t, a width W, and a length H. A sensing area is defined by a width A and a length B, and sensor outputs include heat flux output voltage leads (i.e., output leads).

Figure 2A:
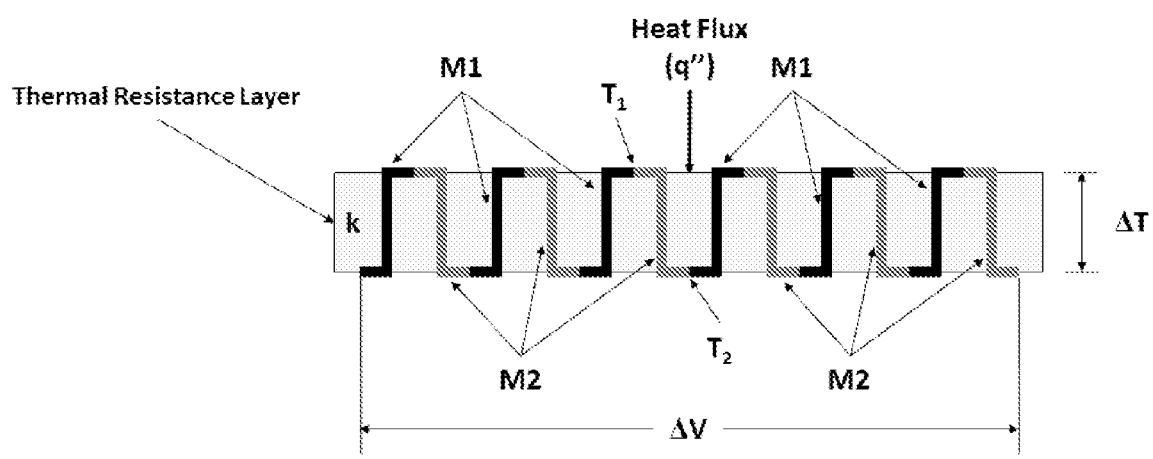
FIG. 2A shows a cross-section of a differential thermopile that includes a thermal resistance layer in accordance with an example embodiment.

FIG. 2A shows a cross-section of an example differential thermopile that includes a thermal resistance layer where k is the thermal conductivity of the thermal resistance layer, $T_1$ is a hot temperature junction, $T_2$ is a cold temperature junction, $\Delta T$ is the temperature difference between $T_1$ and $T_2$ and equivalent to the temperature difference across the thermal resistance layer, and $\Delta V$ is the differential voltage output by the thermocouple pairs connected in series and is directly indicative of (e.g., proportional to) $\Delta T$, which is a consequence of q", the heat flux occurring through the thermal resistance layer. The greater the number of thermocouple pairs, the greater the heat flux sensor sensitivity (greater $\Delta V$ for a given amount of q"). In this example, each temperature junction is formed by connecting two dissimilar thermoelectric materials (e.g., M1 and M2) in series through the thermal resistance layer. Dissimilar thermoelectric materials may include materials that have different Seebeck coefficients in order to generate a thermoelectric voltage (e.g., copper and constantan, copper and nickel, copper and silver, antimony and bismuth telluride, positively doped materials and negatively doped materials, p-type semiconductor materials and n-type semiconductor materials, etc.)

Figure 2B:
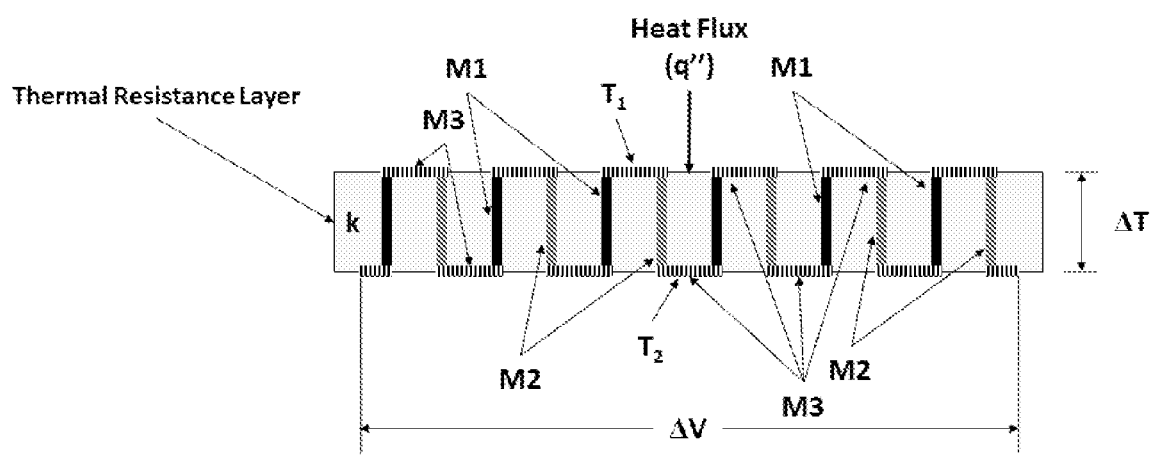
FIG. 2B shows a cross-section of a differential thermopile that includes a thermal resistance layer and may be easier to manufacture in accordance with an example embodiment.

FIG. 2B shows another example differential thermopile that includes two dissimilar thermoelectric materials (i.e., M1 and M2) as well as an electrical conductor (M3). In this example embodiment, M3 is used to connect M1 and M2 in series through the thermal resistance layer. This configuration of the example differential thermopile has example benefits including lower cost of manufacture, higher sensitivity, greater design freedom, etc. and may be realized using one or more manufacturing technologies (e.g., MEMS based technologies, NEMS based technologies, CMOS based technologies, additive based technologies, etc.). In other example embodiments, manufacturing may further be simplified where M3 is designed to be the same material as M1 or M2.

Figure 3:
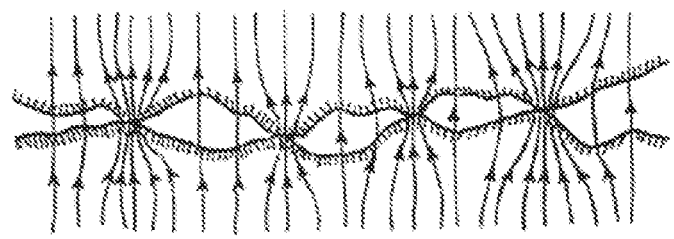
FIG. 3 shows an example where heat flux is imposed across a junction, and the flow of heat is generally restricted to conduction through the contact spots.

When a thermocouple junction is formed by pressing two similar or dissimilar metallic materials together or when a temperature sensor is put in contact with an object surface, only a small fraction of the nominal surface area is actually in contact because of the non-flatness and roughness of the contacting surfaces. If a heat flux is imposed across the junction and/or the surfaces in contact, the flow of heat (i.e., thermal energy) is generally restricted to conduction through the contact spots. See the example shown in FIG. 3. The limited number and size of the contact spots results in an actual contact area which is significantly smaller than the apparent contact area. This limited contact area and the presence of gaps causes a thermal resistance referred to as contact resistance or thermal contact resistance ($R_C"$).

The presence of thermal contact resistance ($R_C"$) affects the quality of temperature measurement. Specifically, the presence of thermal contact resistance ($R_C"$) between a temperature sensor of, for example, an example NITI embodiment and object surface causes inaccurate temperature readings. In other words, the actual surface temperature of an object differs from what is measured by a temperature sensor even when adequate contact and thermal shunting design is achieved via, for example, thin-film thermocouple technology. This inaccuracy is related to the amount of thermal contact resistance ($R_C"$) present (typically constant) and the heat flux occurring through it at a specified time. This relationship is expressed below mathematically:

$$T_{Surface}(t) = T_{Sensor}(t) - q_{Sensor}"(t) \times R_C" \quad [1]$$

where heat flux is defined to be positive when entering the object and where:
t is a specified time, $q_{Sensor}"(t)$ is the measured heat flux at the specified time, $T_{Sensor}(t)$ is the sensor measured surface temperature (i.e., measured sensor temperature, measured temperature) at the specified time, and $T_{Surface}(t)$ is the actual surface temperature at the specified time. As pertains to this application, unless the context indicates otherwise, the thermal contact resistance ($R_C"$) between a temperature sensor of an example NITI sensor embodiment and object surface may be referred to as the thermal contact resistance between the NITI sensor and the object surfaces.

Figure 4:
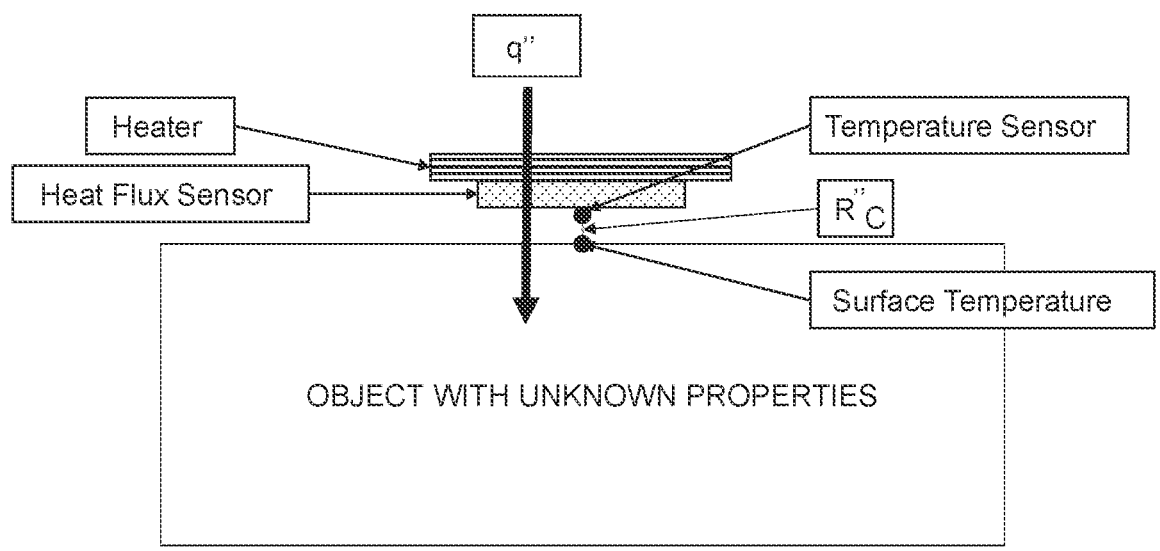
FIG. 4 shows a cross-section of an example CHFT+ embodiment that includes a heat flux sensor and a temperature sensor placed on a surface of an object with unknown internal properties where a heater (external thermal device) is placed on the heat flux sensor.

FIG. 4 shows an example CHFT+ embodiment that includes a heat flux sensor and a temperature sensor placed on a surface of an object with unknown internal properties relating to an internal region of the object and where a heater (i.e., external thermal device) is placed on the heat flux sensor. In this example, a heat flux sensor contacts with a temperature sensor which contacts with a surface of the object. Again, the limited contact area between the temperature sensor and object surface causes a thermal resistance between the temperature sensor and the object surface temperature and is shown as a thermal contact resistance ($R_C''$). Additionally, layers (e.g., as a result of protective layers, adhesives, etc.) on the temperature sensor can impact (e.g., increase) the amount of thermal contact resistance ($R_C''$) present. Heat flux ($q''$) is shown as a vector pointing into the object and is defined to be positive in that direction. Thus, as indicated in Equation [1], the object's actual surface temperature ($T_{Surface}(t)$) is determined using the measured temperature from the temperature sensor ($T_{Sensor}(t)$), the measured heat flux from the heat flux sensor ($q_{Sensor}''(t)$), and the thermal contact resistance ($R_C''$). In some example embodiments, an effort may be made to minimize the thermal contact resistance ($R_C''$) in order to assume a value of "0" in Equation [1]. This may be done, for example, by using thermally conductive adhesives in between the contacting surfaces.

In other example embodiments, to obtain an accurate actual surface temperature measurement ($T_{Surface}(t)$), an estimated value for the thermal contact resistance ($R_C''$) may need to be determined (e.g., measured). In some cases, the estimated thermal contact resistance ($R_C''$) (i.e., thermal contact resistance ($R_C''$)) value may be determined to be negligible or zero. In other cases, the estimated thermal contact resistance ($R_C''$) value may be determined using predetermined specifications from, for example, a manufacture specification for an adhesive tape used to mount an NITI sensor.

Example embodiments are capable of making accurate NITI measurements of an object whether conducted in steady-state or transient environments. The example embodiments utilize heat flux boundary conditions in their respective thermal mathematical models (heat flux is an input) which are more robust and accurate than temperature based boundary conditions. Example outputs include accurate values for internal properties of an object such as an internal temperature distribution of the internal region of the object and/or one or more internal parameters of the object.

Figure 5:
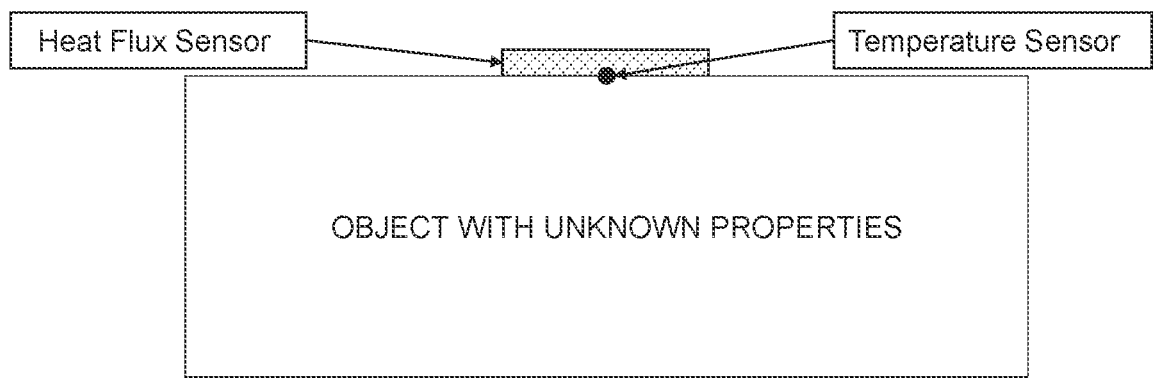
FIG. 5 shows a cross-section of an example CHFT− embodiment that includes a heat flux sensor and a temperature sensor placed on a surface of an object with unknown internal properties.

Referring to FIG. 5, an example CHFT− embodiment includes a heat flux sensor and a temperature sensor placed on a surface of an object with unknown internal properties. One example application is in situations where there is some form of an external thermal event occurring, e.g., a CHFT− is placed on an engine where the external thermal event is the heat produced and emitted by the engine. Another application is where the CHFT− is placed on the body of a human or other animal, e.g., an athlete exercising. In this latter example, the combination of body heat dissipation and airflow moving over the CHFT− corresponds to an external thermal event. Other external thermal events could be sourced from a heat lamp, a fan, a heat sink, solar radiation, contact with other objects (e.g., metal plates), etc. that are not used with a control circuitry intended for NITI (i.e., uncontrolled external thermal event).

Figure 6A:
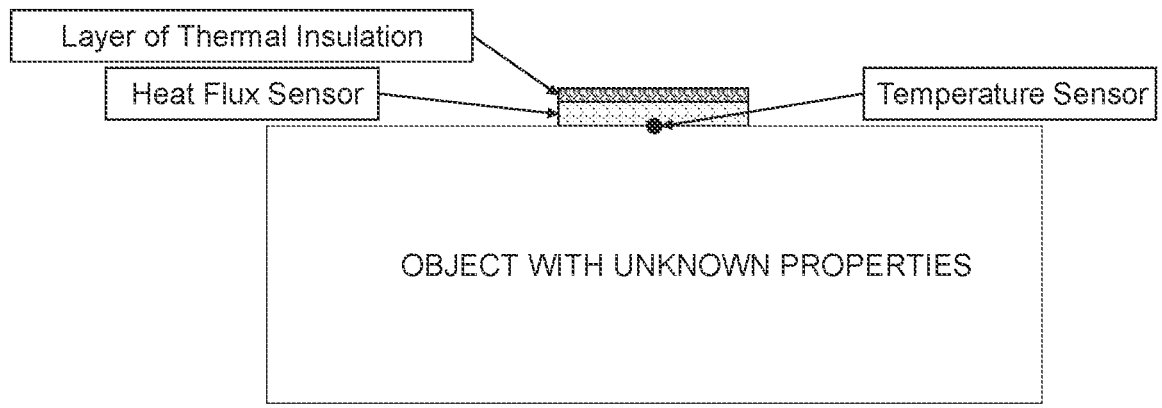
FIG. 6A shows a cross-section of an example CHFT− embodiment that includes a heat flux sensor, a temperature sensor, and a piece of insulation on the heat flux sensor and temperature sensor (i.e., heat flux sensor-temperature sensor pair).

To limit heat flux noise and sporadic signals from registering as a result of, for example, small environmental changes and/or other external stimuli, a piece of thermal insulation (i.e., layer of thermal insulation or insulation piece) may be placed on top of the CHFT− as shown in FIG. 6A. This piece of insulation acts as a filter and only allows substantive heat flux and temperature signals to be detected by the CHFT−. Furthermore, the thermal insulation piece can be used to control (i.e., limit, increase, etc.) the amount of heat flux occurring through the CHFT−. The thickness, material, form factor, and size of the insulation piece is dependent on the application the CHFT− is being used for among other factors. In some example embodiments, thermal insulation may be embedded within a substrate or material on which the heat flux sensor and/or temperature sensor is mounted. For example, air gaps or other areas with low thermal conductivity may be designed within a printed circuit board (e.g., rigid and/or flex material) that is used to arrange and connect electrically connect to the heat flux sensor and/or temperature sensor.

Figure 6B:
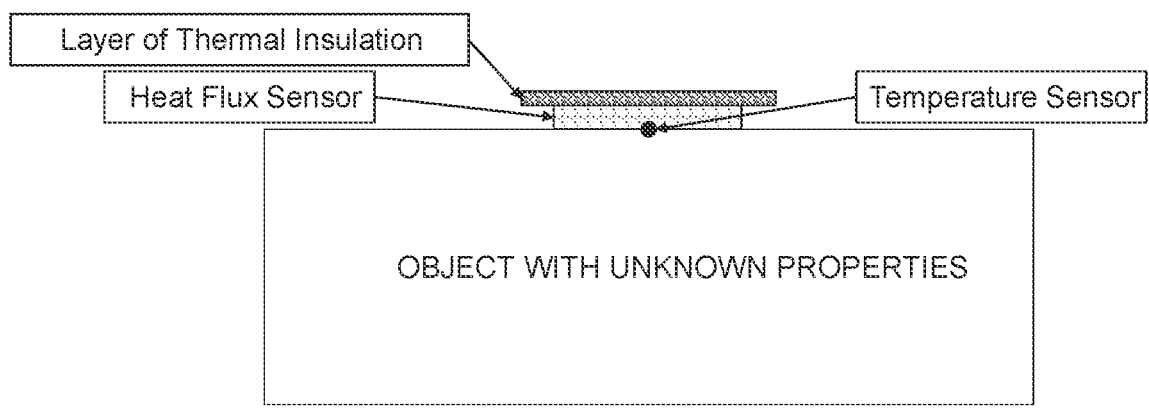
FIG. 6B shows a cross-section of an example CHFT− embodiment that includes a heat flux sensor, a temperature sensor, and a piece of insulation on the heat flux sensor and temperature sensor (i.e., heat flux sensor-temperature sensor pair) as well as a portion of the surrounding object area.
Figure 6C:
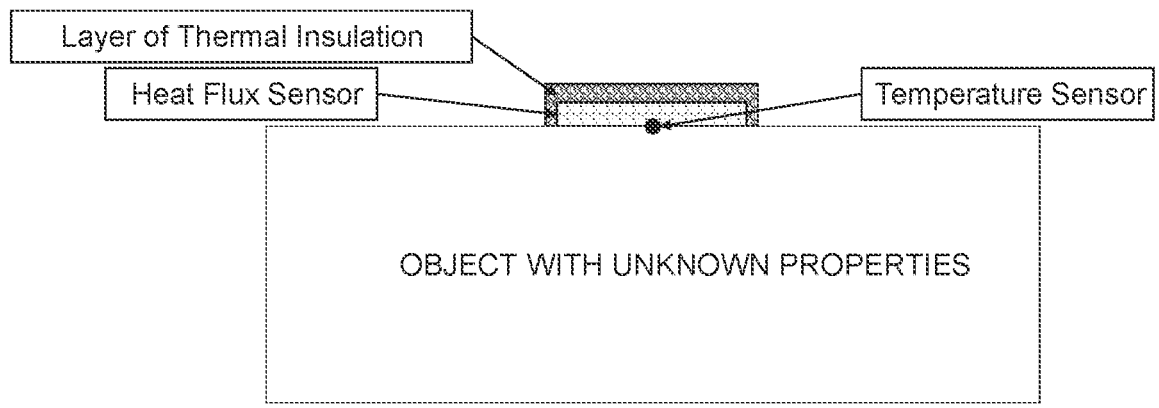
FIG. 6C shows a cross-section of an example CHFT− embodiment that includes a heat flux sensor, a temperature sensor, and a piece of insulation on and surrounding the heat flux sensor and temperature sensor (i.e., heat flux sensor-temperature sensor pair).

FIG. 6A shows an example where the thermal insulation piece is adapted to cover the entirety of the heat flux sensor-temperature sensor pair. In other example embodiments, as illustrated in FIG. 6B, the insulation piece may also overlap object surface areas surrounding the heat flux sensor-temperature sensor pair. In some example embodiments, such as illustrated in FIG. 6C, the thermal insulation piece or additional thermal insulation may be specified to surround the heat flux sensor and/or temperature sensor to minimize thermal loss. In some example embodiments thermal insulation materials could include metals or other thermally conductive materials designed to enhance and increase the amount of heat flux occurring through the CHFT−. The insulating, filtering, and heat flux control techniques shown in FIG. 6A-FIG. 6C may optionally be used for some or all NITI sensor embodiments.

Figure 7A:
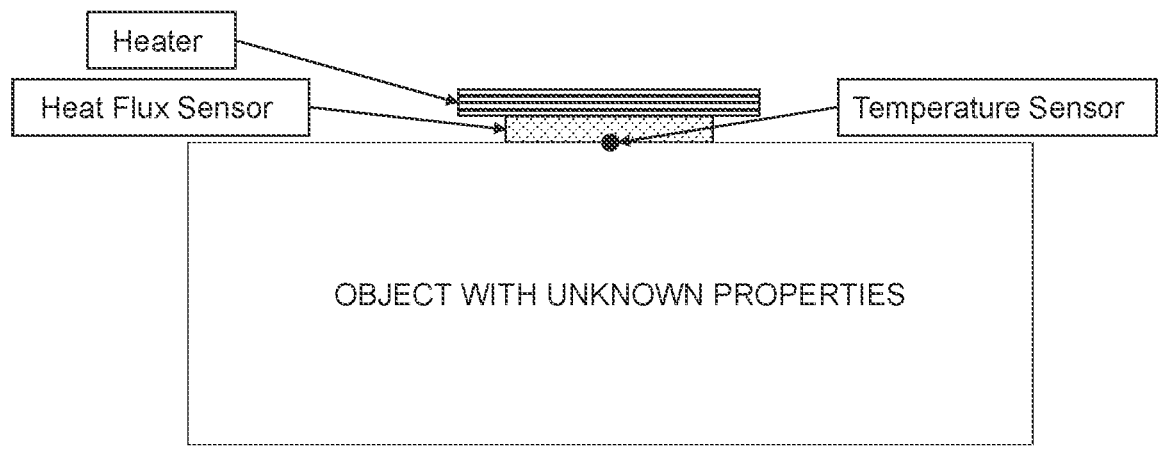
FIG. 7A shows a cross-section of an example CHFT+ embodiment that includes a heat flux sensor, a temperature sensor, and an external thermal device (e.g., a heater).
Figure 7B:
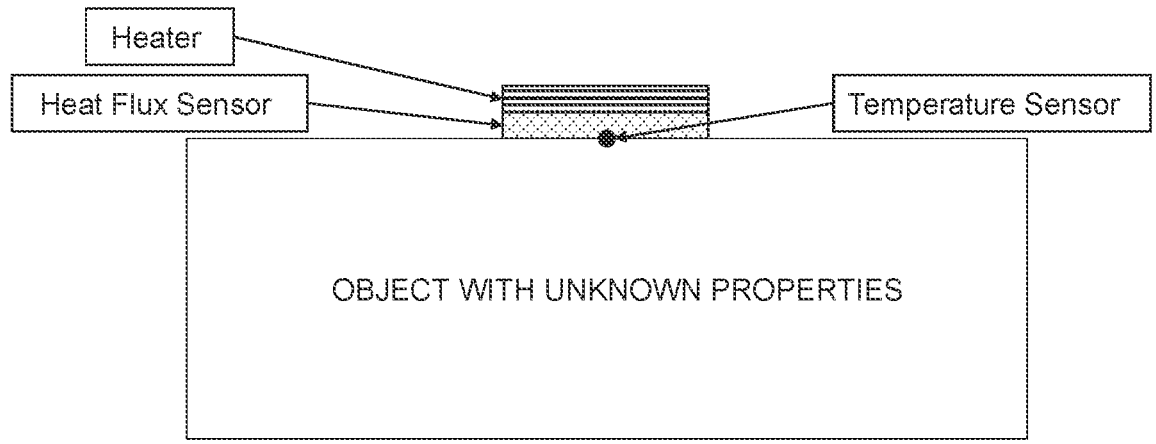
FIG. 7B shows a cross-section of an example CHFT+ embodiment that includes a heat flux sensor, a temperature sensor, and an external thermal device (e.g., a heater) that provides a thermal event to the heat flux sensor-temperature sensor pair.
Figure 7C:
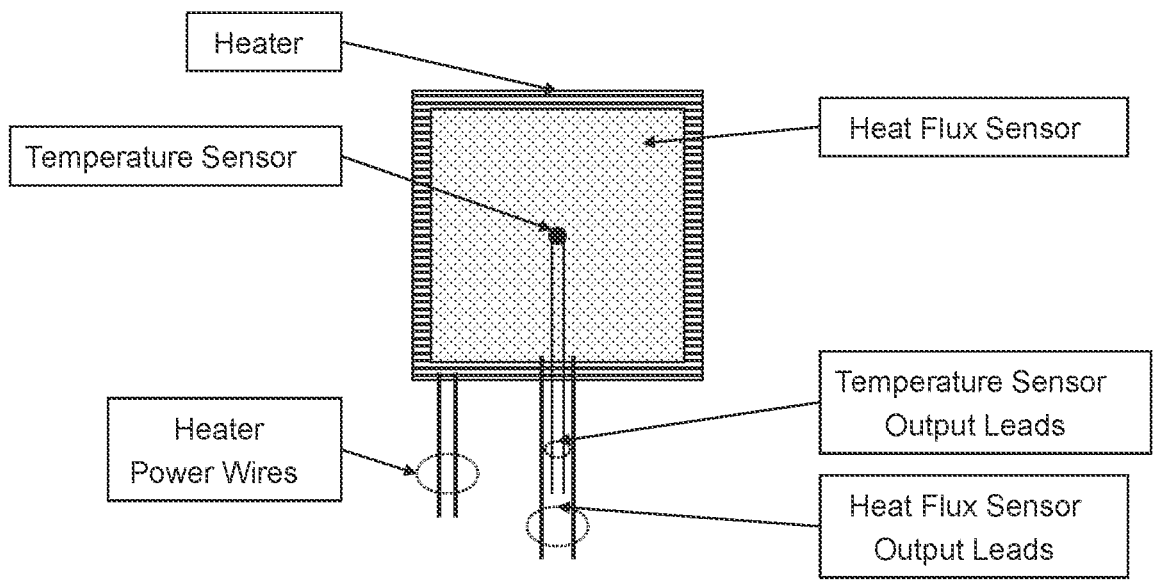
FIG. 7C shows an example CHFT+ embodiment which includes a temperature sensor, a heat flux sensor, a heater, and corresponding output terminals.

Referring to FIG. 7A, example CHFT+ embodiments include a heat flux sensor, a temperature sensor, and an external thermal device, e.g., a heater, a cooler, a fluid flow channel, a fan, a heat lamp, etc. that is used with a control circuitry intended for NITI. CHFT+ embodiments are particularly useful when external thermal events do not occur and, for the most part, steady-state conditions are maintained. However, they may also be used in situations where an uncontrolled external thermal event is occurring. With the external thermal device, the CHFT+ can generate a controlled thermal event that creates a transient response (i.e., differing thermal signals). For example, the external thermal device can cycle heater (i.e., an external thermal device) power to provide a periodic thermal event at an object surface. When needed, external thermal devices can be controlled to achieve steady-state conditions. In other example embodiments, a CHFT+ may include more than one external thermal device. For example, both a heater and a Peltier cooler may be utilized as external thermal devices in order to create thermal heat sources and thermal heat sinks as desired. As another example, a single Peltier device may be used as the external thermal device to achieve both thermal heating and cooling. In FIG. 7A, a heater is illustrated as an example of an external thermal device. In this example, the heater (i.e., the external thermal device) is designed to provide the thermal event to an area encompassing the entirety of the heat flux sensor-temperature sensor pair as well as object surface areas surrounding the heat flux sensor-temperature sensor pair. In FIG. 7B, another example embodiment is illustrated where the heater (e.g., the external thermal device) is designed to provide the thermal event to an area encompassing the entirety of the heat flux sensor-temperature sensor pair only. A top view of an example CHFT+ embodiment is shown in FIG. 7C which includes a temperature sensor with output leads (i.e., output terminal connection), a heat flux sensor with output leads (example output terminals), and a heater (an example external thermal device) with power leads (example power terminals). In this example, the output and power leads are connected (e.g., soldered) to the corresponding output terminals of each component. In other example embodiments, the output terminals may be connected to other terminals (e.g., electrically conductive pads) designed for surface mounted or through-hole devices, e.g., by using rigid and/or flex printed circuit board technologies. In other example CHFT+ embodiments, a heater may be constructed within, for example, a printed circuit board via trace patterns with controlled resistance, shape, and/or size that directly connect to a power source within the circuitry. This may ease manufacturing processes given the embedded aspect of such a design. In some example NITI sensor embodiments, one or more of the temperature sensor output leads may be connected to a ground terminal and/or reference resistor that may be used as a part of circuitry to make temperature measurements based on a temperature sensor resistance (e.g., thermistor).

Figure 7D:
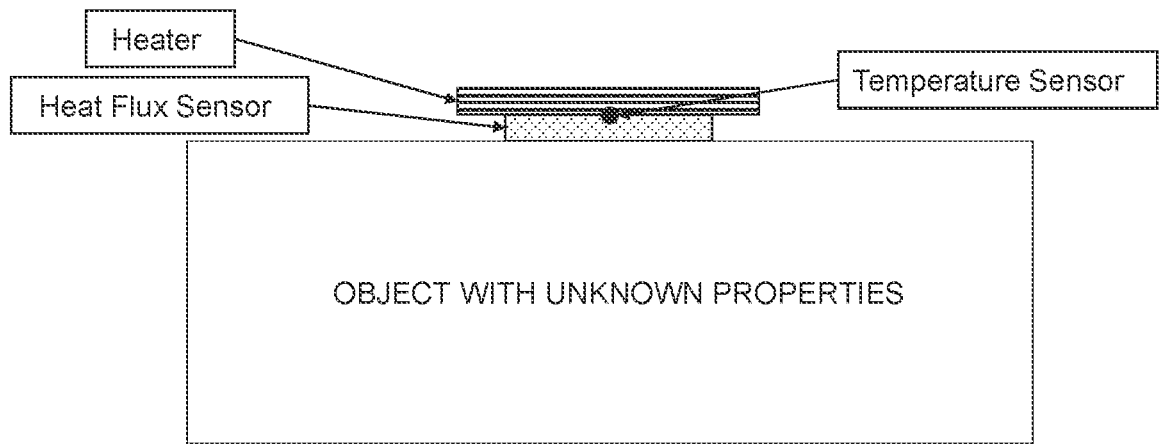
FIG. 7D shows a cross-section of an example CHFT+ embodiment that includes a heat flux sensor, a temperature sensor, and an external thermal device (e.g., a heater), where the temperature sensor is located between the heat flux sensor and the external thermal device.

In other example embodiments, such as illustrated in FIG. 7D, the temperature sensor may be located on or near the opposite side of the heat flux sensor sensing area that is in contact with the object surface. In these example embodiments, the output of the temperature sensor may be assumed to be the same as the output of a temperature sensor as configured in FIG. 7A. This is especially the case when the heat flux sensor has a negligible thermal resistance as a result of its design (e.g., low thickness, high thermal conductivity, etc.) and/or where a zero heat-flux condition is created. In other example embodiments, for example embodiments where the thermal resistance of the heat flux sensor may not be negligible, the one or more effects of the heat flux sensor's thermal resistance may be modeled as a part of the thermal contact resistance between the temperature sensor and object surfaces. In other example embodiments, for example, embodiments where the number of heat flux sensor junctions and heat flux sensor sensitivity are accurately known, the heat flux sensor output may be used to determine the temperature difference across the heat flux sensor in real-time such that the output may be combined with the temperature sensor in FIG. 7D to determine the temperature between the heat flux sensor and object surface.

Figure 7E:
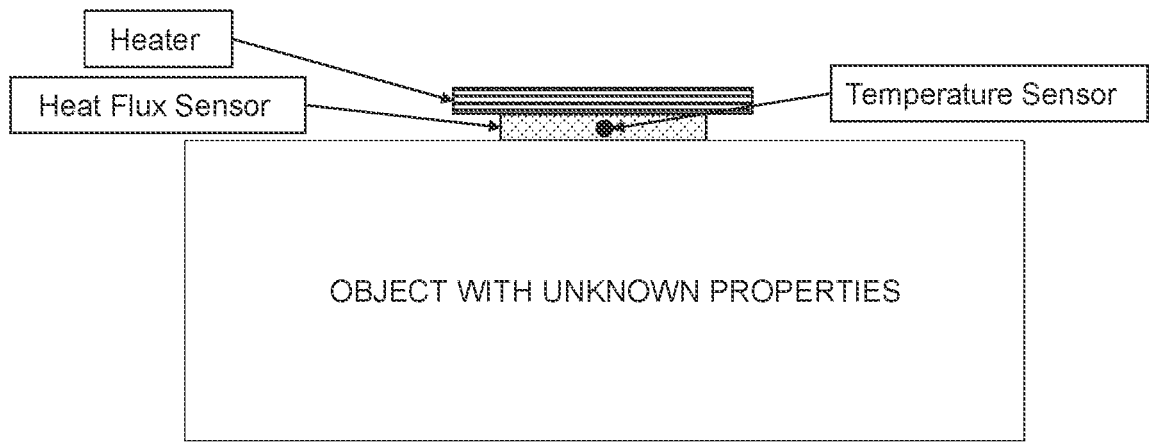
FIG. 7E shows a cross-section of an example CHFT+ embodiment that includes a heat flux sensor, a temperature sensor, and an external thermal device (e.g., a heater), where the temperature sensor is located within the heat flux sensor.

In other example embodiments, such as illustrated in FIG. 7E, the temperature sensor may be embedded within the heat flux sensor and/or the heat flux sensor sensing area.

Figure 7F:
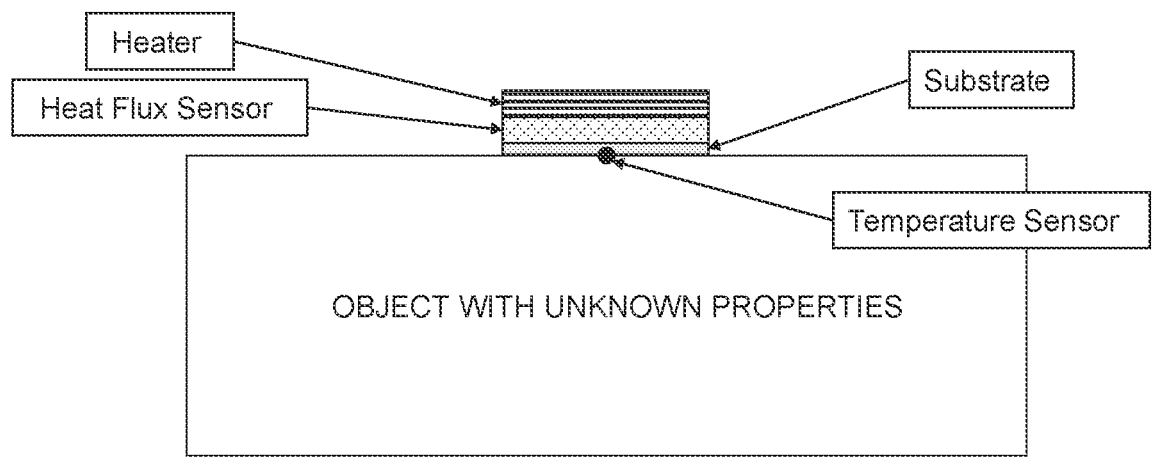
FIG. 7F shows a cross-section of an example CHFT+ embodiment that includes a heat flux sensor, a temperature sensor, and an external thermal device (e.g., a heater), where the heat flux sensor and the temperature sensor are separated by a substrate.
Figure 7G:
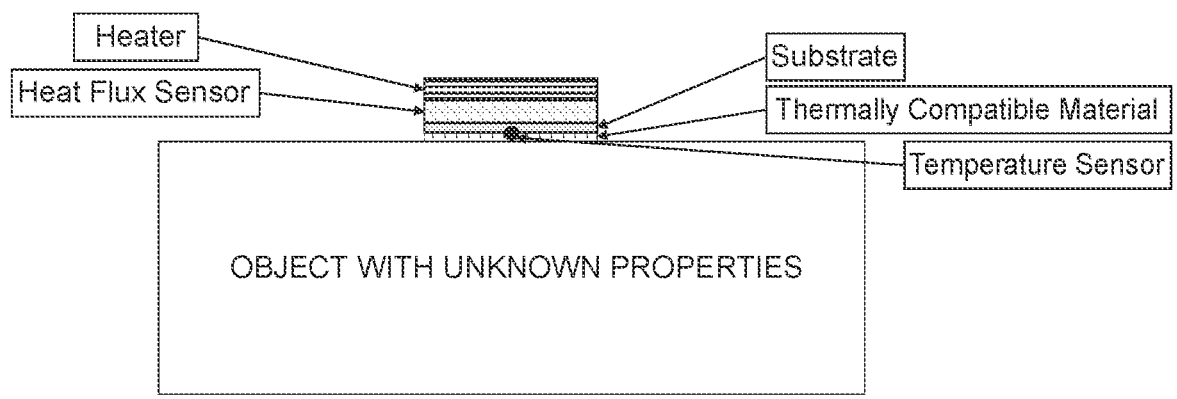
FIG. 7G shows a cross-section of an example CHFT+ embodiment that includes a heat flux sensor, a temperature sensor, and an external thermal device (e.g., a heater), where the heat flux sensor and the temperature sensor are separated by a substrate and the temperature sensor is surrounded by thermally compatible materials.

In other example embodiments, such as illustrated in FIG. 7F, the heat flux sensor and temperature sensor may be located on either side of a substrate while avoiding a mismatch of measurements. For example, the heat flux sensor and temperature sensor may be aligned on either side of a substrate (e.g., a flexible printed circuit board) such that the heat flux sensor and/or the heat flux sensor sensing area encompass the temperature sensor on the opposing side. This may be achieved by, for example, placing the heat flux sensor beneath or on top of the temperature sensor that is on the opposing side of the substrate. In these example embodiments, the heat flux sensor and/or temperature sensor may be further surrounded by and/or in contact with other thermally compatible materials (e.g., materials with thermal resistances close to the temperature/or heat flux sensor) to ensure a uniform thermal energy flow (e.g., heat flow) through the heat flux sensor and temperature sensor. An example embodiment is illustrated in FIG. 7G.

The non-limiting features of the example embodiments illustrated in FIG. 7D-FIG. 7G may optionally be used in any example NITI embodiments, including example CHFT− embodiments.

Figure 8:
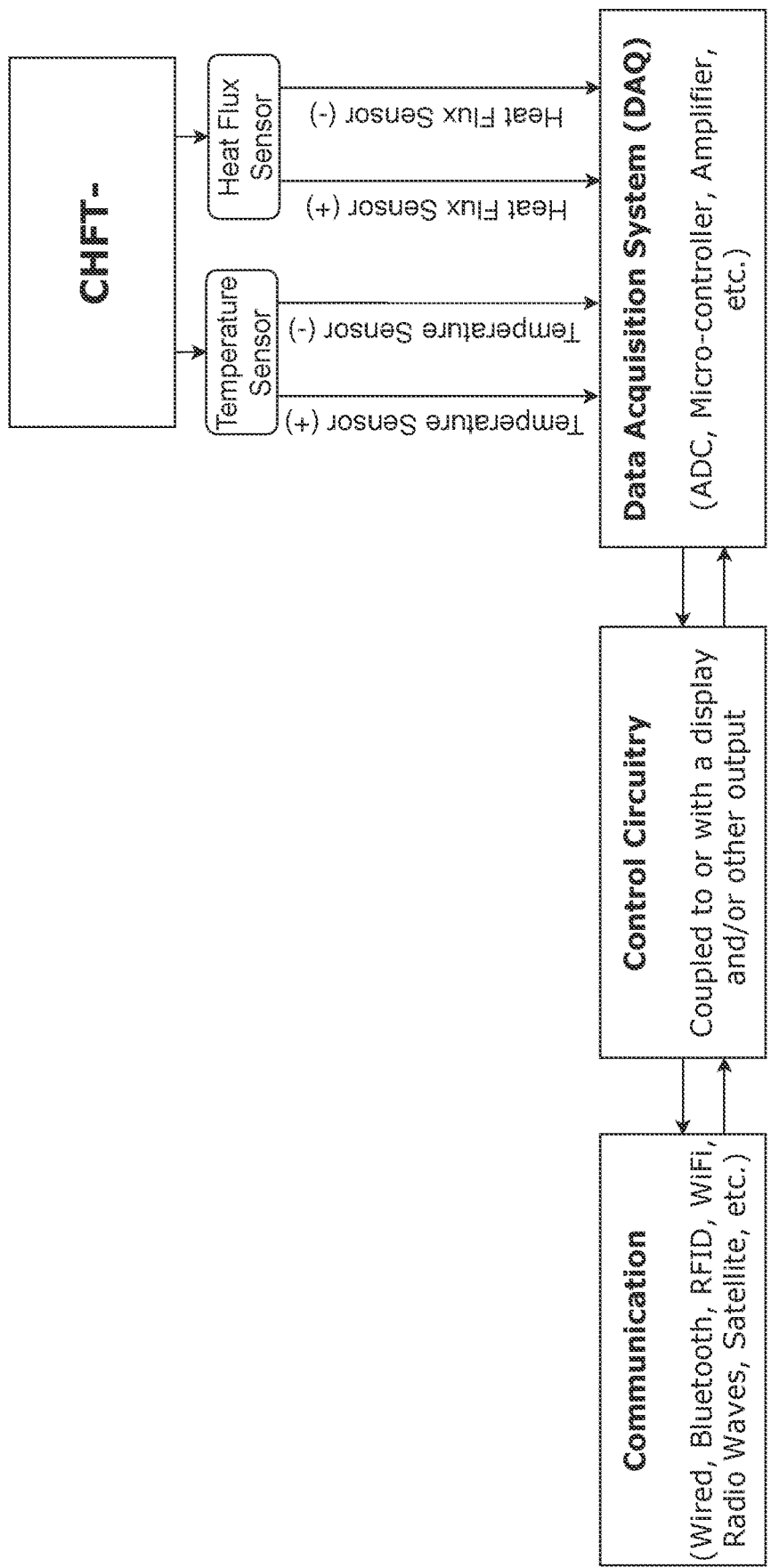
FIG. 8 is a function block diagram that illustrates an example NITI system to perform NITI with a CHFT−.

System Embodiments with One or More Heat Flux Sensor-Temperature Sensor Pairs for Determining One or More Internal Properties of an Object FIG. 8 illustrates an example NITI system to perform NITI using the CHFT−. The CHFT− includes a temperature sensor and a heat flux sensor (i.e., a heat flux sensor-temperature sensor pair). In other example embodiments, the CHFT− may include more than one temperature sensor and/or more than one heat flux sensor (e.g., multiple heat flux sensor-temperature sensor pairs). The configuration of the temperature sensor and the heat flux sensor with respect to each other and the object may be, for example, as illustrated in any of FIGS. 5 and 6A-6C. Analog signal outputs from the temperature sensor and the heat flux sensor corresponding to measured temperature sensor and measured heat flux sensor analog signals are provided via suitable communication paths (e.g., electrical conductors) and converted to digital signals by data acquisition (DAQ) circuitry, which may include, for example, one or more analog-to-digital converters (ADCs), microcontrollers, etc. The DAQ circuitry provides measured temperature sensor and measured heat flux sensor digital signals via suitable communication paths (e.g., electrical conductors, radio signals, etc.) to control circuitry for processing as described in more detail below. The control circuitry may include one or more suitably configured computers, microprocessors, DSPs, FPGAs, or other data processors. Suitable configuration of the control circuitry may be implemented in hardware, in software, or a combination. The control circuitry includes or is in communication with an output such as a display, a network, a cloud computer system, a communications device like a cell phone, wearable technology, etc. The output may also be used for one or more control operations such as sensor enablement and disablement, remote monitoring, measurement start/stop, data logging, temperature control, energy control, system failure control, preventive maintenance control, diagnostics, system performance, data input, data display, analytics, etc.

Figure 9:
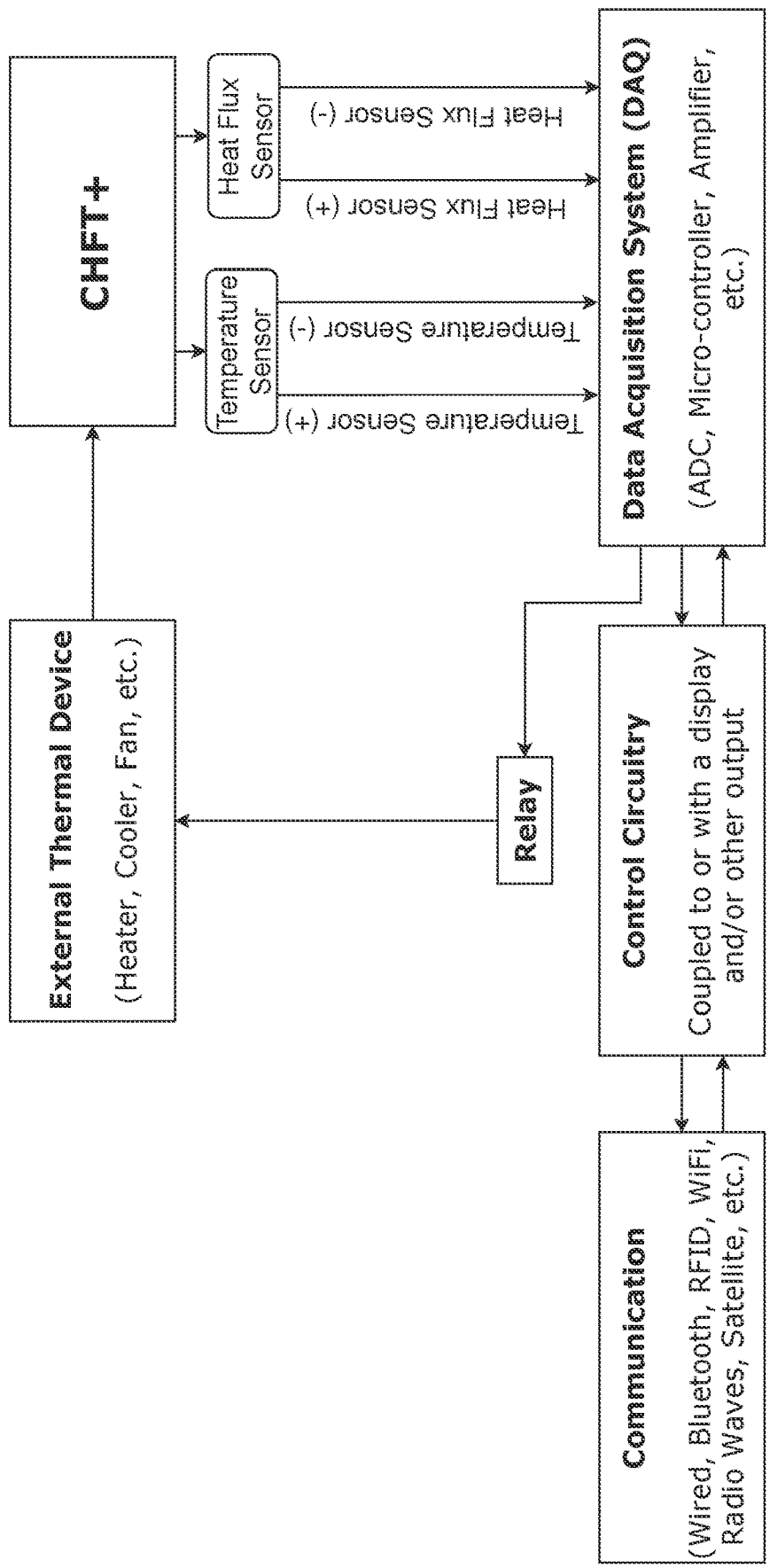
FIG. 9 is a function block diagram that illustrates an example NITI system to perform NITI with a CHFT+.

FIG. 9 illustrates an example NITI system to perform NITI with a CHFT+. Like the CHFT−, the CHFT+ includes a temperature sensor and a heat flux sensor (i.e., a heat flux sensor-temperature sensor pair). In other example embodiments, the CHFT+ may include more than one temperature sensor and/or more than one heat flux sensor (e.g., multiple heat flux sensor-temperature sensor pairs). In addition, the CHFT+ includes an external thermal device such as a resistive heater shown. The configuration of the temperature sensor, the heat flux sensor, and the external thermal device with respect to each other and the object may be, for example, as illustrated in any of FIGS. 7A-7G. In other example embodiments, the CHFT+ may include more than one external thermal device (e.g., a heater and a cooler). Analog signal outputs from the temperature sensor and the heat flux sensor corresponding to measured temperature sensor and measured heat flux sensor analog signals are provided via suitable communication paths (e.g., electrical conductors) and converted to digital signals by data acquisition (DAQ) circuitry, which may include, for example, one or more analog-to-digital converters (ADCs), microcontrollers, etc. The DAQ circuitry provides measured temperature sensor and measured heat flux sensor digital signals via suitable communication paths (e.g., electrical conductors, radio signals, etc.) to control circuitry for processing as described in more detail below. The control circuitry may include one or more suitably configured computers, microprocessors, DSPs, FPGAs, or other data processors. Suitable configuration of the control circuitry may be implemented in hardware, in software, or a combination. The control circuitry includes or is in communication with an output such as a display, a network, a cloud computer system, a communications device like a cell phone, wearable technology, etc. The output may also be used for one or more control operations such as sensor enablement and disablement, remote monitoring, measurement start/stop, external thermal device operation, data logging, temperature control, energy control, system failure control, preventive maintenance control, system performance, data input, data display, analytics, etc. In this non-limiting example, the external thermal device is controlled using a relay (an example switch), and the relay is operated by a relay signal from the DAQ which in turn provides the relay signal based on input from the control circuitry.

Figure 10:
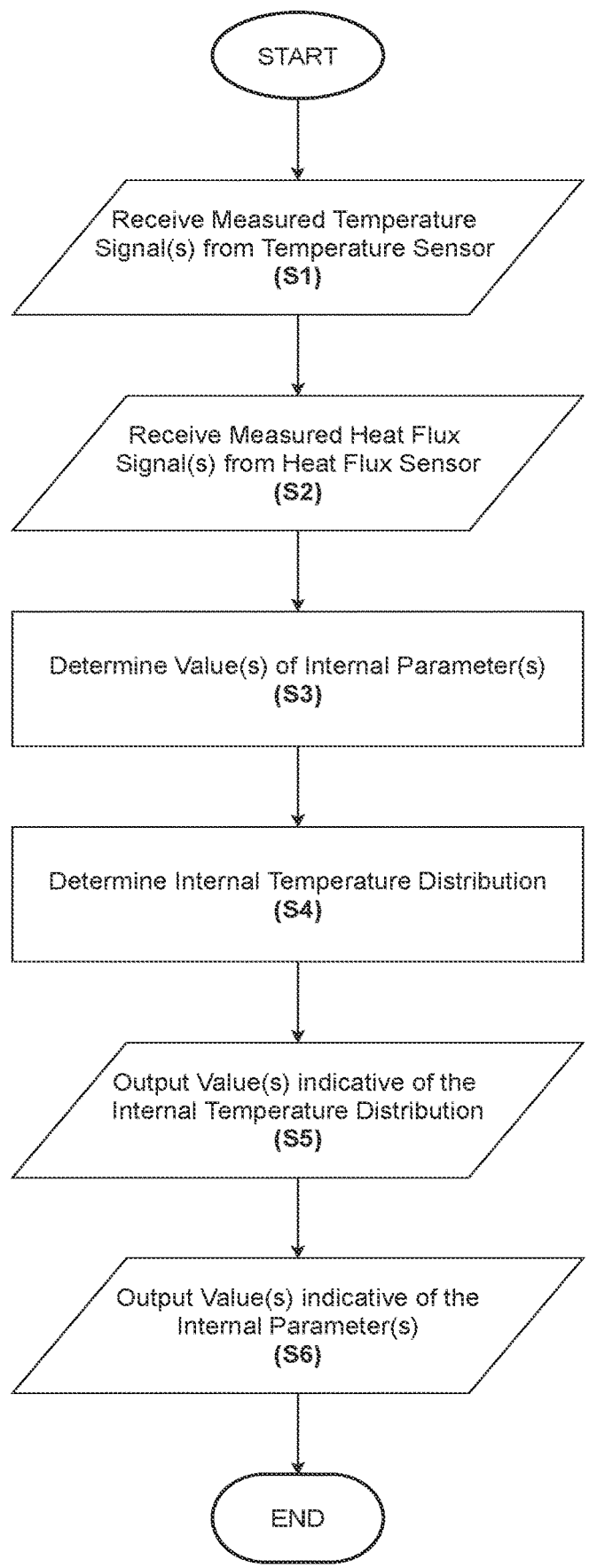
FIG. 10 is a flowchart outlining non-limiting example procedures performed by the control circuitry in an example NITI system that includes a NITI sensor for determining one or more internal properties of an object, including an internal temperature distribution of the object at one or more specified times using measured heat flux, measured temperature, and determined values of internal parameters of the object.

FIG. 10 is a flowchart outlining example procedures performed by the control circuitry in a non-limiting and example NITI system that includes a NITI sensor for determining one or more internal properties of an object, including an internal temperature distribution of the internal region of the object at one or more specified times using measured heat flux, measured temperature, and determined values of internal parameters of the object. A measured temperature signal is received by the control circuitry from the temperature sensor at one or more specified times (step S1). The control circuitry also receives a measured heat flux signal from the heat flux sensor measured at the one or more specified times to produce a measure of the heat transfer leaving or entering the object at the surface (step S2). The control circuitry determines values of the internal parameters at the one or more specified times in step S3 and determines an internal temperature distribution of the internal region of the object at the one or more specified times based on the measured temperature signal, the measured heat flux signal, and the values of the internal parameters in step S4. The control circuitry generates information (e.g., for output) indicating the internal temperature distribution at the one or more specified times (step S5). The control circuitry also generates information (e.g., for output) indicating one or more of the internal parameters at the one or more specified times in step S6. The control circuitry may optionally perform step S6 before step S5 and/or may optionally not perform step S4, step S5, and/or step S6. The control circuitry may optionally perform step S2 before step S1. In some example embodiments, the control circuitry may optionally perform step S3 before step S2 and/or step S1.

Additional procedures may be used in further example embodiments. For example, a thermal mathematical model (i.e., thermal model) of the object is determined and appropriate initial and boundary conditions are prescribed in order to solve for a thermal mathematical solution (i.e., mathematical solution). Thermal mathematical models and corresponding thermal mathematical solutions may be found in heat transfer literature for more general cases, while models for more unique cases may need to be derived and solved. A variety of methods for deriving and/or solving a thermal mathematical model may be used, including, but not limited to, analytical methods, finite difference methods, numerical methods, etc. Thermal mathematical models may be based on one-dimensional heat transfer or multi-dimensional heat transfer (e.g., two-dimensional).

For more accurate, robust, and consistent NITI, the boundary conditions of the thermal mathematical model are defined to include a surface heat flux boundary condition resulting in a thermal mathematical solution (e.g., internal temperature distribution) for the object with a heat flux input. A surface heat flux boundary condition can be used because the NITI sensor directly measures heat flux using, for example, a heat flux sensor at the object surface. Thus, heat flux can be directly used in the thermal mathematical model (i.e., heat flux boundary condition) which results in a heat flux input in the corresponding thermal mathematical solution (i.e., mathematical solution). Table 1 provides a detailed but still example one-dimensional thermal mathematical model (i.e., thermal model) which includes, a partial differential equation (PDE), appropriate boundary conditions, and an initial condition for a semi-infinite solid (i.e., semi-infinite medium), an example object and a general case in heat transfer literature.

TABLE 1

Thermal Model of a Semi-Infinite Solid with Heat Flux Boundary Condition

| | |
|---|---|
| PDE | $\frac{\partial T}{\partial t} = \alpha \frac{\partial^2 T}{\partial x^2}$ |
| Boundary Conditions | $-k \frac{\partial T}{\partial x} = q''_{Sensor}(t),$ <br> $x = 0$ <br> $T \to T_0, x \to \infty$ |
| Initial Condition | $T = T_0, t = 0$ | where:
k = thermal conductivity of the object
ρ = density of the object
C = specific heat capacity of the object
α = thermal diffusivity of the object
x = depth from object surface
t = time
T = internal temperature distribution of the object (a function of x and t)
$T_0$ = initial temperature of the object For a constant step heat flux input that occurs at the surface (x=0) of the semi-infinite medium (object), the mathematical solution of the thermal model in Table 1 is found as:

$$T(x, t) = T_0 + \frac{2q''_{Sensor,0}\left(\frac{\alpha t}{\pi}\right)^{\frac{1}{2}}}{k} \exp\left(\frac{-x^2}{4\alpha t}\right) - \frac{q''_{Sensor,0} x}{k} \mathrm{erfc}\left(\frac{x}{2\sqrt{\alpha t}}\right) \quad [2]$$

where $q_{Sensor,0}''$ is the constant step heat flux input at the boundary.

Using the Duhamel Method of Superposition (an example mathematical method), Equation [2] can be derived for heat flux inputs that change with time which is realistic of NITI sensor output:

$$T_m(x, t_m) = T_0 + \sum_{j=1}^{m} \left(q''_{Sensor,j} - q''_{Sensor,j-1}\right) \quad [3]$$

$$\left(\frac{2\left(\frac{\alpha(t_m - t_{j-1})}{\pi}\right)^{\frac{1}{2}}}{k} \exp\left(\frac{-x^2}{4\alpha(t_m - t_{j-1})}\right) - \frac{x}{k}\mathrm{erfc}\left(\frac{x}{2\sqrt{\alpha(t_m - t_{j-1})}}\right)\right)$$

where m indicates the $m^{th}$ measurement made by the NITI sensor so that $T_m(x,t_m)$ refers to the internal temperature of the object at a depth of x and at the $m^{th}$ measurement which corresponds to a specified time ($t_m$).

In this example, Equation [3] represents the thermal mathematical solution, i.e., the mathematical expression for the internal temperature distribution of the internal region of the object, for the non-limiting and example thermal model specified in Table 1.

Evaluating Equation [3] at the surface (x=0) and realizing that $$\alpha = \frac{k}{\rho C} : T_{Surface} = \qquad [4]$$

$$T_{Surface,0} + \sum_{j=1}^{m} \left( q''_{Sensor,j} - q''_{Sensor,j-1} \right) \times \sqrt{t_m - t_{j-1}} \times \frac{2}{\sqrt{\pi}\sqrt{k\rho C}}$$

where $T_{Surface,m}$ is the calculated surface temperature of the example object modeled in Table 1. Note that in this example, Equation [4] is a function of the surface object temperature in steady-state conditions ($T_{Surface,0}$) and is determined, e.g., prior to or after a transient thermal event. Equation [4] is also a function of surface heat flux measurements at one or more specified times ($q''_{Sensor,m}$) and the square root of the product of object thermal conductivity (k), object density ($\rho$), and object specific heat capacity (C). This internal parameter of the object ($\sqrt{k\rho C}$) is commonly referred to as thermal inertia (i.e., thermal effusivity).

The calculated object surface temperature as determined in Equation [4] can be used with a data processing method that may include, for example, one or more parameter estimation schemes. For NITI sensor output values (i.e., heat flux and temperature) measured at one or more specified times, the data processing method may compare the measured sensor temperature against the calculated surface temperature as found, in this example, when using Equation [4]. Among other things, this allows for the determination of estimated values for the corresponding internal parameters of the object; in this case, the internal parameter of thermal inertia (i.e., thermal effusivity) of the object ($\sqrt{k\rho C}$).

In other data processing methods, estimated values for the internal parameters of, in this example, object thermal conductivity (k), object density ($\rho$), and object specific heat capacity (C) may be determined individually. For example, for the case presented above, predetermined values of density ($\rho$) and specific heat capacity (C) may be determined from reference materials such as a textbook or manufacture specification, allowing for a data processing method to determine an estimated value for thermal conductivity (k) based on the estimated value of thermal inertia (i.e., thermal effusivity) of the object (($\sqrt{k\rho C}$)) or k$\rho$C. In other examples, a different thermal mathematical model may be developed with a corresponding thermal mathematical solution that, as opposed to Equation [4], distinguishes between each individual internal parameter when evaluated at a depth (x) in the object (e.g., x=0). This would allow for the determination of estimated values for each individual internal parameter (e.g., k, $\rho$, C, etc.) when used with an appropriate data processing method. The control circuitry may also perform further steps to improve the accuracy and/or expand the applications of NITI sensor(s). For example, as mentioned prior, the measured sensor temperature is not the same as a measure of the actual surface temperature of the object (e.g., semi-infinite solid) due to the presence of thermal contact resistance ($R_C''$) between the temperature sensor and object surface. This causes a difference between the actual surface temperature of the object and the measured sensor temperature. Thermal contact resistance ($R_C''$) may result from materials that may be layered over the temperature sensor of a NITI sensor as well as how well it adheres to the object surface. The smoothness/roughness of the object surface can also affect the thermal contact resistance ($R_C''$) as well as the overall accuracy of NITI. Thus, a smooth surface may be preferred. Use of adhesives (e.g., thermal paste, pressure sensitive adhesives, etc.) to mount the sensor may also affect thermal contact resistance ($R_C''$). FIG. 4 illustrates thermal contact resistance ($R_C''$) as pertains to an example NITI embodiment.

Mathematically, the measured sensor temperature and actual surface temperature can be related by Equation [1], shown here in index form as:

$$T_{Surface,m} = T_{Sensor,m} - q''_{Sensor,m} \times R_C'' \qquad [5]$$

where heat flux is defined to be positive when entering the object.

In an electrical engineering analogy, thermal contact resistance ($R_C''$) may be modeled as a resistor and $q''_{Sensor,m}$ as current. Thus, as current ($q''_{Sensor,m}$) flows through the resistor ($R_C''$), a voltage drop (difference) is created. Here, the voltage difference is analogous to a temperature difference between the sensor (i.e., measured) and object (i.e., actual) surface temperatures.

In some cases, the thermal effects associated with materials used to mount the sensor may also need to be considered. For example, one or more effects associated with, for example, mounting material thermal conductivity (k), mounting material density ($\rho$), and mounting material specific heat capacity (C) may need to be included and accounted for in a thermal mathematical model used for NITI.

For more accurate NITI, the effects of thermal contact resistance ($R_C''$) should be taken into account. Using Equation [4] with Equation [5] produces an expression for calculated sensor temperature in Equation [6].

$$T_{Calculated,m} = T_{Sensor,0} - q''_{sensor,0} \times R_C'' + \qquad [6]$$

$$\sum_{j=1}^{m} \left( q''_{Sensor,j} - q''_{Sensor,j-1} \right) \times \sqrt{t_m - t_{j-1}} \times \frac{2}{\sqrt{\pi}\sqrt{k\rho c}} + q''_{sensor,m} \times R_C''$$

Instead of Equation [4], Equation [6] may be used in a data processing method and, for example, compared against the measured sensor temperature output from the NITI sensor in order to determine estimated values for one or more internal parameters of the object. One example and non-limiting method of doing this is to define an objective function for minimization in a parameter estimation scheme. An example objective function could be defined as the Root Mean Squared Error (RMSE) between the two different measures of sensor temperature using Equation [7].

$$RMSE = \sqrt{\frac{1}{M-1} \sum_{m=1}^{M-1} (T_{Sensor,m} - T_{Calculated,m})^2} \qquad [7]$$

where $$T_{Calculated,m} = T_{Surface,m} + q''_{Sensor,m} \times R_C'' \qquad [8]$$

Thus, Equation [7] can be rewritten as:

$$RMSE = \sqrt{\frac{1}{M-1} \sum_{m=1}^{M-1} \left( T_{Sensor,m} - \left( T_{Surface,m} + q''_{Sensor,m} \times R_C'' \right) \right)^2} \qquad [9]$$

where M is the total number of measurements made by the NITI sensor over a period of time (i.e., one or more specified times). It should be noted that, depending on the embodiment, m may not always begin at the value of 1 as shown in Equation [7] and Equation [9]. Similarly, the quantity M−1 may also differ depending on the embodiment. For example, M−1 could be replaced by M−15 or M. In other example embodiments, M−1 may be replaced by m+30, m+10, m+5, etc. which defines the objective function for a specified number of measurements after the Mt h measurement.

In other data processing methods, a formulation based on the derivative of the objective function (e.g., Equation [9]) may be, for example, set equal to zero. The values of corresponding internal parameters and thermal contact resistance ($R_C''$) that best satisfy this condition are the determined estimated values.

As iterated prior, a major component of accurate and practical NITI is thermal contact resistance ($R_C''$) determination. For some cases, for example, low heat flux environments (e.g., zero heat-flux conditions) or otherwise negligible thermal contact resistance ($R_C''$) conditions, the thermal contact resistance ($R_C''$) may be ignored or otherwise determined to have an estimated value of zero. But for many cases, this is not an accurate assumption. In these cases, an estimated value for thermal contact resistance ($R_C''$) may, for example, need to be determined beforehand through previous measurement, determined as a part of a data processing method (e.g., via a parameter estimation scheme), or otherwise determined (e.g., predetermined by manufacture specification).

One way to determine an estimated value of thermal contact resistance ($R_C''$) is to include it as an unknown variable in a data processing method that may include a parameter estimation scheme. The combination of corresponding internal parameter values and thermal contact resistance ($R_C''$) value that generate the best match between the calculated sensor temperature and the measured sensor temperature, i.e., a least error, may be deemed to be the determined estimated values (i.e., optimal output values).

For example, for the general and example semi-infinite object case presented above, for each value attempted (e.g., guessed) for $\sqrt{k\rho C}$, an array of different $R_C''$ values is also attempted and input into Equation [6]. For each combination of attempted $\sqrt{k\rho C}$ and $R_C''$ values, the result of Equation [6] (i.e., calculated sensor temperature) is compared against the measured sensor temperature as output by the NITI sensor. This comparison can be conducted via, for example, an objective function such as the one defined in Equation [7]. In this example, the combination of values attempted for the internal parameters (e.g., $\sqrt{k\rho C}$) and thermal contact resistance ($R_C''$) that generate the best match between the calculated sensor temperature and the measured sensor temperature, i.e., a least error (e.g., least RMSE value), may be deemed to be the determined estimated values (i.e., optimal output values). However, this example approach (i.e., a brute force data processing method) may be time consuming, especially when more accurate results are desired. Consequently, this approach makes a majority of NITI applications impractical. Although time consuming, this technique is more accurate and faster than a brute force data processing method that is based on a mathematical solution found using a temperature based boundary condition. This is a result of the complexities and limitations of temperature based boundary conditions.

Another approach is to determine estimated values of the corresponding internal parameters (e.g., $\sqrt{k\rho C}$) and the thermal contact resistance ($R_C''$) value via an optimization scheme. For example, an optimization scheme may be designed to minimize the objective function (e.g., Equation [7]) by, for example, non-linearly varying combinations of the internal parameter values (e.g., $\sqrt{k\rho C}$) and the thermal contact resistance ($R_C''$) value. This approach could yield faster results when compared to the brute force data processing method described above but may not be as accurate.

A novel approach to determine an estimated value for thermal contact resistance ($R_C''$) is to determine (e.g., calculate) it based on the internal properties of the object. This significantly reduces processing time and makes the technology more practical for many applications. This approach takes advantage of the thermal contact resistance ($R_C''$) being constant with respect to time. Thus, at any specified time or at any given measurement, the thermal contact resistance ($R_C''$) is equivalent to the thermal contact resistance ($R_C''$) at preceding or following specified times or measurements. Mathematically this can be expressed as:

$$R_C'' = R_{C_n}'' \qquad [10]$$

where n indicates the $n^{th}$ measurement made by the NITI sensor (total of N measurements during a period of time). Thus, for purposes of this non-limiting example, N=M. Furthermore, the quantity n may differ depending on the embodiment. For example, n could be replaced by n−1 or n+1.

Given this consistency, the thermal contact resistance ($R_C''$) at a specified time or measurement is equivalent to the average thermal contact resistance throughout the period of time for which measurements are being made and can be expressed as:

$$R_{C_n}'' = \frac{\sum_{n=1}^{N-1} R_{C_n}''}{N-1} \qquad [11]$$

Furthermore, Equation [5] can be rearranged as:

$$R_{C_n}'' = \frac{T_{Sensor,n} - T_{Surface,n}}{q_{Sensor,n}''} \qquad [12]$$

Combining Equation [10], Equation [11], and Equation [12] produces:

$$R_{C_n}'' = \frac{\sum_{n=1}^{N-1} \frac{T_{Sensor,n} - T_{Surface,n}}{q_{Sensor,n}''}}{N-1} \qquad [13]$$

With regard to the example data processing method described prior, inputting Equation [13] into Equation [9], an example objective function of a parameter estimation scheme, results in:

$$RMSE = \sqrt{\frac{1}{M-1} \sum_{m=1}^{M-1} \left( T_{Sensor,m} - \left( T_{Surface,m} + q_{Sensor,m}'' \times \frac{\sum_{n=1}^{N-1} \frac{T_{Sensor,n} - T_{Surface,n}}{q_{Sensor,n}''}}{N-1} \right) \right)^2} \qquad [14]$$

It should be noted that, depending on the example embodiment, n may not always begin at the value of 1 as shown in Equation [14]. Similarly, the quantity N−1 may also differ depending on the embodiment. For example, N−1 could be replaced by N−15 or N. In other example embodiments, N−1 may be replaced by n+30, n+10, n+5, etc. which defines Equation [13] for a specified number of measurements after the $n^{th}$ measurement.

Compared to Equation [9], this version of the example objective function in Equation [14] is largely independent of the thermal contact resistance ($R_C''$). The only term that is dependent on the thermal contact resistance ($R_C''$) is $T_{Surface,0}$ where, as a result of Equation [5], is defined as $T_{Sensor,0} - q_{Sensor,0}'' \times R_C''$. It should be noted that, in many cases, the quantity $q_{Sensor,0}'' \times R_C''$ may be negligible. In cases where it is not negligible, a better design is needed and the quantity $q_{Sensor,0}'' \times R_C''$ may need to be accounted for. An example method of achieving this is by attempting (e.g., guessing) an initial value for thermal contact resistance ($R_C''$) before conducting, in this data processing method example, a parameter estimation scheme. Regardless of the initial value attempted, the parameter estimation scheme will determine an accurate estimated value for thermal contact resistance ($R_C''$) as well as accurate estimated values for the internal parameters.

As a part of a data processing method, using Equation [14] as the objective function in a parameter estimation scheme greatly reduces the time needed to make NITI measurements. For comparable accuracy and using the same computer, the inventor determined that this data processing method may be completed in less than 1 second of processing time as compared to approximately 15 minutes when utilizing a data processing method based on the brute force approach described above for the same data set (75 seconds of data-1 HZ sampling frequency).

Finally, another non-obvious approach is to determine an estimated value for the thermal contact resistance ($R_C''$) based on the internal parameters and the overall steady-state thermal resistance ($R_{Total}''$) of a given object. A non-limiting example of this is described below for an example NITI application.

It should be noted that these approaches for thermal contact resistance ($R_C''$) determination are not limited to a specific data processing method and/or NITI technique. Instead, they can be used as general expressions and approaches for thermal contact resistance ($R_C''$) determination regardless of the data processing method being utilized for NITI and/or NITI application.

Figure 11:
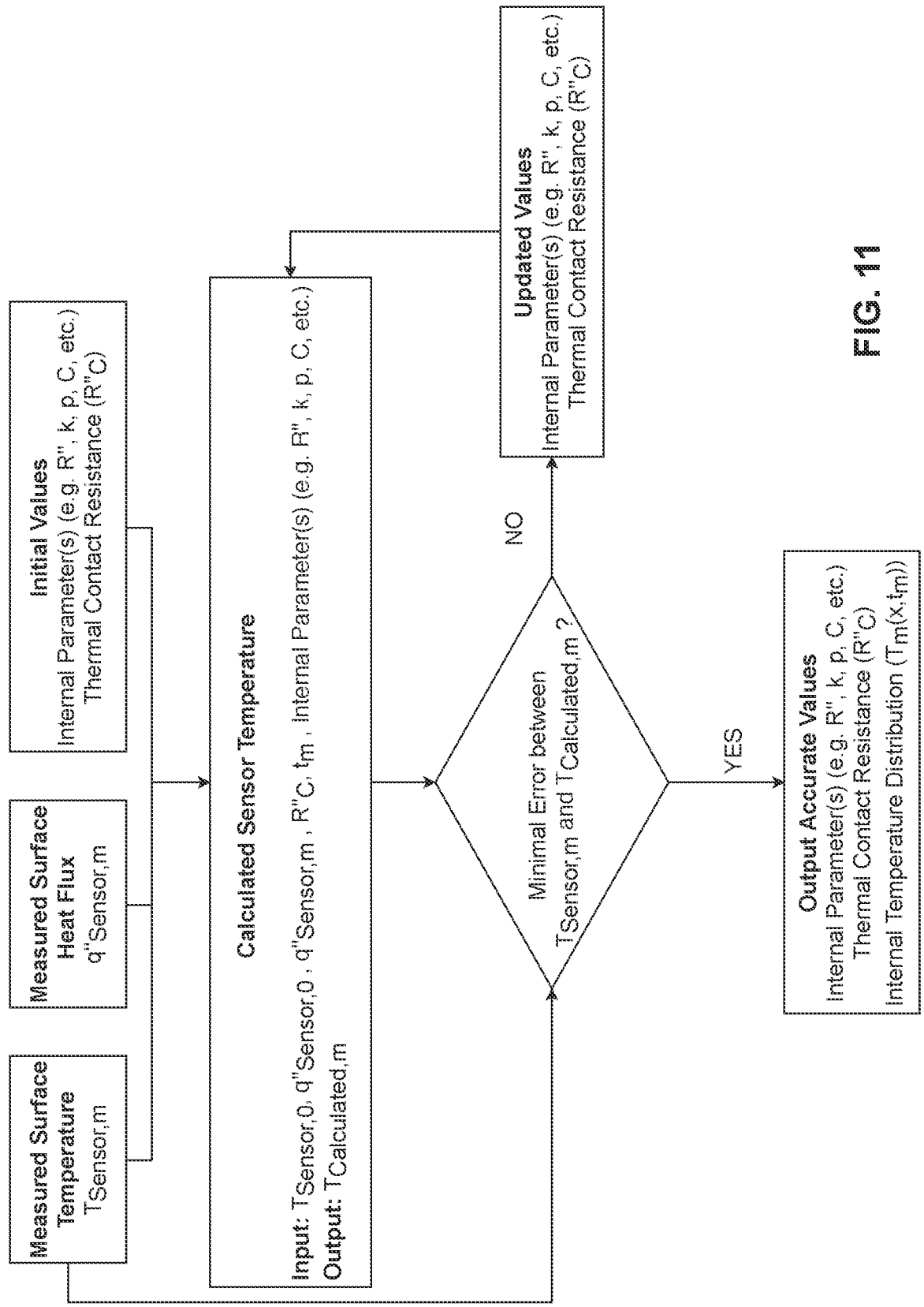
FIG. 11 is a flow diagram showing example procedures for a parameter estimation scheme performed by the control circuitry in a NITI system.

FIG. 11 is a flow diagram showing non-limiting example procedures for an example data processing method performed by the control circuitry in order to determine one or more internal properties of an object (i.e., internal properties) and an estimated thermal contact resistance ($R_C''$) between the object and NITI sensor surfaces. In this example, the data processing method includes a parameter estimation scheme. Measured surface temperature (i.e., measured sensor temperature) for the object at one or more specified times, measured surface heat flux for the object at the one or more specified times, initial values for one or more of the internal parameters of the object (e.g., R" (the steady-state thermal resistance of the object), k, ρ, C, $\sqrt{k\rho C}$, etc.) at the one or more specified times, and an initial value for the thermal contact resistance ($R_C''$) are input to a calculated sensor temperature equation (e.g., Equation [6]) to generate a calculated sensor temperature for the one or more specified times. In this example, a difference (e.g., error) is determined between the calculated sensor temperature for the one or more specified times and the measured sensor temperature for the one or more specified times. The difference is, for example, compared to a predetermined threshold and if greater than the threshold, then the difference is used to adjust one or more of the internal parameter values and thermal contact resistance ($R_C''$) value. For simplicity, the one or more adjusted internal parameter values and the one or more other (i.e., non-adjusted) internal parameter values are collectively referred to as updated values. Adjustment can be made in a number of different ways. For example, subsequent values of one or more of the internal parameters and the thermal contact resistance ($R_C''$) can be used without regard for any trends or patterns in the historical difference (e.g., error) resulting from the internal parameter and thermal contact resistance ($R_C''$) values used prior. In other examples, adjustments can be made based on the historical difference (e.g., error) resulting from the internal parameter and thermal contact resistance ($R_C''$) values used prior. In a non-limiting example, if a value of k (e.g., $k_0$) relates to a difference (i.e., error) of 100, and the next value, a greater value, used for k (e.g., $k_1$) relates to an error of 200, the control circuitry may attempt a value less than the original value of k ($k_0$) given the difference (i.e., error) increased when using a value greater than $k_0$ ($k_1$). Once the difference is less than or equal to the threshold or otherwise deemed minimal, the control circuitry deems the corresponding values used for the internal parameters and the thermal contact resistance ($R_C''$) to be accurate and optimal (i.e., output) estimated values. Then by using, for example, Equation [3], the control circuitry generates information (e.g., for output) corresponding to one or more accurate value(s) indicating the internal temperature distribution of the internal region of the object. Furthermore, if desired, the control circuitry generates information (e.g., for output) corresponding to accurate estimated value(s) indicating one or more of the internal parameters for the object such as R", k, ρ, C, $\sqrt{k\rho C}$, etc. and the thermal contact resistance ($R_C''$).

The approach just described is a non-limiting example periodic NITI data processing method performed by the control circuitry that may determine the internal parameters (e.g., R", k, ρ, C, $\sqrt{k\rho C}$, etc.) of the object, the thermal contact resistance ($R_C''$) between the temperature sensor and object surfaces, the internal temperature distribution of the internal region of the object (e.g., $T_m(x,t_m)$), etc. by post processing the heat flux and temperature signals output from a NITI sensor placed on the surface of the object and while may be subject to a thermal event. For the CHFT+, this thermal event can be generated by, for example, an external thermal device used with the control circuitry. While the CHFT− is designed to operate, for example, under external thermal event environments such as heat dissipation from the body, engine block heat loss, convective cooling or heating, etc. that are not used with the control circuitry. Because this procedure can be performed so quickly by the control circuitry, the data processing can be performed in real time as the heat flux and temperature signals are being measured and provided as inputs to the control circuitry. With each additional measurement, the data processing method is rerun, values for one or more of the internal properties of the internal region of the object (i.e., internal properties) are determined, and information for output, for example, is generated.

Other methods (i.e., techniques) of NITI may be performed by, for example, modifying the thermal mathematical solution (e.g., Equation [3]) to different forms depending on the internal properties of interest. Non-limiting examples of modified arrangements of thermal mathematical solutions and corresponding NITI methods are provided below for different applications. Each of these applications have corresponding thermal mathematical models. In general, depending on the NITI application and procedure used, different data processing methods may be utilized to determine estimated values for one or more internal properties of an object. Some of these methods may utilize parameter estimation schemes while others may not and instead, for example, be based on a calculation.

In other example embodiments, various mathematical operations may be performed on, for example, the thermal mathematical solution (e.g., derivate operations, integral operations, etc.) to determine (e.g., via a data processing method), one or more internal properties of an object.

System Embodiments with One or More Parallel Heat Flux Sensor-Temperature Sensor Pairs for Determining One or More Internal Properties of an Object Example NITI system embodiments that acquire object heat flux and temperature measurements in parallel by multiple (at least two) NITI sensors (e.g., CHFT+ or CHFT−) are referred to as DUO NITI embodiments. In addition to allowing for simpler and more robust NITI of objects, the DUO NITI embodiments eliminate uncertainties that may be associated with the non-limiting example NITI system embodiments and/or methods described above for the example CHFT+ and/or example CHFT− NITI system embodiments.

In order to make measurements in parallel, each NITI sensor in example DUO NITI embodiments may have different heat flux values detected by each heat flux sensor, corresponding to a difference in the amount of heat flux occurring at each NITI sensor location, also called a sensor node. This aspect of example DUO NITI embodiments is referred to as a differential heat flux environment. Example embodiments below may be used to achieve this condition. Typically, as a result of the differential heat flux environment, temperature measurements at each sensor node (i.e., node) also differ.

Figure 12:
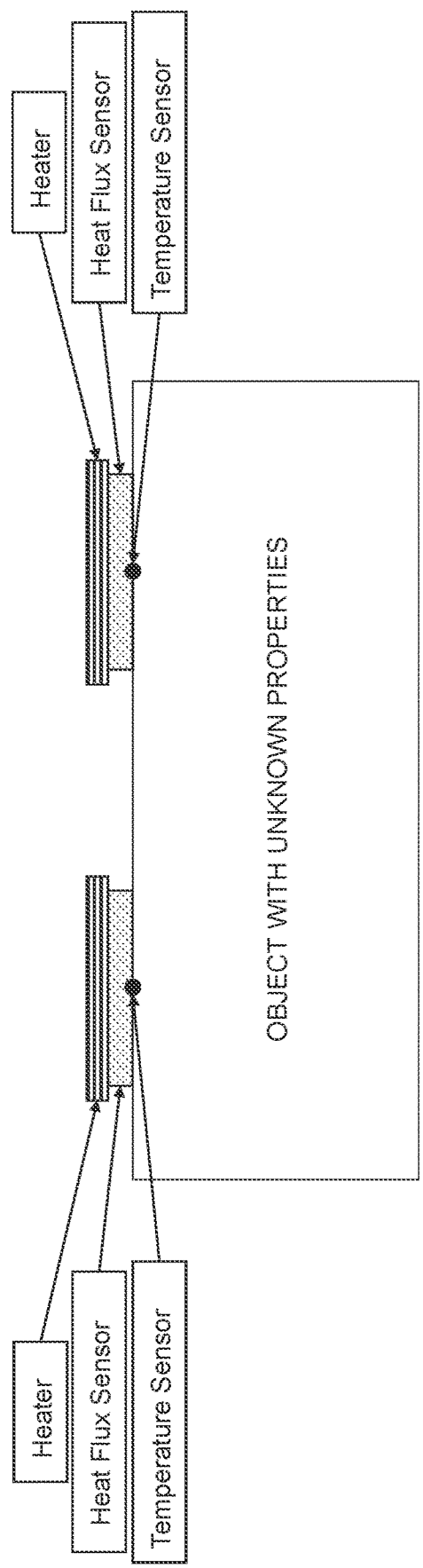
FIG. 12 shows a cross-section of an example DUO (parallel sensor pairs) CHFT+(with a heater) embodiment placed on a surface of an object with unknown internal properties.

One way to create a differential heat flux environment with an example DUO CHFT+ embodiment (multiple CHFT+ nodes) is to vary the amount of thermal energy each CHFT+ external thermal device (e.g., heater) provides. In the case of a heater, this can be achieved by, for example, differentiating the voltage provided to each heater, differentiating the electrical resistance of each heater, differentiating the power density of each heater, etc. to create the differential heat flux environment needed. FIG. 12 shows a cross-section of an example DUO (parallel NITI sensor nodes) CHFT+(with a heater) embodiment. In this example embodiment, each NITI sensor (i.e., sensor node or node) contains one heat flux sensor-temperature sensor pair and includes a heater (i.e., external thermal device) as a result of being CHFT+ nodes.

Figure 13:
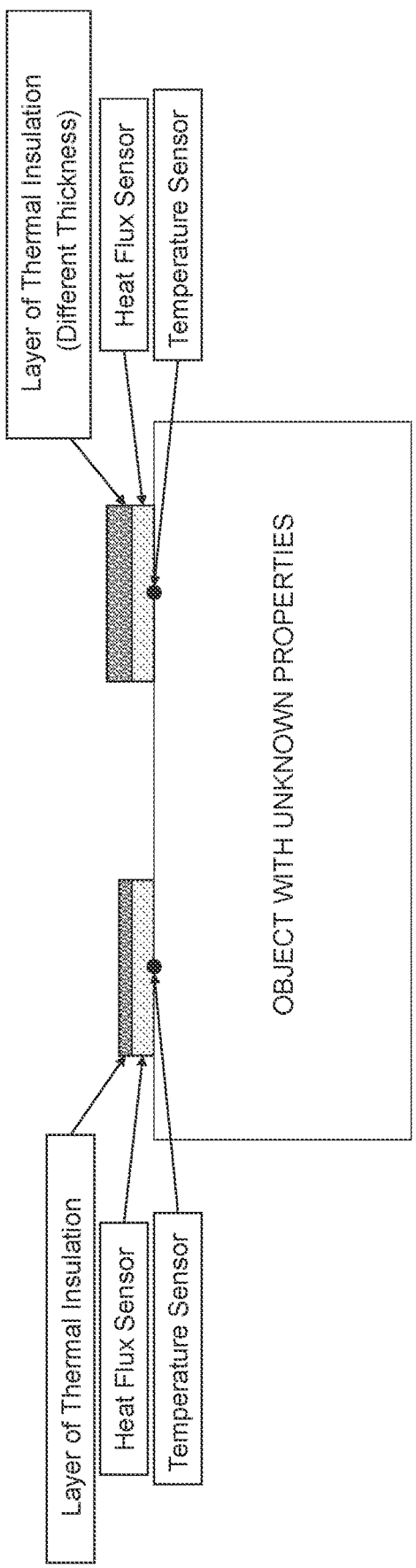
FIG. 13 shows a cross-section of an example DUO (parallel sensor pairs) CHFT− embodiment with different amounts of thermal insulation on each sensor node.

If an external thermal device (e.g., heater) is not an option, desired, or used, another way to create a differential heat flux environment is to place differing amounts of thermal insulation on each sensor node. The insulation can be used to control (i.e., limit, increase, etc.) the amount of heat flux occurring through the sensor node. Differing amounts of thermal insulation could be achieved via differing insulation thickness and/or materials. Thermal insulation may include metals or other thermally conductive materials designed to enhance and increase the amount of heat transfer occurring through the sensor node. Furthermore, the insulation may act as a filter and only allow substantive heat flux and temperature signals to be detected by the NITI sensor (e.g., CHFT+ or CHFT−). The insulation may also be used to protect the NITI sensor from external damage and/or external stimuli that may affect the quality of measurement. FIG. 13 shows a cross-section of an example DUO (parallel NITI sensor nodes) CHFT− embodiment with different amounts of thermal insulation on each sensor node to facilitate a differential heat flux environment. In NITI example embodiments, properties of the thermal insulation used at a sensor node do not need to be known, experimentally determined, or calibrated to make measurements of one or more object internal properties.

Figure 14:
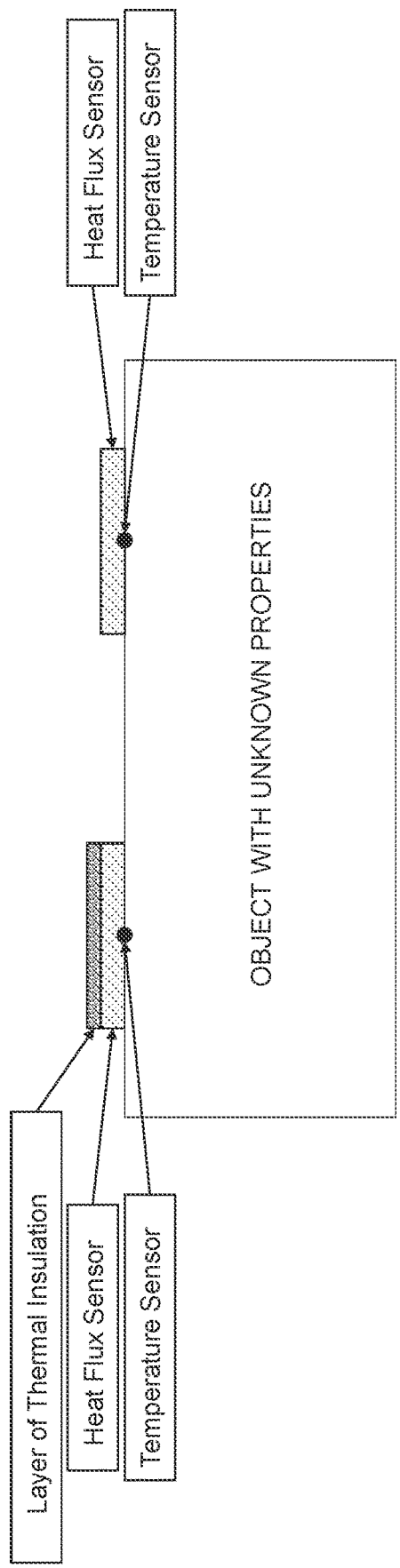
FIG. 14 shows a cross-section of an example DUO (parallel sensor pairs) CHFT− embodiment with one CHFT− node incorporating thermal insulation while the other is exposed.

Alternatively, for example when signal noise may not be an issue, one CHFT− node may incorporate thermal insulation while the other CHFT− node is exposed. The cross-section of this example embodiment is shown in FIG. 14.

Figure 15:
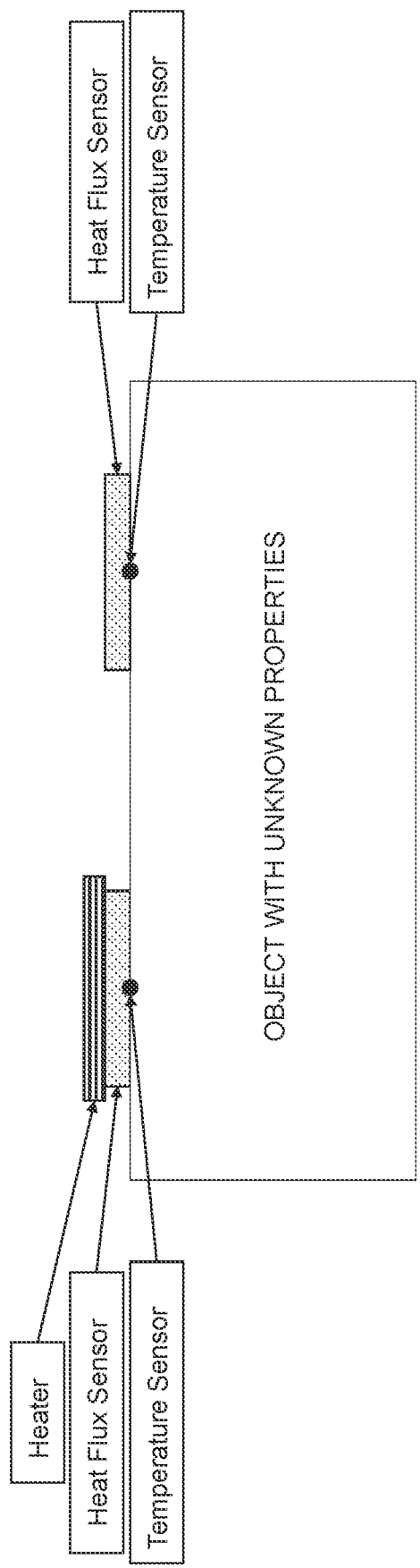
FIG. 15 shows a cross-section of an example DUO (parallel sensor nodes) CHFT+/− sensing embodiment where one sensor node incorporates a CHFT+ and one incorporates a CHFT−.

Another example embodiment in FIG. 15 shows the cross-section of a DUO CHFT+/− system where one sensor node incorporates a CHFT+ and one sensor node incorporates a CHFT−.

Figure 16:
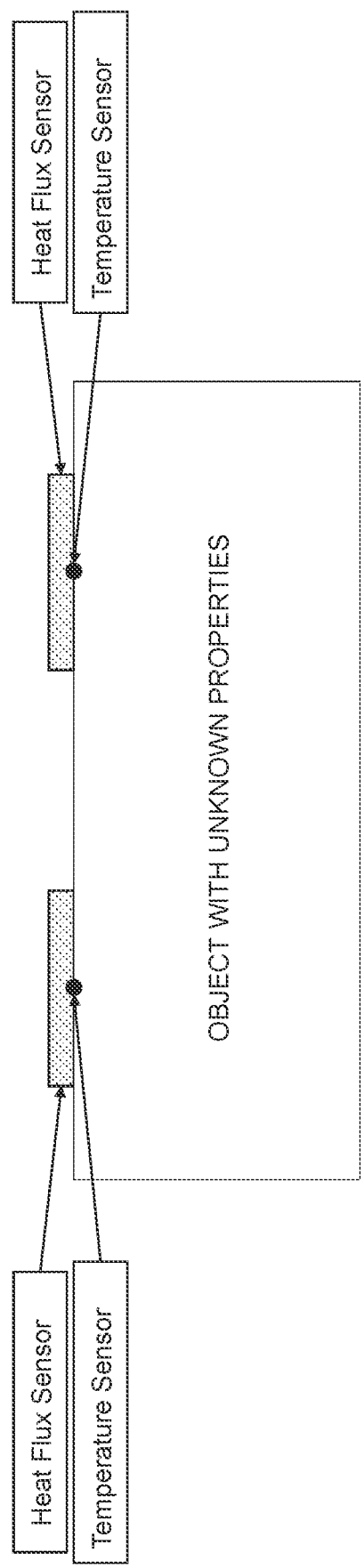
FIG. 16 shows a cross-section of an example DUO (parallel sensor pairs) CHFT− embodiment where neither sensor node has thermal insulation.

Still another example embodiment of a DUO CHFT− system cross-section is illustrated in FIG. 16. This example embodiment may be appropriate in cases where external thermal events are specific to individual sensor nodes. For example, one sensor node is heated with a lamp while another is cooled by a fan.

Another example embodiment in which a differential heat flux environment is created, includes using materials with different thermal resistance for each heat flux sensor-temperature sensor pair. For example, one sensor node incorporates an example NITI embodiment (e.g., CHFT−) made with materials of high thermal resistance and one sensor node incorporates an example NITI embodiment (e.g., CHFT−) made with materials of low thermal resistance. This difference in overall thermal resistance at each sensor node allows for a differential heat flux environment to be realized. Differing thermal resistance may be introduced into the example NITI embodiments, for example, by conductive or insulating vias/gaps within the one or more materials used to adhere, connect, house, and/or contact with the heat flux sensor and/or temperature sensor (e.g. rigid and/or flex printed circuit board, adhesives, substrates, etc.). In other example embodiments the heat flux sensor and/or temperature sensor of one sensor node may be manufactured using materials of low thermal conductivity and/or specified thickness while the heat flux sensor and/or temperature sensor of another sensor node may be manufactured using materials of high thermal conductivity and/or a different specified thickness.

As a result of the one or more parallel sensor nodes incorporated in example DUO NITI embodiments, innovative methods of signal measurement and data processing are possible in addition to performing the example CHFT+ and example CHFT− methods described above (where sensor nodes are independently operated). For purpose of demonstration, general, non-limiting, and example differential and quotient based data processing methods are now described for the DUO NITI system when operating in differential heat flux environments.

In this example, two NITI sensor nodes (i.e., sensor nodes) are modeled as being placed on a given object, where the internal properties of the object are, in this example, assumed to be uniform at the two sensor node locations. This results in the following example independent equations at each sensor node (nodes 1 and 2):

$$T_{Sensor1,m} - q''_{Sensor1,m} \times R''_{C1} = \quad [15]$$

$$T_{Internal} + R'' \times \left( q''_{Sensor1,0} + \sum_{j=1}^{m} \Delta q''_{Sensor1,j} \times \psi(t_m - t_{j-1}) \right)$$

$$T_{Sensor2,m} - q''_{Sensor2,m} \times R''_{C2} = \quad [16]$$

$$T_{Internal} + R'' \times \left( q''_{Sensor2,0} + \sum_{j=1}^{m} \Delta q''_{Sensor2,j} \times \psi(t_m - t_{j-1}) \right)$$

where $T_{Internal}$ is the internal temperature (i.e., internal temperature distribution) of the object, and $\psi$ is a response function that accounts for the transient heat transfer effects of the object at one or more specified times. Typically, p is derived for each thermal model independently and may be based on one or more internal parameters. Thus, it is typically unique to a given NITI application and corresponding thermal model. In some example DUO NITI embodiments, initial values for one or more of the internal parameters at one or more specified times may need to be determined for purposes related to the response function ($\psi$). These initial values may be predetermined (e.g., from a textbook, reference material, etc.), estimated (e.g., via a data processing method), or otherwise determined. In some example embodiments, the initial values are not changed and kept constant for the one or more specified times. In other example embodiments, the initial values may be updated or otherwise adjusted at one or more specified times.

In steady-state form, Equation [15] and Equation [16] reduce to:

$$T_{Sensor1,m} = T_{Internal,m} + q''_{Sensor1,m} \times (R'' + R''_{C1}) \quad [17]$$

$$T_{Sensor2,m} = T_{Internal,m} + q''_{Sensor2,m} \times (R'' + R''_{C2}) \quad [18]$$

Note that Equation [17] and Equation [18] do not include the response function ($\psi$) that accounts for the transient heat transfer effects of the object. Thus, they are typically not limited to specific NITI applications and corresponding thermal models.

A general and example differential based data processing method for the DUO NITI system includes determining the difference between Equation [15] and Equation [16] which results in:

$$(T_{Sensor1,m} - q''_{Sensor1,m} \times R''_{C1}) - (T_{Sensor2,m} - q''_{Sensor2,m} \times R''_{C2}) = \quad [19]$$

$$R'' \times \left( q''_{Sensor1,0} + \sum_{j=1}^{m} \Delta q''_{Sensor1,j} \times \psi(t_m - t_{j-1}) \right) -$$

$$R'' \times \left( q''_{Sensor2,0} + \sum_{j=1}^{m} \Delta q''_{Sensor2,j} \times \psi(t_m - t_{j-1}) \right)$$

Rearranging:

$$R'' = \frac{(T_{Sensor1,m} - q''_{Sensor1,m} \times R''_{C1}) - (T_{Sensor2,m} - q''_{Sensor2,m} \times R''_{C2})}{q''_{Sensor1,0} - q''_{Sensor2,0} + \sum_{j=1}^{m} \Delta q''_{Sensor1,j} \times \psi(t_m - t_{j-1}) - \sum_{j=1}^{m} \Delta q''_{Sensor2,j} \times \psi(t_m - t_{j-1})} \quad [20]$$

Equation [19] and Equation [20] represent example general forms of the DUO NITI system differential based data processing method where transient effects are accounted for and two sensor nodes are used in parallel. In steady-state conditions, Equation [20] reduces to:

$$T_{Sensor1,m} - T_{Sensor2,m} = q''_{Sensor1,m} \times (R'' + R''_{C1}) - q''_{Sensor2,m} \times (R'' + R''_{C2}) \quad [21]$$

Rearranging:

$$R'' = \frac{(T_{Sensor1,m} - q''_{Sensor1,m} \times R''_{C1}) - (T_{Sensor2,m} - q''_{Sensor2,m} \times R''_{C2})}{q''_{Sensor1,m} - q''_{Sensor2,m}} \quad [22]$$

In this example data processing method, when the thermal contact resistances at each sensor node ($R_{C1}''$ and $R_{C2}''$) are known, Equation [20] and Equation [22] can be used to determine the steady-state thermal resistance ($R''$) of the object which is based on, and thus, indicative of, the internal parameters of the object. Consequently, if desired, the steady-state thermal resistance ($R''$) of the object may be used to determine one or more internal parameters of the object when values are determined (e.g., predetermined, estimated, etc.) for one or more other internal parameters. Non-limiting examples of this are provided below.

If an estimated value for the thermal contact resistance at a sensor node ($R_{C1}''$ and/or $R_{C2}''$) is unknown, it can be determined (e.g., via the example CHFT+ or CHFT− procedures described above) or otherwise determined (e.g., using predetermined values).

When the thermal contact resistances at each sensor node ($R_{C1}''$ and $R_{C2}''$) are estimated to be negligible, Equation [20] reduces to:

$$R'' = \frac{T_{Sensor1,m} - T_{Sensor2,m}}{q''_{Sensor1,0} - q''_{Sensor2,0} + \sum_{j=1}^{m} \Delta q''_{Sensor1,j} \times \psi(t_m - t_{j-1}) - \sum_{j=1}^{m} \Delta q''_{Sensor2,j} \times \psi(t_m - t_{j-1})} \quad [23]$$

and Equation [22] reduces to:

$$R'' = \frac{T_{Sensor1,m} - T_{Sensor2,m}}{q''_{Sensor1,m} - q''_{Sensor2,m}} \quad [24]$$

When the thermal contact resistances at each sensor node are equal ($R_C'' = R_{C1}'' = R_{C2}''$), Equation [22] reduces to:

$$R''_{Total} = \frac{T_{Sensor1,m} - T_{Sensor2,m}}{q''_{Sensor1,m} - q''_{Sensor2,m}} \quad [25]$$

where $R''_{Total}$ is the total steady-state thermal resistance of the object and:

$$R''_{Total} = R'' + R_C'' \quad [26]$$

A general and example quotient based data processing method for the DUO NITI system includes determining the quotient between Equation [15] and Equation [16] which results in:

$$\frac{(T_{Sensor1,m} - q''_{Sensor1,m} \times R''_{C1}) - T_{Internal}}{(T_{Sensor2,m} - q''_{Sensor2,m} \times R''_{C2}) - T_{Internal}} = \quad [27]$$

$$\frac{(q''_{Sensor1,0} + \Sigma_{j=1}^{m} \Delta q''_{Sensor1,j} \times \psi(t_m - t_{j-1}))}{(q''_{Sensor2,0} + \Sigma_{j=1}^{m} \Delta q''_{Sensor2,j} \times \psi(t_m - t_{j-1}))}$$

Rearranging:

$$T_{internal,m} = \frac{\begin{array}{l}(T_{Sensor2,m} - q''_{Sensor2,m} \times R''_{C2}) \times \\ (q''_{Sensor1,0} + \Sigma_{j=1}^{m} \Delta q''_{Sensor1,j} \times \psi(t_m - t_{j-1})) - \\ (T_{Sensor1,m} - q''_{Sensor1,m} \times R''_{C1}) \times \\ (q''_{Sensor2,0} + \Sigma_{j=1}^{m} \Delta q''_{Sensor2,j} \times \psi(t_m - t_{j-1}))\end{array}}{\begin{array}{l}(q''_{Sensor1,0} + \Sigma_{j=1}^{m} \Delta q''_{Sensor1,j} \times \psi(t_m - t_{j-1})) - \\ (q''_{Sensor2,j} + \Sigma_{j=1}^{m} \Delta q''_{Sensor2,j} \times \psi(t_m - t_{j-1}))\end{array}} \quad [28]$$

Equation [27] and Equation [28] represent example general forms of the DUO NITI system quotient based data processing method where transient effects are accounted for and two sensor nodes are used in parallel. In steady-state conditions, Equation [27] reduces to:

$$\frac{(T_{Sensor1,m} - q''_{Sensor1,m} \times R''_{C1}) - T_{Internal}}{(T_{Sensor2,m} - q''_{Sensor2,m} \times R''_{C2}) - T_{Internal}} = \frac{q''_{Sensor1,m}}{q''_{Sensor2,m}} \quad [29]$$

Rearranging:

$$T_{Internal,m} = \frac{(T_{Sensor2,m} - q''_{Sensor2,m} \times R''_{C2}) \times q''_{Sensor1,m} - (T_{Sensor1,m} - q''_{Sensor1,m} \times R''_{C1}) \times q''_{Sensor2,m}}{q''_{Sensor1,m} - q''_{Sensor2,m}} \quad [30]$$

In this example data processing method, when the thermal contact resistances at each sensor node ($R_{C1}''$ and $R_{C2}''$) are known, Equation [28] and Equation [30] can be used to determine an internal temperature distribution ($T_{Internal,m}$) of the object. If an estimated value for the thermal contact resistance at a sensor node ($R_{C1}''$ and/or $R_{C2}''$) is unknown, it can be determined (e.g., via the example CHFT+ or CHFT− procedures described above) or otherwise determined (e.g., via predetermined values).

When the thermal contact resistances at each sensor node ($R_{C1}''$ and $R_{C2}''$) are estimated to be negligible, Equation [28] reduces to:

$$T_{Internal,m} = \frac{T_{Sensor2,m} \times (q''_{Sensor1,0} + \Sigma_{j=1}^{m} \Delta q''_{Sensor1,j} \times \psi(t_m - t_{j-1})) - T_{Sensor1,m} \times (q''_{Sensor2,0} + \Sigma_{j=1}^{m} \Delta q''_{Sensor2,j} \times \psi(t_m - t_{j-1}))}{(q''_{Sensor1,0} + \Sigma_{j=1}^{m} \Delta q''_{Sensor1,j} \times \psi(t_m - t_{j-1})) - (q''_{Sensor2,0} + \Sigma_{j=1}^{m} \Delta q''_{Sensor2,j} \times \psi(t_m - t_{j-1}))} \quad [31]$$

and Equation [30] reduces to:

$$T_{Internal,m} = \frac{T_{Sensor,m} \times q''_{Sensor1,m} - T_{Sensor1,m} \times q''_{Sensor2,m}}{q''_{Sensor1,m} - q''_{Sensor2,m}} \quad [32]$$

Equation [32] is also the form of Equation [30] when the thermal contact resistances at each sensor node are equal ($R_C'' = R_{C1}'' = R_{C2}''$).

As mentioned before, the non-limiting and example transient forms of, for example, the differential and quotient based data processing methods are typically unique to each NITI application and thermal model given the presence of the response function ($\psi$). However, the steady-state forms of, for example, the non-limiting and example differential and quotient based data processing methods are typically universal and applicable for almost any NITI application and corresponding thermal model.

Figure 17:
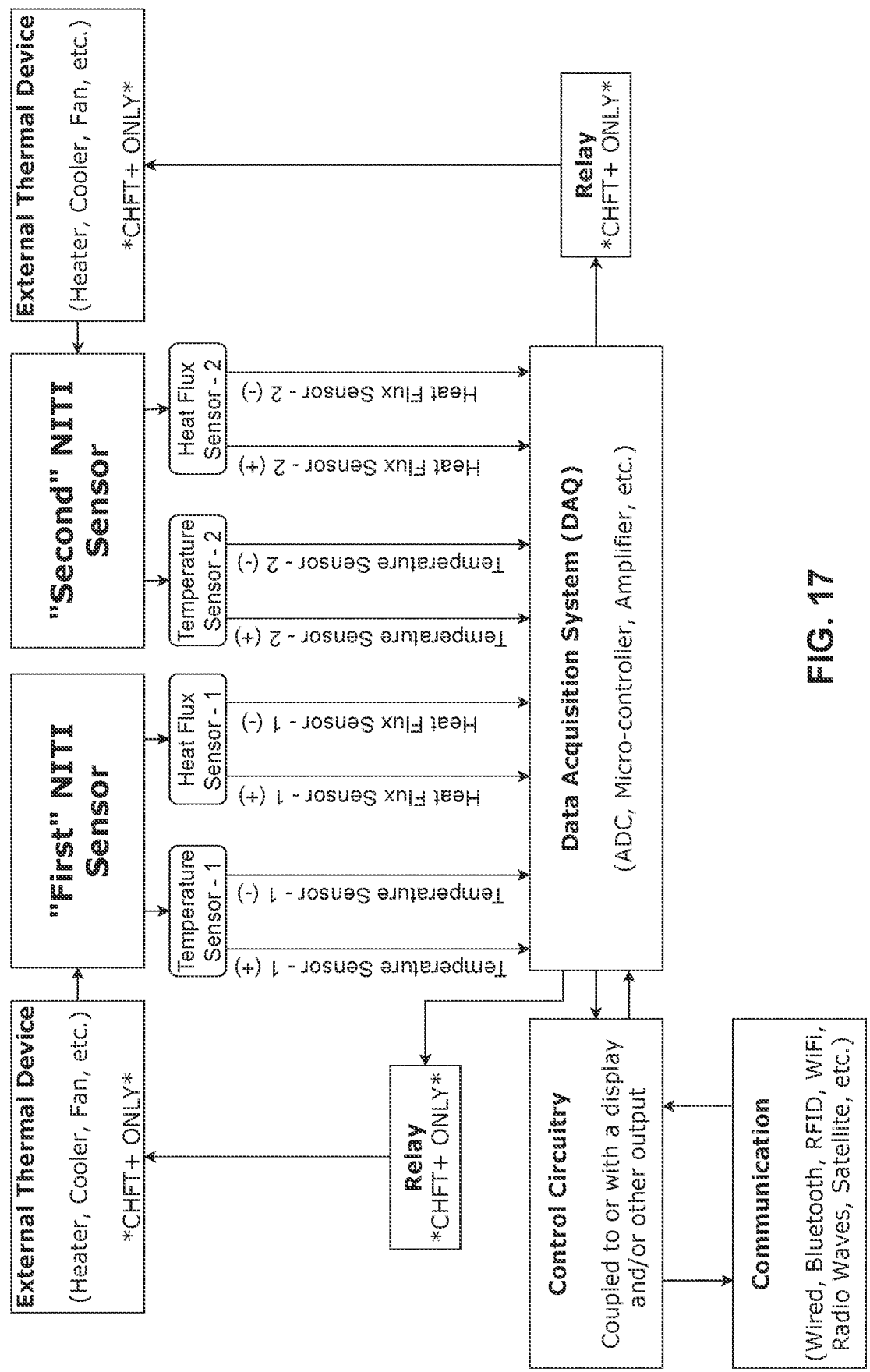
FIG. 17 is a function block diagram that illustrates an example NITI system to perform NITI with two non-invasive heat flux sensor-temperature sensor pairs operating in parallel for determining one or more internal properties of an object.

FIG. 17 illustrates an example NITI system to perform NITI with parallel heat flux sensor-temperature sensor pairs (i.e., DUO NITI system) for determining one or more internal properties of an object. Two NITI sensors (one is referred to as "first" and the other as "second" to distinguish them) are shown (although more than two NITI sensors may be used), and each NITI sensor (e.g., CHFT+ or CHFT−) includes a temperature sensor and a heat flux sensor (i.e., heat flux sensor-temperature sensor pair). In other example embodiments, each NITI sensor may include more than one temperature sensor and/or more than one heat flux sensor. The configuration of the temperature sensor and the heat flux sensor for each NITI sensor with respect to each other, to another NITI sensor, and the object may be as illustrated in any of the non-limiting examples shown in FIGS. 12-16. Analog signal outputs from the temperature sensor and the heat flux sensor corresponding to measured temperature sensor and measured heat flux sensor analog signals from each NITI sensor are provided via suitable communication paths (e.g., electrical conductors) and converted to digital signals by data acquisition (DAQ) circuitry, which may include, for example, one or more analog-to-digital converters (ADCs), microcontrollers, etc. The DAQ circuitry provides measured temperature sensor and measured heat flux sensor digital signals via suitable communication paths (e.g., electrical conductors, radio signals, etc.) to control circuitry for processing as described above and further below. The control circuitry may include one or more suitably configured computers, microprocessors, DSPs, FPGAs, or other data processors. Suitable configuration of the control circuitry may be implemented in hardware, in software, or a combination. The control circuitry includes or is in communication with an output such as a display, a network, a cloud computer system, a communications device like a cell phone, wearable technology, etc. The output may also be used for one or more control operations such as sensor enablement and disablement, remote monitoring, measurement start/stop, external thermal device operation, data logging, temperature control, energy flow control, system failure control, preventive maintenance control, diagnostics, system performance, data input, data display, analytics, etc. In this non-limiting example, when applicable (e.g., when using CHFT+ nodes), each external thermal device is controlled using a respective relay (i.e., switch), and the relay is operated by a relay signal from the DAQ which in turn provides the relay signal based on input from the control circuitry.

Figure 18A:
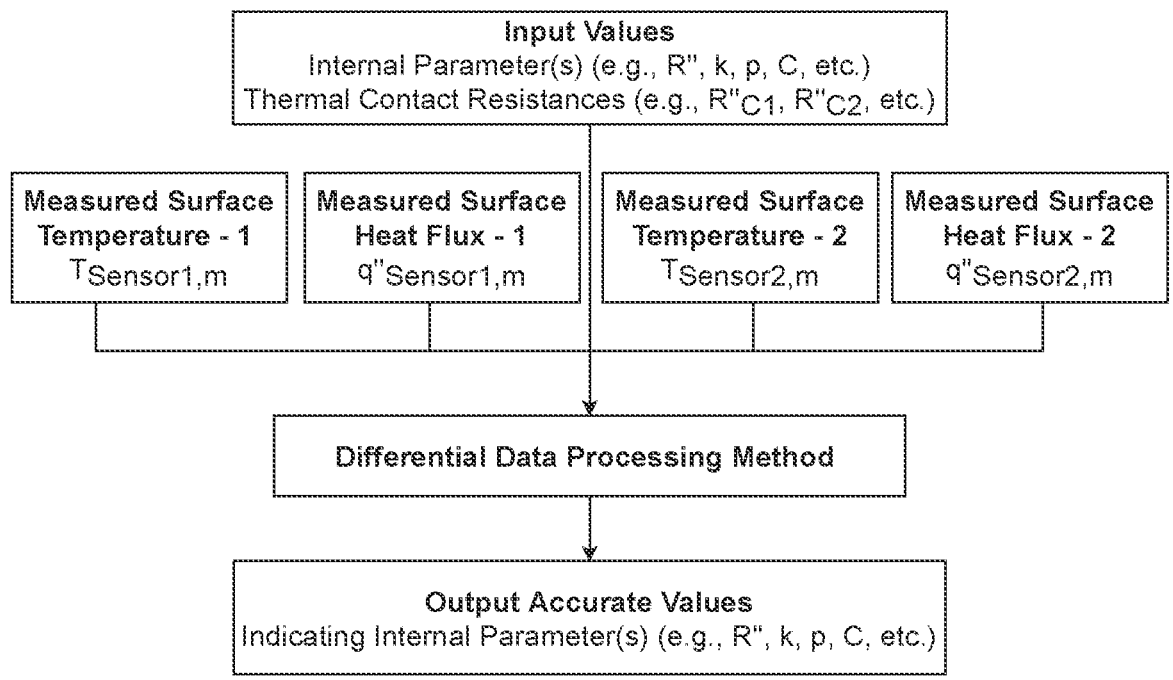
FIG. 18A is a flow diagram showing example procedures related to a differential based data processing method performed by the control circuitry.

FIG. 18A is a flow diagram showing example procedures for a differential based data processing method performed by the control circuitry in order to determine one or more internal parameters of an object (i.e., internal parameters) using two parallel NITI sensors (one is referred to as "first" and the other as "second" to distinguish them). Measured surface temperature at one or more specified times from the temperature sensor (i.e., measured sensor temperature) in each of the first and second NITI sensors and measured surface heat flux at the one or more specified times from the heat flux sensor in each of the first and second NITI sensors are input to the control circuitry. Initial values for one or more of the internal parameters (e.g., R", k, $\rho$, C, $\sqrt{k\rho C}$, etc.) at the one or more specified times and values for thermal contact resistance at each sensor node ($R_{C1}$" and $R_{C2}$") are also input to the control circuitry. The control circuitry then uses a differential based data processing method that determines, e.g., based on Equation [20], one or more of the internal parameters at the one or more specified times. Finally, the control circuitry generates information (e.g., for output) corresponding to one or more accurate value(s) indicating the internal parameters for the object such as R", k, $\rho$, C, $\sqrt{k\rho C}$, etc.

Figure 18B:
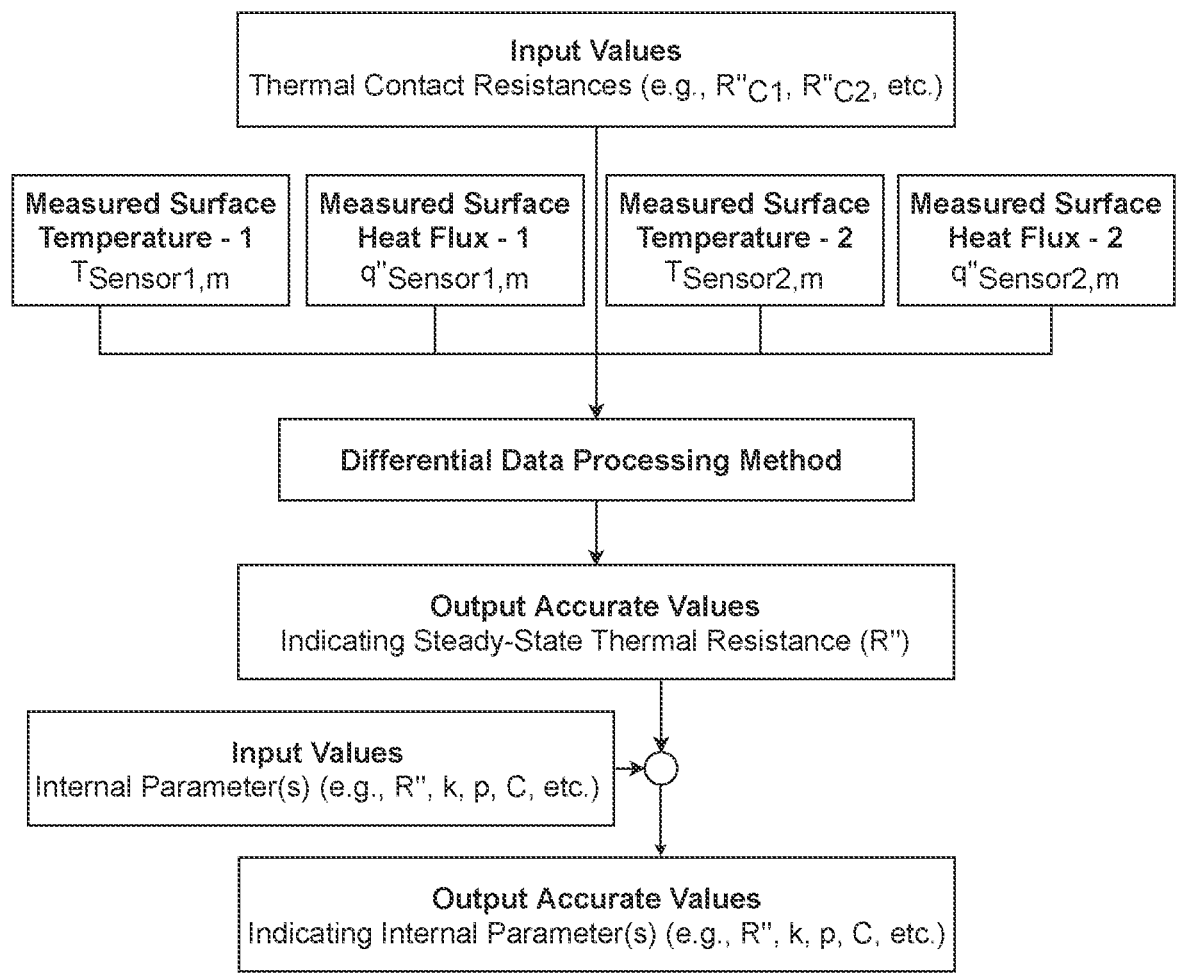
FIG. 18B is a flow diagram showing example procedures related to a differential based data processing method performed by the control circuitry in steady-state conditions.

FIG. 18B is a flow diagram showing example procedures for a differential based data processing method performed by the control circuitry in order to determine a steady-state thermal resistance of an object (an internal parameter) using two NITI sensors (one is referred to as "first" and the other as "second" to distinguish them) in steady-state conditions. Measured temperature at one or more specified times from the temperature sensor (i.e., measured sensor temperature) in each of the first and second NITI sensors and measured heat flux at the one or more specified times from the heat flux sensor in each of the first and second NITI sensors are input to the control circuitry. Values for thermal contact resistance at each sensor node ($R_{C1}$" and $R_{C2}$") are also input to the control circuitry. The control circuitry then uses a differential based data processing method that determines, e.g., based on Equation [22], a steady-state thermal resistance of the object (an internal parameter) at the one or more specified times. Finally, the control circuitry generates information (e.g., for output) corresponding to accurate values indicating the steady-state thermal resistance of the object. Furthermore, if desired, the control circuitry may generate information (e.g., for output) corresponding to one or more accurate values indicating one or more of the other internal parameters for the object such as k, $\rho$, C, $\sqrt{k\rho C}$, etc., based on the determined steady-state thermal resistance of the object and one or more determined (e.g., pre-determined, estimated, etc.) internal parameters.

Figure 19A:
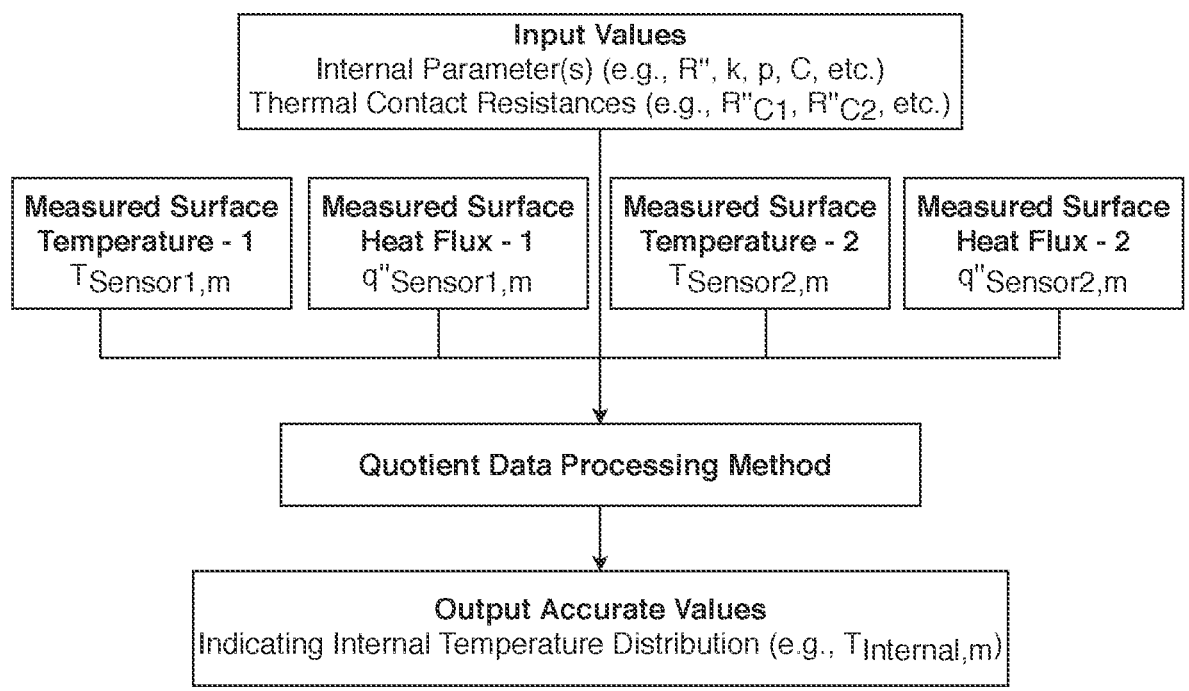
FIG. 19A is a flow diagram showing example procedures related to a quotient based data processing method performed by the control circuitry.

FIG. 19A is a flow diagram showing example procedures for a quotient based data processing method performed by the control circuitry in order to determine an internal temperature distribution of the internal region of an object (i.e., internal temperature distribution) using two parallel NITI sensors (one is referred to as "first" and the other as "second" to distinguish them). Measured temperature at one or more specified times from the temperature sensor (i.e., measured sensor temperature) in each of the first and second NITI sensors and measured heat flux at the one or more specified times from the heat flux sensor in each of the first and second NITI sensors are input to the control circuitry. Values for one or more internal parameters (e.g., R", k, $\rho$, C, $\sqrt{k\rho C}$, etc.) at the one or more specified times and values for thermal contact resistance at each sensor node ($R_{C1}$" and $R_{C2}$") and are also input to the control circuitry. The control circuitry then uses a quotient based data processing method that determines, e.g., based on Equation [30], the internal temperature distribution of the internal region of the object at the one or more specified times. Finally, the control circuitry generates information (e.g., for output) corresponding to one or more accurate values indicating the internal temperature distribution of the internal region of the object.

Figure 19B:
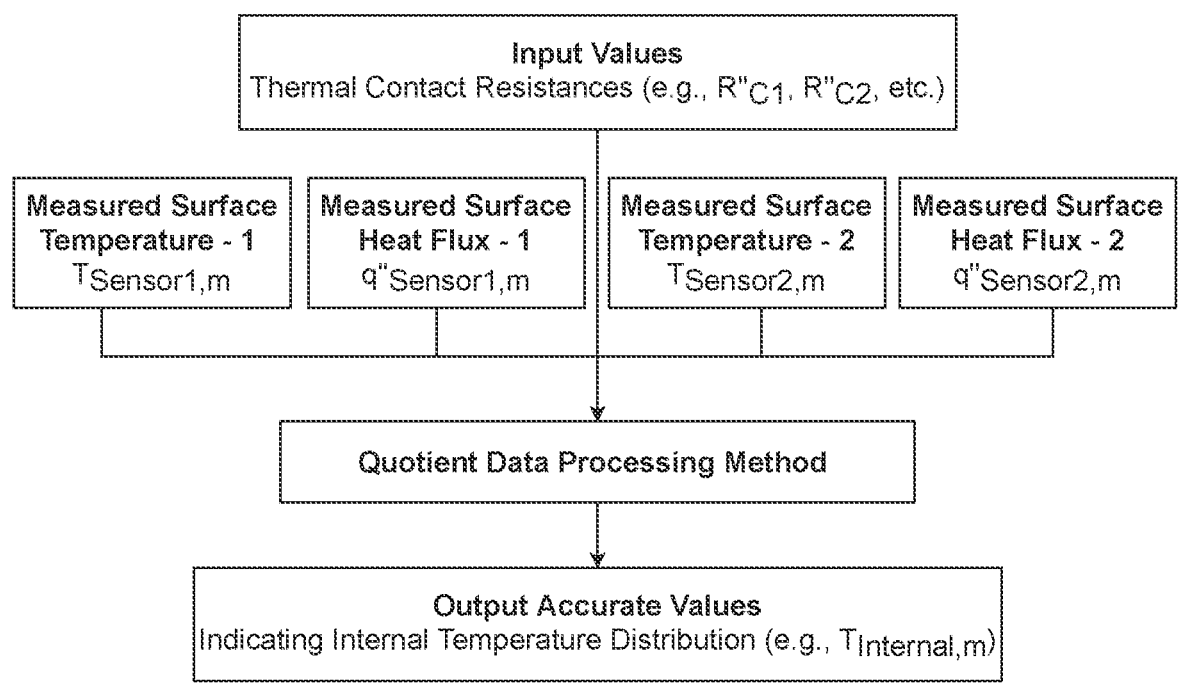
FIG. 19B is a flow diagram showing example procedures related to a quotient based data processing method performed by the control circuitry in steady-state conditions.

FIG. 19B is a flow diagram showing example procedures for a quotient based data processing method performed by the control circuitry in order to determine an internal temperature distribution of the internal region of an object (i.e., internal temperature distribution) using two parallel NITI sensors (one is referred to as "first" and the other as "second" to distinguish them) in steady-state conditions. Measured temperature at one or more specified times from the temperature sensor (i.e., measured sensor temperature) in each of the first and second NITI sensors and measured heat flux at the one or more specified times from the heat flux sensor in each of the first and second NITI sensors are input to the control circuitry. Values for thermal contact resistance at each sensor node ($R_{C1}$" and $R_{C2}$") are also input to the control circuitry. The control circuitry then uses a quotient based data processing method that determines, e.g., based on Equation [32], the internal temperature distribution of the internal region of the object at the one or more specified times. Finally, the control circuitry generates information (e.g., for output) corresponding to one or more accurate values indicating the internal temperature distribution of the internal region of the object.

Figure 20:
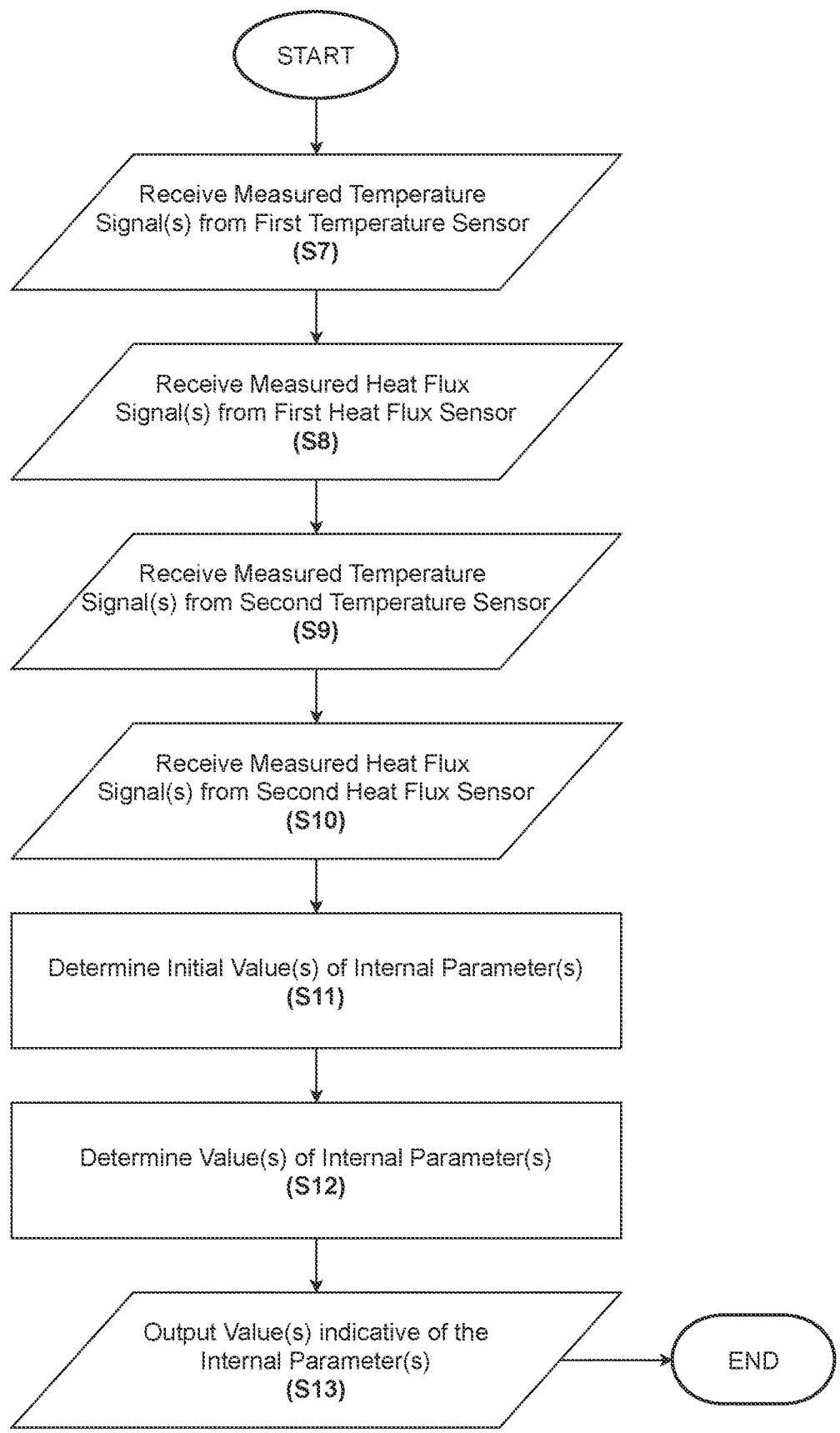
FIG. 20 is a flowchart outlining non-limiting example procedures for an example DUO NITI embodiment using two non-invasive heat flux sensor-temperature sensor pairs for determining one or more internal parameters of an object.

FIG. 20 is a flowchart outlining example procedures performed by the control circuitry in a non-limiting and example NITI system that includes a NITI sensor based on parallel NITI sensor nodes (i.e., DUO NITI system) and a differential based data processing method for determining one or more internal parameters of an object at one or more specified times. A first measured temperature signal is received by the control circuitry from the temperature sensor in a first non-invasive, heat flux sensor-temperature sensor pair at one or more specified times (step S7). A first measured heat flux signal is received by the control circuitry from the heat flux sensor in the first non-invasive, heat flux sensor-temperature sensor pair at the one or more specified times to determine a measure of the heat transfer leaving or entering the object at the surface at the one or more specified times (step S8). A second measured temperature signal is received by the control circuitry from the temperature sensor in the second non-invasive, heat flux sensor-temperature sensor pair at the one or more specified times (step S9). A second measured heat flux signal is received by the control circuitry from the heat flux sensor in the second non-invasive, heat flux sensor-temperature sensor pair measured at the one or more specified times to determine a measure of the heat transfer leaving or entering the object at the surface at the one or more specified times (step S10). The control circuitry determines initial values for each of the internal parameters at the one or more specified times (step S11). The control circuitry then determines one or more of the internal parameters of the object at the one or more specified times based on the measured temperature signals from the temperature sensors in the first and second non-invasive, heat flux sensor-temperature sensor pairs at the one or more specified times, the measured heat flux signals in the first and second non-invasive, heat flux sensor-temperature sensor pairs at the one or more specified times, and the initial values of the internal parameters at the one or more specified times (step S12). The control circuitry generates information (e.g., for output) indicating one or more of the internal parameters of the object at the one or more specified times (step S13). In subsequent procedures performed by the control circuitry (i.e., at one or more future specified times), the control circuitry may determine the initial values for one or more of the internal parameters in step S11 based on the values of one or more of the internal parameters determined in step S12 prior (i.e., at the one or more specified times). Additionally, the control circuitry may perform step S7 through step S11 in any order and is not limited to the order specified in this non-limiting example of procedures. In steady-state conditions, the control circuitry may optionally not perform step S11 and/or may not use initial values of the internal parameters in step S12. Furthermore, the control circuitry may also perform steps to determine and account for one or more effects associated with a thermal contact resistance between the temperature sensor in the first non-invasive, heat flux sensor-temperature sensor pair and the surface of the object and/or one or more effects associated with a thermal contact resistance between the temperature sensor in the second non-invasive, heat flux sensor-temperature sensor pair and the surface of the object.

Figure 21:
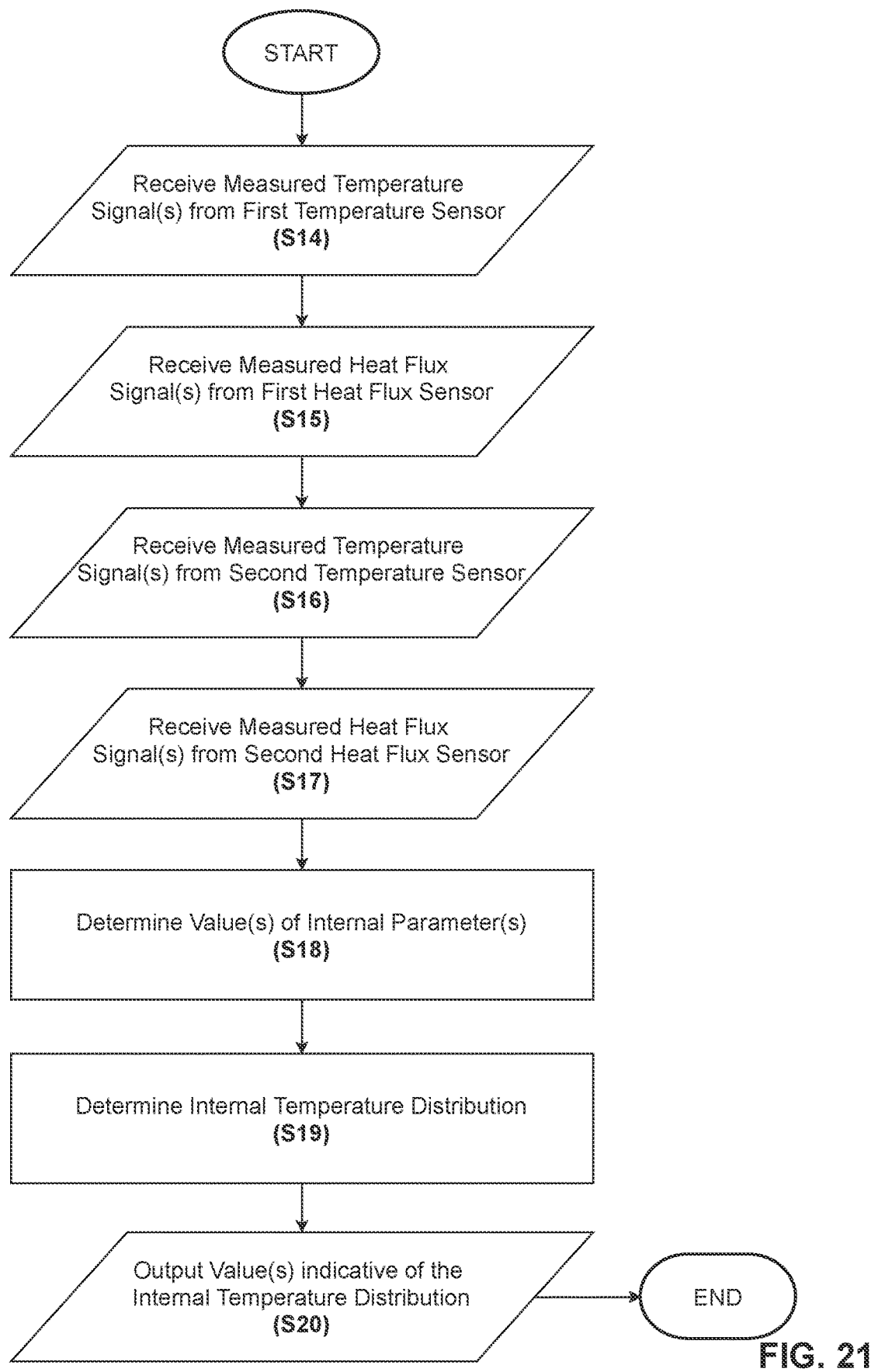
FIG. 21 is a flowchart outlining non-limiting example procedures for an example DUO NITI embodiment using two non-invasive heat flux sensor-temperature sensor pairs for determining an internal temperature distribution of an object.

FIG. 21 is a flowchart outlining example procedures performed by the control circuitry in a non-limiting and example NITI system that includes a NITI sensor based on parallel NITI sensor nodes (i.e., DUO NITI system) and a quotient based data processing method for determining an internal temperature distribution of the internal region of the object at one or more specified times. A first measured temperature signal is received by the control circuitry from the temperature sensor in a first non-invasive, heat flux sensor-temperature sensor pair at one or more specified times (step S14). A first measured heat flux signal is received by the control circuitry from the heat flux sensor in the first non-invasive, heat flux sensor-temperature sensor pair at the one or more specified times to determine a measure of the heat transfer leaving or entering the object at the surface at the one or more specified times (step S15). A second measured temperature signal is received by the control circuitry from the temperature sensor in the second non-invasive, heat flux sensor-temperature sensor pair at the one or more specified times (step S16). A second measured heat flux signal is received by the control circuitry from the heat flux sensor in the second non-invasive, heat flux sensor-temperature sensor pair measured at the one or more specified times to determine a measure of the heat transfer leaving or entering the object at the surface at the one or more specified times (step S17). The control circuitry determines values for each of the internal parameters at the one or more specified times (step S18). The control circuitry then determines the internal temperature distribution of the internal region of the object at the one or more specified times based on the measured temperature signals from the temperature sensors in the first and second non-invasive, heat flux sensor-temperature sensor pairs at the one or more specified times, the measured heat flux signals in the first and second non-invasive, heat flux sensor-temperature sensor pairs at the one or more specified times, and the values of the internal parameters at the one or more specified times (step S19). The control circuitry generates information (e.g., for output) indicating the internal temperature distribution of the internal region of the object at the one or more specified times (step S20). Additionally, the control circuitry may perform step S14 through step S18 in any order and is not limited to the order specified in this non-limiting example of procedures. In steady-state conditions, the control circuitry may optionally not perform step S18 and/or may not use values of the internal parameters in step S19. Furthermore, the control circuitry may also perform steps to determine and account for one or more effects associated with a thermal contact resistance between the temperature sensor in the first non-invasive, heat flux sensor-temperature sensor pair and the surface of the object and/or one or more effects associated with a thermal contact resistance between the temperature sensor in the second non-invasive, heat flux sensor-temperature sensor pair and the surface of the object.

Further example procedures performed by the control circuitry in a non-limiting and example NITI system that includes a NITI sensor based on parallel NITI sensor nodes, may include more than one data processing method. For example, a NITI system may include both a differential based data processing method and a quotient based data processing method for determining (e.g., calculating) one or more internal parameters of an object and determining (e.g., calculating) an internal temperature distribution of the internal region of the object, respectively. The NITI system may, for example, perform the multiple data processing methods subsequently or simultaneously. In other example embodiments, a data processing method may be based on a combination of multiple data processing methods to determine one or more internal properties.

Example DUO NITI embodiments may utilize control circuitry to maintain prescribed heat flux and temperature conditions. For example, control circuitry can be used to maintain steady-state conditions by adjusting the power supplied to an external thermal device (e.g., heater). In other example embodiments, the control circuitry can regulate the amount of heat flux and/or temperature occurring at one sensor node to be a constant multiple of the heat flux and/or temperature occurring at another sensor node.

Similar conditions may be further achieved without control circuitry. For example, a prescribed amount of thermal insulation on each sensor node may also be used to regulate the heat flux or temperature occurring at each sensor node to, for example, a constant multiple of another sensor node.

Creating such environments where the heat flux and/or temperature occurring at sensor nodes are related by, for example, a constant multiple (Y) allows for further simplification of DUO NITI systems and data processing methods.

For example, if control circuitry and/or thermal insulation is used to maintain the following relationship between the heat flux occurring at each sensor node:

$$Y \times q''_{Sensor1,m} = q''_{Sensor2,m} \qquad [33]$$

Equation [27] can be rewritten as:

$$\frac{(T_{Sensor1,m} - q''_{Sensor1,m} \times R''_{C1}) - T_{Internal}}{(T_{Sensor2,m} - Y \times q''_{Sensor1,m} \times R''_{C2}) - T_{Internal}} = \qquad [34]$$

$$\frac{(q''_{Sensor1,0} + \Sigma_{i=1}^{m} \Delta q''_{Sensor1,j} \times \psi(t_m - t_{j-1}))}{(Y \times q''_{Sensor1,0} + \Sigma_{i=1}^{m} Y \times \Delta q''_{Sensor1,j} \times \psi(t_m - t_{j-1}))}$$

which simplifies to:

$$T_{Internal,m} = \frac{Y \times (T_{Sensor1,m} - q''_{Sensor1,m} \times R''_{C1}) - (T_{Sensor2,m} - Y \times q''_{Sensor1,m} \times R''_{C2})}{(Y - 1)} \qquad [35]$$

Assuming negligible or equivalent thermal contact resistance ($R_C''$) at each sensor node:

$$T_{Internal,m} = \frac{Y \times T_{Sensor1,m} - T_{Sensor2,m}}{(Y-1)} \quad [36]$$

In this example, Equation [35] and Equation [36] can be used for simplified real-time internal temperature ($T_{Internal,m}$) measurement of a given object without any consideration for transient heat transfer effects (e.g., via a response function ($\psi$)) over time and/or internal parameters of the object.

Example Applications

Example embodiments are now described for different example applications and methods of NITI. Some of these examples have experimental data results included that are based on tests performed by the inventor. This is not meant to be an exhaustive list of applications or methods, but instead, illustrates examples of ways NITI can be used. Furthermore, example NITI methods are not limited to the applications and/or example embodiments listed below and may be used and/or the basis of other example NITI methods for different applications and/or example embodiments.

The experimental data results are based on example NITI sensor embodiments that include one or more heat flux sensors based on differential thermopile technology and one or more temperature sensors based on thin-film thermocouple technology. However, similar results may be obtained regardless of the type of heat flux sensors or temperature sensors (e.g., RTD temperature sensors, fiber optic temperature sensors, NTC temperature sensors, thermistors, thermopiles, etc.) used.

Blood Perfusion Measurement Application

Figure 22:
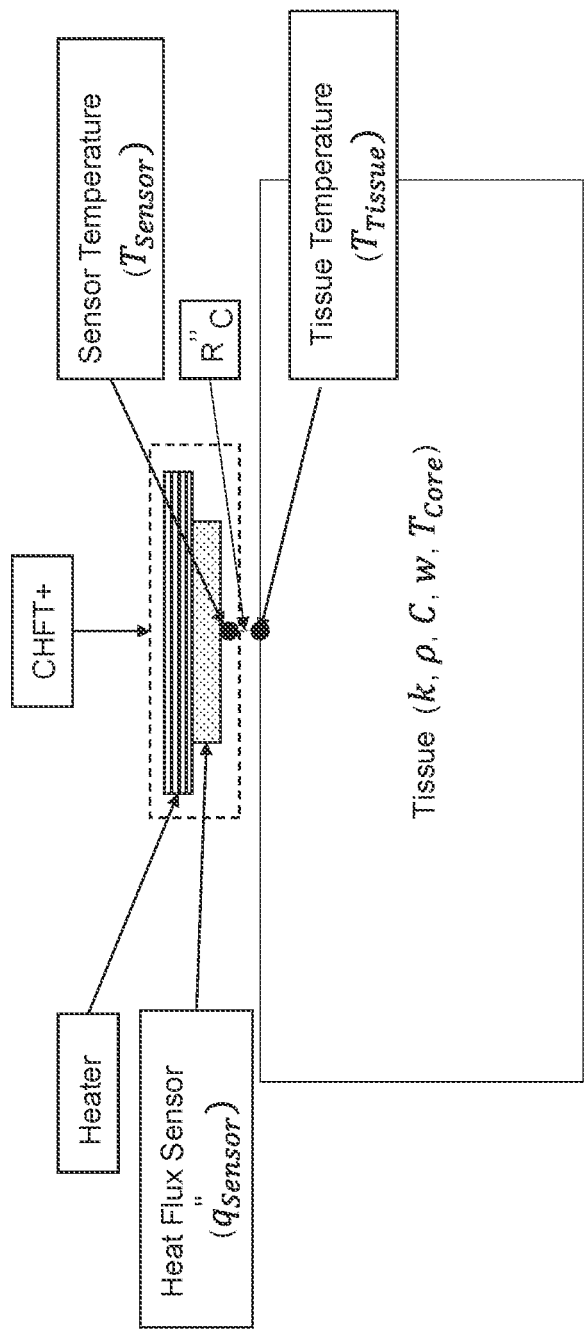
FIG. 22 shows an example application to blood perfusion (flow) in tissue.

One application is Blood Perfusion (Flow) in Tissue as shown in an example embodiment depicted in FIG. 22. A NITI sensor (CHFT+) is shown in contact with tissue. The tissue (i.e., object) includes multiple internal parameters including blood perfusion (w), tissue thermal conductivity (k), tissue density ($\rho$), and tissue heat capacity (C). As tissue depth (x) increases, the internal temperature distribution (T) of the tissue approaches the core blood temperature ($T_{Core}$). In this example application, the core blood temperature ($T_{Core}$) is assumed to be equal to (i.e., at thermal equilibrium with) the core tissue temperature given the majority of live tissue is composed of blood.

An example thermal mathematical model for bio-heat transfer which includes the effects of blood perfusion in tissue is set forth in Table 2 below.

TABLE 2

Thermal Mathematical Model for Tissue with Heat Flux Boundary Condition (based on Pennes Bio-Heat Equation)

| | |
|---|---|
| PDE | $\frac{\partial T}{\partial t} = \alpha \frac{\partial^2 T}{\partial x^2} - w(T - T_{Core})$ |
| Boundary Conditions | $-k \frac{\partial T}{\partial x} = q''_{Sensor}(t)$,<br>$x = 0$<br>$T \to T_{Core}$, $x \to \infty$ |
| Initial Condition | $T = T_{Initial}(x)$, $t = 0$ |

The solution of the thermal mathematical model in Table 2 (internal temperature distribution (T)), when evaluated at the tissue surface (x=0), is:

$$T_{Tissue,m} = T_{Tissue,0} + \sum_{j=1}^{m} \Delta q''_{Sensor,j} \times \frac{1}{k}\sqrt{\frac{\alpha}{w}} \times Erf\left(\sqrt{w(t_m - t_{j-1})}\right) \quad [37]$$

where the initial tissue surface temperature is:

$$T_{Tissue,0} = T_{Core} + q''_{Sensor,0} \times \frac{1}{k}\sqrt{\frac{\alpha}{w}} \quad [38]$$

and where heat flux is defined to be positive when entering the tissue.

Rewriting Equation [37] in terms of NITI sensor outputs and including effects of the thermal contact resistance ($R_C''$) between the NITI sensor and the tissue surfaces yields:

$$T_{Tissue,m} = \quad [39]$$
$$T_{Sensor,0} - q''_{Sensor,0} \times R_C'' + \sum_{j=1}^{m} \Delta q''_{Sensor,j} \times \frac{1}{k}\sqrt{\frac{\alpha}{w}} \times Erf\left(\sqrt{w(t_m - t_{j-1})}\right)$$

$$\text{where } \frac{1}{k}\sqrt{\frac{\alpha}{w}} = \sqrt{\frac{1}{k\rho Cw}}$$

is the steady-state thermal resistance (R") of tissue.

In this non-limiting example, the core blood temperature ($T_{Core}$) is assumed to be constant with time and unchanging. However, in cases where the core blood temperature ($T_{Core}$) is not constant, the effects may be distinguished from effects related to changes in the internal parameters (e.g., blood perfusion (w)). This is due to differences in the one or more effects resulting from such changes. For example, in some cases, effects related to changes in blood perfusion (w) can be realized via, for example, a surface temperature change that is the result of, in this example, a non-linear expression in Equation [39]. Effects related to changes in core blood temperature ($T_{Core}$), however can be realized, for example, via a surface temperature change that is the result of, in this example, a linear expression found in a combination of Equation [38] and Equation [39]. The differences in linear and non-linear effects allow for the distinction and differentiation between the different underlying causes (e.g., changes in the core blood temperature ($T_{Core}$) or the internal parameters). Furthermore, other thermal mathematical models may be derived to account for core blood temperature ($T_{Core}$) that varies over time as opposed to assuming core blood temperature ($T_{Core}$) to be constant, as in this non-limiting example.

Blood Perfusion—Periodic Measurements Using Parameter Estimation Embodiment

For an example NITI sensor embodiment (e.g., CHFT+ or CHFT−) used with a periodic data processing method, Equation [39] may be used in a parameter estimation scheme to determine the internal parameter of blood perfusion (w), core blood (i.e., tissue) temperature ($T_{Core}$), and/or the thermal contact resistance ($R_C''$) between the NITI sensor and the tissue surfaces. This is similar to the general case presented as an example in the NITI system embodiments with one or more heat flux sensor—temperature sensor pairs section above but with a different thermal model for a different NITI application. In this example, predetermined constant values for the internal parameters of tissue thermal conductivity (k), tissue density (ρ), and tissue heat capacity (C) are used. An example objective function to be minimized in this example application is:

$$RMSE = \sqrt{\frac{1}{M-1} \sum_{m=1}^{M-1} (T_{Sensor,m} - T_{Calculated,m})^2} \quad [40]$$

where:

$$T_{Calculated,m} = T_{Tissue,m} + q_{Sensor,m}'' \times R_C'' \quad [41]$$

and where:

$$R_C'' = \frac{\sum_{n=1}^{N-1} \frac{T_{Sensor,n} - T_{Tissue,n}}{q_{Sensor,n}''}}{N-1} \quad [42]$$

An example CHFT+ embodiment (with heater) was tested on a live tissue simulator capable of creating a controlled water perfusion and temperature environment in pseudo tissue. This simulator is called the phantom tissue system or phantom. At different flowrates (perfusion rates), the CHFT+ was placed on the pseudo tissue and measurements were made as follows:

10 seconds of steady-state data was recorded.

Heater turned on for approximately 65 seconds, resulting in a transient thermal response of the tissue as measured by the CHFT+ via surface heat flux and surface temperature signals.

The entirety of the data was processed via a periodic data processing method that included a parameter estimation scheme in less than 1 second, resulting in outputs of perfusion (w), core water temperature ($T_{Core}$), and the thermal contact resistance ($R_C''$) between the CHFT+ and the pseudo tissue surfaces.

when compared against the phantom model. Note that the unit of blood perfusion (w) is denoted as $ml_{B/S}/ml_T$ where a measure of blood flow rate (e.g., milliliters of blow flow per second) through a volume of tissue (e.g. millimeter of tissue) is provided. In these example embodiments tested on the Phantom Tissue System, blood perfusion is instead specified as perfusion and blood flow rate is instead water flow rate.

In some example embodiments, the unit of blood perfusion (w) may be further reduced to $s^{-1}$. In other example embodiments, the unit of blood perfusion (w) may be combined with a density value to provide a measure of blood flow rate through a given mass of tissue (e.g., 100 grams).

Furthermore, the estimated values for perfusion (w) increase as the flow rate increases. In addition, the thermal contact resistance ($R_C''$) is relatively constant which signifies its consistency throughout the experimental measurements, as expected. The estimated core temperature of the perfused water ($T_{Core}$) matches well with the perfusing water temperature ($T_{Water}$) recorded using a submerged bead thermocouple within the phantom. The greatest difference was about 0.24° C. occurring at 25 CC/min.

Figure 23:
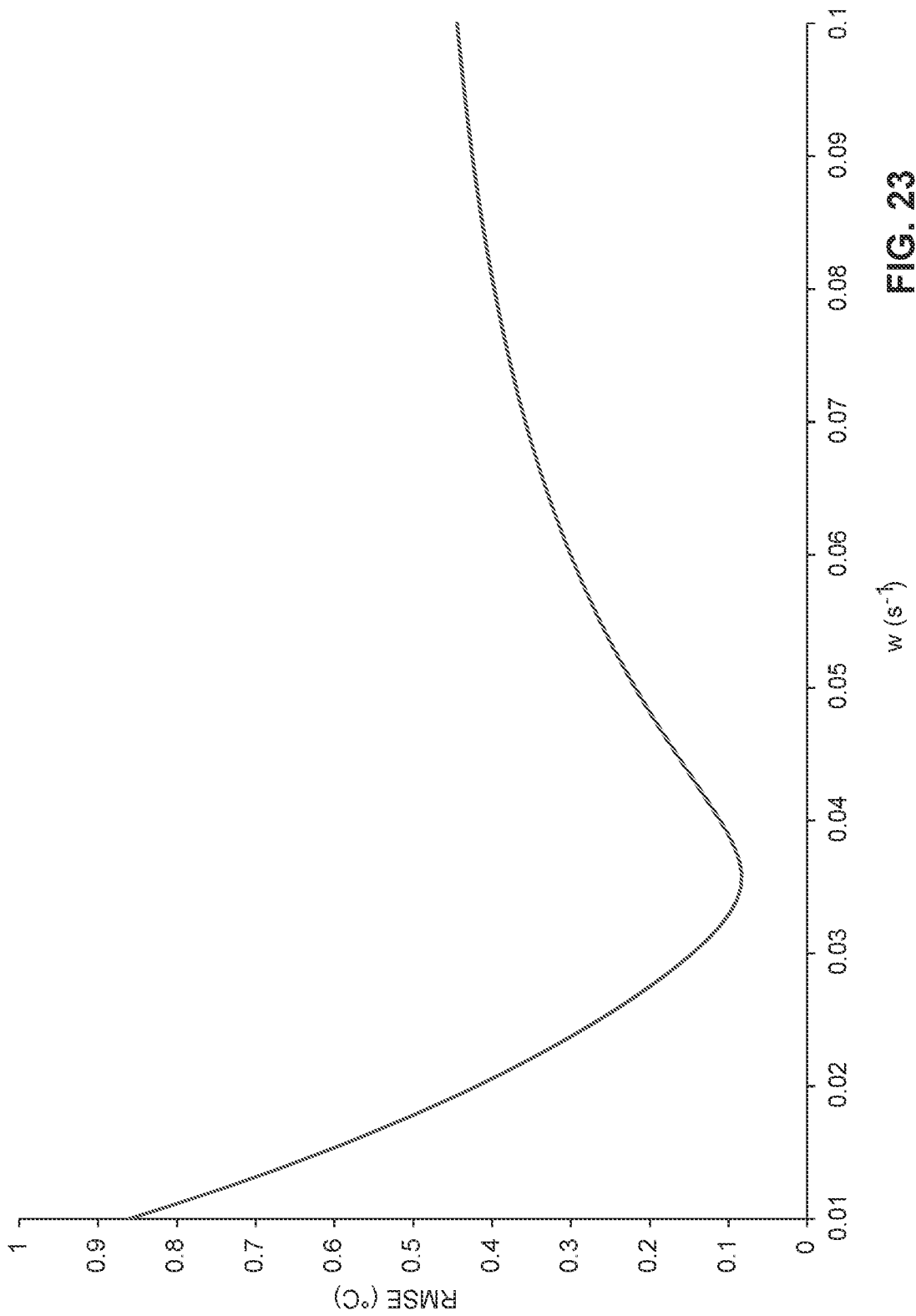
FIG. 23 is a graph that shows the parameter estimation scheme's ability to determine an optimal perfusion (w) value when used with experimental data.

In order to demonstrate the ability of the parameter estimation scheme used in this data processing method in determining an optimal perfusion (w) value when used with experimental data, the relationship between the example objective function in Equation [40] (i.e., RMSE) and perfusion (w) for the 15 CC/min case is displayed in FIG. 23. The graph in FIG. 23 illustrates that the relationship has a global minimum at the perfusion (w) value of 0.0360 s−1. This corresponds to the estimated value of perfusion for the 15 CC/min case, as documented in Table 3.

Figure 24:
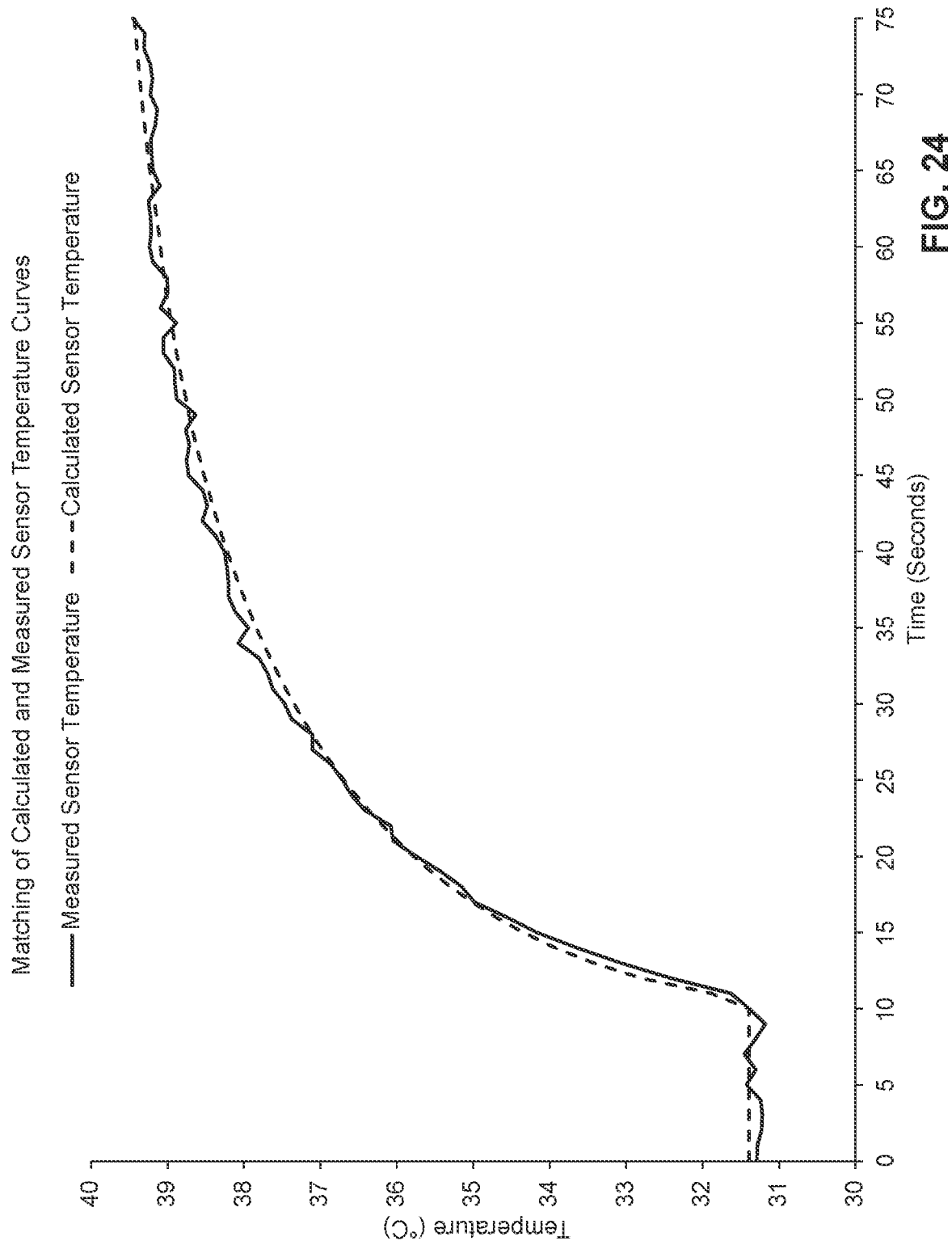
FIG. 24 is a graph illustrating an example of matching between a calculated (output) sensor temperature curve and a measured (input) sensor temperature for an example CHFT+ blood perfusion embodiment.
Figure 25:
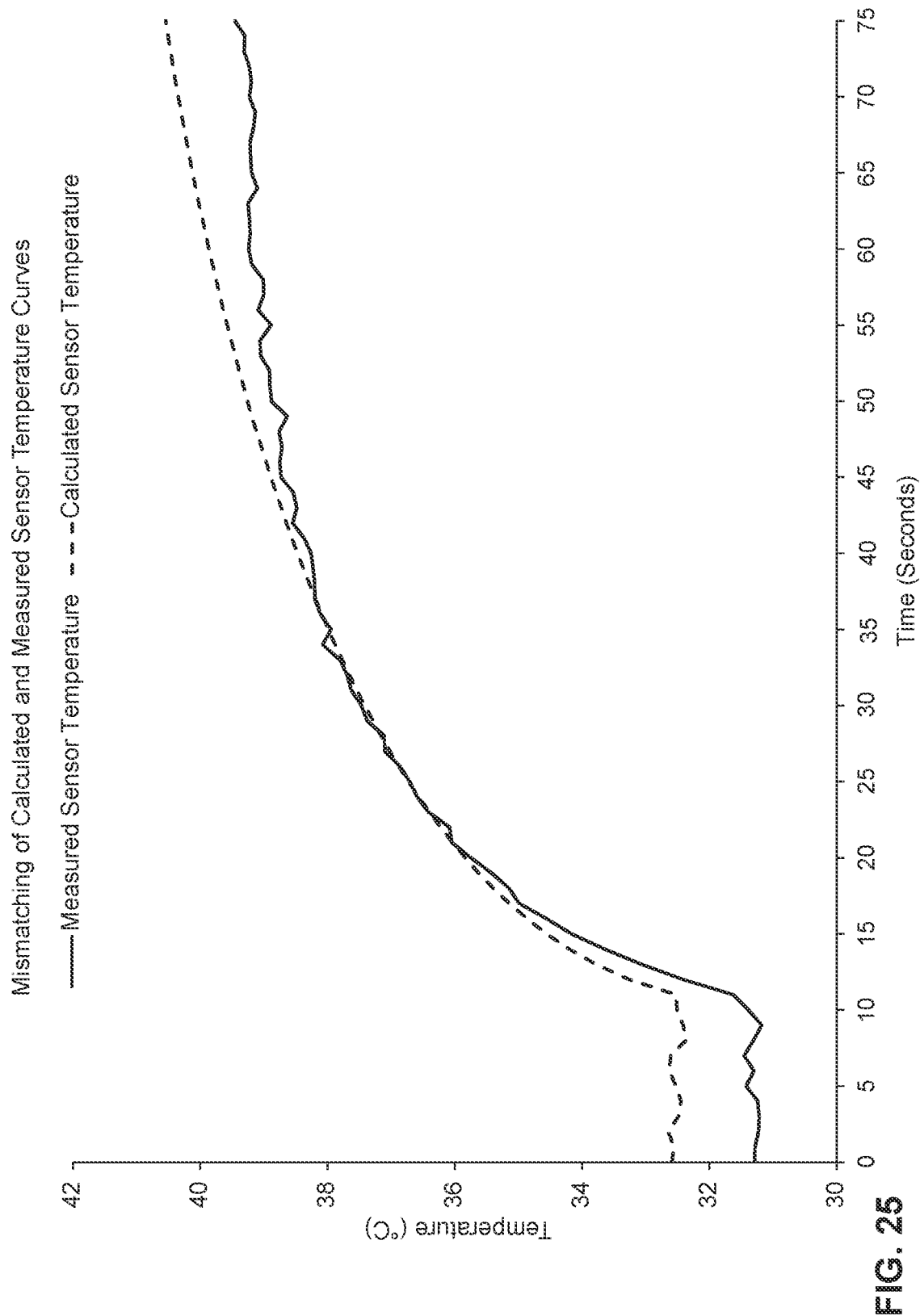
FIG. 25 is a graph illustrating an example of mismatching between a calculated (output) sensor temperature curve and a measured (input) sensor temperature for an example CHFT+ blood perfusion embodiment.

For the 15 CC/min case, FIG. 24 is a graph illustrating an example of matching between a calculated (output) sensor temperature curve and a measured (input) sensor temperature curve. The matching between the two temperature curves indicates that the internal parameter values (k,ρ,c,w) and the thermal contact resistance ($R_C''$) value used to construct the calculated (output) sensor temperature curve via Equation [41] are the same as the actual values occurring in the tissue (i.e., object). Incorrect values would result in poor matching as, for example, illustrated in FIG. 25.

TABLE 3

Results of Example Blood Perfusion CHFT+ Embodiment with Periodic Parameter Estimation Data Processing Method

| Flow Rate $\left(\frac{CC}{min}\right)$ | Perfusion − $w\left(\frac{ml_{B/S}}{ml_T}\right)$ | | | Temperature − $T_{Core}$ (° C.) | | $R_C'' \left(° C. \cdot \frac{m^2}{W}\right)$ |
|---|---|---|---|---|---|---|
| | CHFT+ | Phantom | Difference | CHFT+ | Phantom | |
| 10 | 0.0237 | 0.0185 | 21.94% | 32.83 | 32.92 | 0.000206 |
| 15 | 0.0360 | 0.0347 | 3.61% | 32.12 | 31.93 | 0.000205 |
| 20 | 0.0533 | 0.0524 | 1.69% | 33.03 | 33.23 | 0.000254 |
| 25 | 0.0810 | 0.0709 | 12.47% | 30.24 | 30.48 | 0.000218 |

Looking at Table 3, the estimated values for perfusion (w) using the example CHFT+ embodiment are in close agreement with the phantom CFD model (i.e., phantom) for the 15 CC/min and 20 CC/min flowrates. The 10 CC/min and 25 CC/min are subject to a 21.94% and 12.47% difference, respectively. This may be because when the inventor was performing the experimental data collection, it was difficult to maintain the 10 CC/min and 25 CC/min flowrates. When setting these flowrates, the flowrate would often skew higher than expected and resulted in higher flow measurements As mentioned previously, in this example, predetermined values for tissue thermal conductivity (k), tissue density (ρ), and tissue heat capacity (c) were input as constant values in the example data processing method performed for perfusion measurement above in order to determine the internal parameter of tissue thermal inertia ($\sqrt{k\rho C}$). Another way to determine tissue thermal inertia is, for example, via one or more parameter estimation schemes as a part of a data processing method.

Figure 26:
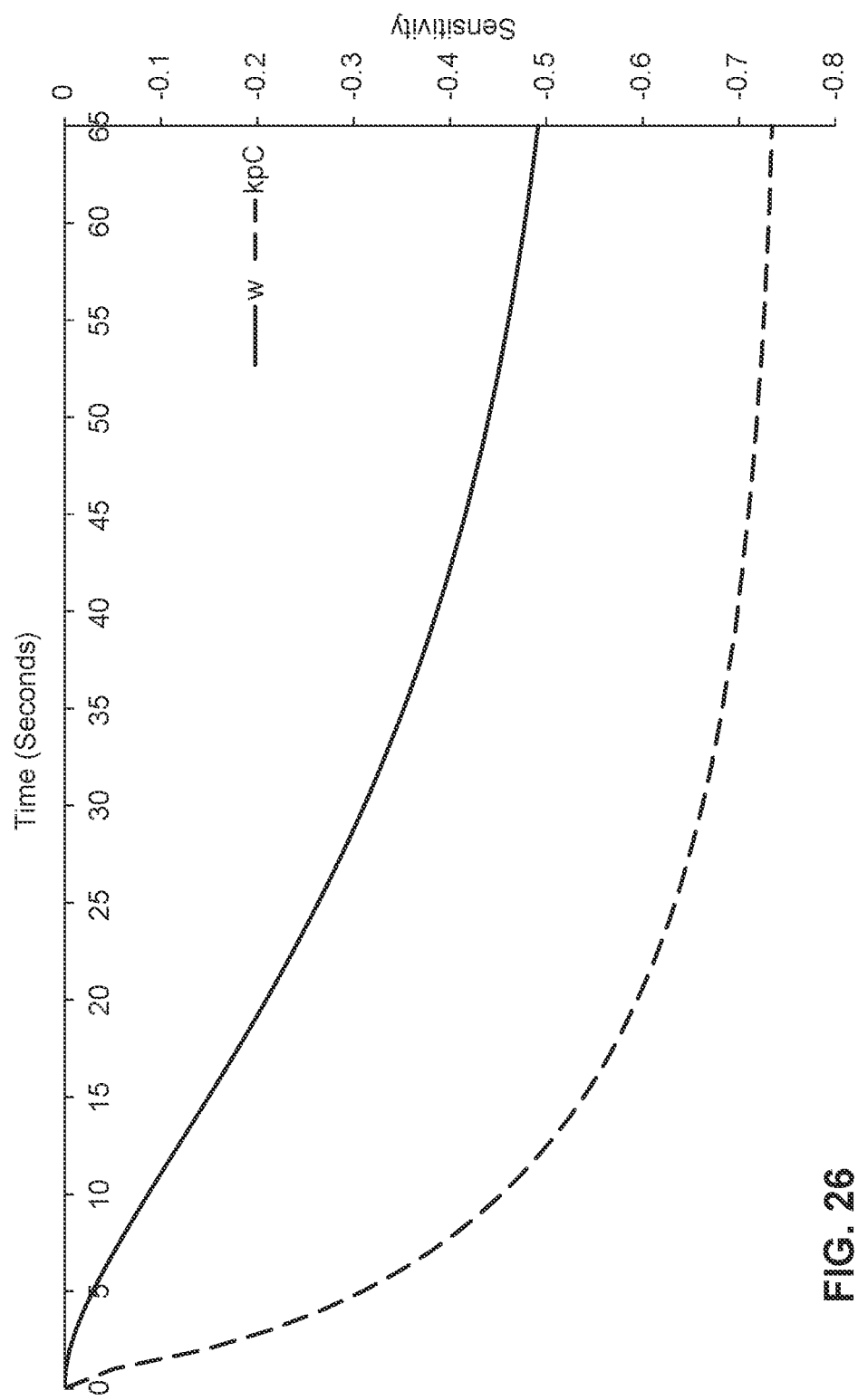
FIG. 26 is a graph illustrating the differing sensitivity of the calculated (output) sensor temperature curve to internal parameters over time in the example blood perfusion application.

One example way to estimate tissue thermal inertia may be to define different objective functions for different time periods of surface measurements made. This is possible because the calculated (output) sensor temperature curve has differing internal parameter sensitivity over time and, thus, the effects of each internal parameter (e.g., $\sqrt{k\rho C}$ and w) can be distinguished. Consequently, the internal parameter values can be individually estimated. FIG. 26 shows this differing sensitivity of the calculated (output) sensor temperature curve to internal parameters. Specifically, there is greater sensitivity to the product of tissue thermal conductivity (k), tissue density ($\rho$), and tissue heat capacity (C) during the initial time period, while sensitivity to blood perfusion (w) is initially minimal but increases with time. Thus, for example, in data processing methods that may include parameter estimation schemes, objective functions designed to determine an estimated value of k$\rho$C may be defined to include initial time periods while objective functions designed to determine the value of w may be defined to include later time periods. Additionally, the objective functions may be defined to operate simultaneously or in prescribed sequences (e.g., one after the other).

Another example way to determine tissue thermal conductivity (k), tissue density ($\rho$), and tissue heat capacity (C) is to calculate them after a blood perfusion (w) value has been determined when using predetermined values of tissue thermal conductivity (k), tissue density ($\rho$), and tissue heat capacity (C). For example, once an optimal blood perfusion (w) value has been determined using, for example, predetermined values for the internal parameters of tissue thermal conductivity (k), tissue density ($\rho$), and tissue heat capacity (C), the quantity k$\rho$C can be calculated using, for example, Equation [43]:

$$k\rho C = \frac{1}{w}\left(\frac{\sum_{j=1}^{m}\Delta q''_{Sensor,j} \times Erf\left(\sqrt{w(t_m - t_{j-1})}\right)}{T_{Sensor,m} - q''_{Sensor,m} \times R''_C - T_{Sensor,0} + q''_{Sensor,0} \times R''_C}\right)^2 \quad [43]$$

where the blood perfusion (w) on the right is the optimal blood perfusion (w) value determined when using predetermined (i.e., prior) values of tissue thermal conductivity (k), tissue density ($\rho$), and tissue heat capacity (C).

The method based on, for example, Equation [43] can be used in a variety of methods to determine, for example, the product of tissue thermal conductivity (k), tissue density ($\rho$), and tissue heat capacity (C). For example, measurements can be made at single or multiple indices (m). In the case of multiple indices, an average of the resulting values may, for example, be taken as the determined value. If desired, the more recent determined value for k$\rho$C may update the previously determined value and be used to re-estimate the blood perfusion (w) value. The more this routine is practiced, the more accurate the determined values of tissue thermal inertia ($\sqrt{k\rho C}$) and blood perfusion (w) may become. This non-limiting example NITI method may be used for some or all example NITI embodiments and/or applications.

Blood Perfusion—Real-Time Measurements Using Parameter Estimation Embodiment

In the example Blood Perfusion—Periodic Measurements using Parameter Estimation embodiment, data processing by the control circuitry starts after all measurements are made. Thus, in the experimental phantom testing above, measurements were output about every 75 seconds in a periodic manner. NITI sensor (e.g., CHFT+ or CHFT−) data may alternatively be processed in real-time to provide for real-time outputs of blood perfusion (w), core blood temperature ($T_{Core}$), and/or thermal contact resistance ($R_C''$) between the NITI sensor and the tissue surfaces. As time goes on, more data points are added to the surface heat flux and surface temperature curves that are processed in real-time by a data processing method that includes a parameter estimation scheme and outputs values in less than 1 second.

Blood Perfusion—Real-Time Measurements without Parameter Estimation Embodiment

Equation [39] can be rearranged as: where:

$$\sqrt{\frac{1}{k\rho cw}} = \frac{T_{Tissue,m} - (T_{Sensor,0} - q''_{Sensor,0} \times R''_C)}{\sum_{j=1}^{m}\Delta q''_{Sensor,j} \times Erf\left(\sqrt{w(t_m - t_{j-1})}\right)} \quad [44]$$

$$T_{Tissue,m} = T_{Sensor,m} - q''_{Sensor,m} \times R''_C \quad [45]$$

Combining Equation [44] and Equation [45]:

$$w = \left[k\rho c\left(\frac{(T_{Sensor,m} - q''_{Sensor,m} \times R''_C) - (T_{Sensor,0} - q''_{Sensor,0} \times R''_C)}{\sum_{j=1}^{m}\Delta q''_{Sensor,j} \times Erf\left(\sqrt{w(t_m - t_{j-1})}\right)}\right)^2\right]^{-1} \quad [46]$$

When the thermal contact resistance ($R_C''$) between the NITI sensor (e.g., CHFT+ or CHFT−) and the tissue surfaces is known and typical values for tissue thermal conductivity (k), tissue density ($\rho$), and tissue heat capacity (C) are input, Equation [46] may be used for real time blood perfusion measurement when a typical value of blood perfusion (w) is input on the right side. In some example embodiments, for example when change in blood perfusion (w) is of interest, the quantity $T_{Sensor,0} - q''_{Sensor,0} \times R_C''$ may be assumed at one or more specified times. In other example embodiments, the quantity $T_{Sensor,0} - q''_{Sensor,0} \times R_C''$ may be determined by, for example, using an additional temperature sensor; the output of which is indicative of tissue surface and/or core (i.e., internal) tissue temperature.

Although the calculated blood perfusion (w) value on the left side will not be exact, it will still suffice for accurate quantitative and/or qualitative measurements. Furthermore, for most accurate results, the typical value for blood perfusion (w) on the right side may be updated to reflect the most recent and/or accurate value calculated via Equation [46]. In other methods, the values for blood perfusion (w) on the right and left sides may be determined simultaneously, providing for accurate quantitative measurements. This may omit the need to input a typical blood perfusion (w) value on the right side. If the thermal contact resistance ($R_C''$) value is unknown, it can be determined (e.g., via the NITI procedures described above) or otherwise determined and accounted for. In some cases, the thermal contact resistance ($R_C''$) may be estimated to be negligible.

Furthermore, in steady-state conditions Equation [46] reduces to:

$$w = \left[k\rho c\left(\frac{(T_{Sensor,m} - q''_{Sensor,m} \times R''_C) - (T_{Sensor,0} - q''_{Sensor,0} \times R''_C)}{q''_{Sensor,m} - q''_{Sensor,0}}\right)^2\right]^{-1} \quad [47]$$

Equation [47] no longer requires a typical blood perfusion (w) value on the right side. Steady-state conditions could be achieved in a variety of ways including a control circuitry that regulates the heat flux and/or temperature occurring at the tissue surface via external thermal devices (e.g., heaters, coolers, etc.).

Blood Perfusion—Duo NITI Sensor Embodiment

For an example DUO NITI sensor embodiment when using first and second parallel NITI sensor nodes (each node having a heat flux sensor-temperature sensor pair), two independent equations are formed:

$$T_{Sensor1,m} - q''_{Sensor1,m} \times R''_{C1} = T_{Core} + q''_{Sensor1,0} \times \frac{1}{k}\sqrt{\frac{\alpha}{w}} + \sum_{j=1}^{m} \Delta q''_{Sensor1,j} \times \frac{1}{k}\sqrt{\frac{\alpha}{w}} \times Erf\left(\sqrt{w(t_m - t_{j-1})}\right) \quad [48]$$

$$T_{Sensor2,m} - q''_{Sensor2,m} \times R''_{C2} = T_{Core} + q''_{Sensor2,0} \times \frac{1}{k}\sqrt{\frac{\alpha}{w}} + \sum_{j=1}^{m} \Delta q''_{Sensor2,j} \times \frac{1}{k}\sqrt{\frac{\alpha}{w}} \times Erf\left(\sqrt{w(t_m - t_{j-1})}\right) \quad [49]$$

Using an example differential based data processing method, Equation [48]-Equation [49] yields:

$$w = \left[k\rho c \left(\frac{(T_{Sensor1,m} - q''_{Sensor1,m} \times R''_{C1}) - (T_{Sensor2,m} - q''_{Sensor2,m} \times R''_{C2})}{(q''_{Sensor1,0} - q''_{Sensor2,0} + \sum_{j=1}^{m} \Delta q''_{Sensor1,j} \times Erf\left(\sqrt{w(t_m - t_{j-1})}\right) - \sum_{j=1}^{m} \Delta q''_{Sensor2,j} \times Erf\left(\sqrt{w(t_m - t_{j-1})}\right))}\right)^2\right]^{-1} \quad [50]$$

This transient equation is a result of the DUO NITI sensor configuration and allows for real time blood perfusion (w) measurement regardless of core blood temperature ($T_{Core}$), when inputting typical values for tissue thermal conductivity (k), tissue density (ρ), tissue specific heat capacity (C), and blood perfusion (w) on the right.

Although the calculated blood perfusion (w) value on the left side will not be exact, it will still be very close and suffice for accurate quantitative and/or qualitative measurements. Furthermore, for most accurate results, the typical value for blood perfusion (w) may be updated to reflect the most recent and/or accurate value calculated via Equation [50]. In other methods, the values for blood perfusion (w) on the right and left sides may be determined simultaneously, providing for accurate quantitative measurements. This may omit the need to input a typical blood perfusion (w) value on the right side.

Estimated values for the thermal contact resistances ($R_{C1}$" and $R_{C2}$") between each NITI sensor (e.g., CHFT+ or CHFT−) and the tissue surfaces can be determined (e.g., via NITI procedures described above) or otherwise determined. In some cases, the thermal contact resistance ($R_{C1}$" and/or $R_{C2}$") may be estimated to be negligible.

In steady-state conditions, Equation [50] reduces to:

$$w = \left[k\rho c \left(\frac{(T_{Sensor1,m} - q''_{Sensor1,m} \times R''_{C1}) - (T_{Sensor2,m} - q''_{Sensor2,m} \times R''_{C2})}{(q''_{Sensor1,m} - q''_{Sensor2,m})}\right)^2\right]^{-1} \quad [51]$$

where a typical blood perfusion (w) value is no longer required on the right side. Steady-state conditions could be achieved in a variety of ways including a control circuitry that regulates the heat flux and/or temperature occurring at the tissue surface via external thermal devices (heaters, coolers, etc.).

Figure 27:
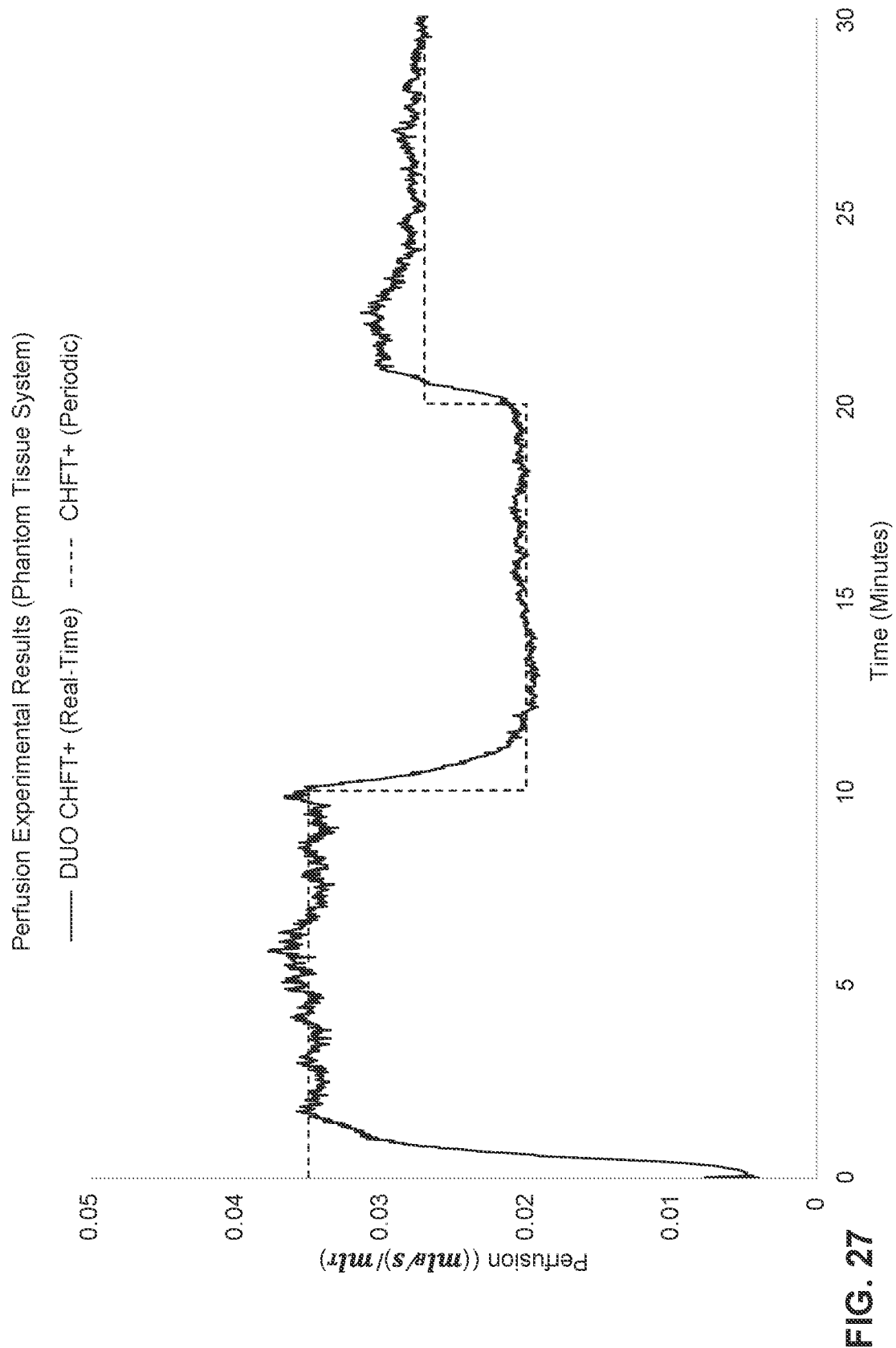
FIG. 27 is a graph showing results of an example DUO CHFT+ embodiment and an example Periodic CHFT+ embodiment when used to measure perfusion rate of a perfusing pseudo tissue.

FIG. 27 is a graph showing results of an example DUO CHFT+ embodiment when used to measure the perfusion (w) of pseudo tissue on the phantom at different flowrates of 30 CC/min, 20 CC/min and, 10 CC/min. This graph shows that the example DUO CHFT+ embodiment is capable of determining the perfusion (w) of pseudo tissue on the phantom when initially turned on at 30 CC/min (perfusion (w) rate of ~0.035 $ml_{B/S}/ml_T$). Subsequently, after about 10 minutes, the example DUO CHFT+ embodiment determines the change in perfusion (w) in real-time as the phantom flowrate is adjusted to 10 CC/min (perfusion (w) rate of ~0.020 $ml_{B/S}/ml_T$) and later increased to 20 CC/min (perfusion (w) rate of ~0.027 $ml_{B/S}/ml_T$), where the experimental measurements end after about 10 minutes. To show the accuracy and agreement of the example DUO CHFT+ method in real-time, a different example NITI method for perfusion measurement (CHFT+ Periodic) is also used to determine the perfusion rate at each specified flowrate. The agreement between the two measures indicates the validity of both methods in determining perfusion (w) rate of tissue.

Hydration of Tissue Measurement Application

All of the example methods and embodiments for Blood Perfusion Measurement above can be also used to determine $$\sqrt{\frac{1}{k\rho cw}} = \frac{1}{k}\sqrt{\frac{\alpha}{w}},$$

which is the steady-state thermal resistance (R") of tissue as defined in these example methods. The steady-state thermal resistance (R") of tissue may be an accurate and reliable indicator of tissue hydration. For example, correlations could be developed and used as a means to gauge tissue hydration and dehydration levels based on, for example, the tissue steady-state thermal resistance. Independent values indicative of blood perfusion (w), or other internal parameters, may also be used to gauge tissue hydration and dehydration levels.

Core Temperature of Tissue Measurement Application

Combining Equation [37] and Equation [38]:

$$T_{Tissue,m} = T_{Core} + q''_{Sensor,0} \times \frac{1}{k}\sqrt{\frac{\alpha}{w}} + \sum_{j=1}^{m} \Delta q''_{Sensor,j} \times \frac{1}{k}\sqrt{\frac{\alpha}{w}} \times Erf\left(\sqrt{w(t_m - t_{j-1})}\right) \quad [52]$$

Rewriting Equation [52] in terms of NITI sensor outputs and including effects of the thermal contact resistance ($R_C$") between the NITI sensor and the tissue surfaces:

$$T_{Sensor,m} - q''_{Sensor,m} \times R''_C = T_{Core} + q''_{Sensor,0} \times \frac{1}{k}\sqrt{\frac{\alpha}{w}} + \sum_{j=1}^{m} \Delta q''_{Sensor,j} \times \frac{1}{k}\sqrt{\frac{\alpha}{w}} \times Erf\left(\sqrt{w(t_m - t_{j-1})}\right) \quad [53]$$

Rearranging and realizing that $T_{Core}$ is dependent on values that change over time (measurement index (m)):

$$T_{Core,m} = T_{Sensor,m} - q''_{Sensor,m} \times R''_C - \qquad [54]$$
$$q''_{Sensor,0} \times \frac{1}{k}\sqrt{\frac{\alpha}{w}} - \sum_{j=1}^{m} \Delta q''_{Sensor,j} \times \frac{1}{k}\sqrt{\frac{\alpha}{w}} \times Erf\left(\sqrt{w(t_m - t_{j-1})}\right)$$

Equation [54] is an example equation for core tissue temperature ($T_{Tissue,m}$) measurement and is used in the following example embodiments below. For some of these example embodiments, values of tissue thermal conductivity (k), tissue density (ρ), tissue specific heat capacity (C), thermal contact resistance ($R_C''$) between the NITI sensor and the tissue surfaces, and/or blood perfusion (w) need to be determined. This can be done by, for example, determining these values (e.g., via the CHFT+ or CHFT− methods described prior) or, for example, by using predetermined values (e.g., values from a textbook).

Core Temperature of Tissue—CHFT+ (Active Thermometry) Embodiment

A CHFT+ embodiment uses an integrated external thermal device such as a heater to create a thermal event (i.e., heat transfer) that can be used to perform NITI. For core tissue temperature ($T_{Core,m}$) measurement, the heater may operate in any manner (steady, periodic, cycled, etc.) and, in this example, Equation [54] would output the core tissue temperature ($T_{Core,m}$) accurately and in real-time when values for blood perfusion (w), tissue thermal conductivity (k), tissue density (ρ), tissue heat capacity (C), and estimated thermal contact resistance ($R_C''$) are input on the right side. These values could be determined by, for example, using a data processing method (e.g., that includes a parameter estimation scheme) or otherwise determined and accounted for. In some cases, the thermal contact resistance ($R_C''$) may be estimated to be negligible. Although not required, it may be beneficial to cover the CHFT+ with insulating material to prevent erroneous signals from external stimuli such as running, contact, etc.

Figure 28:
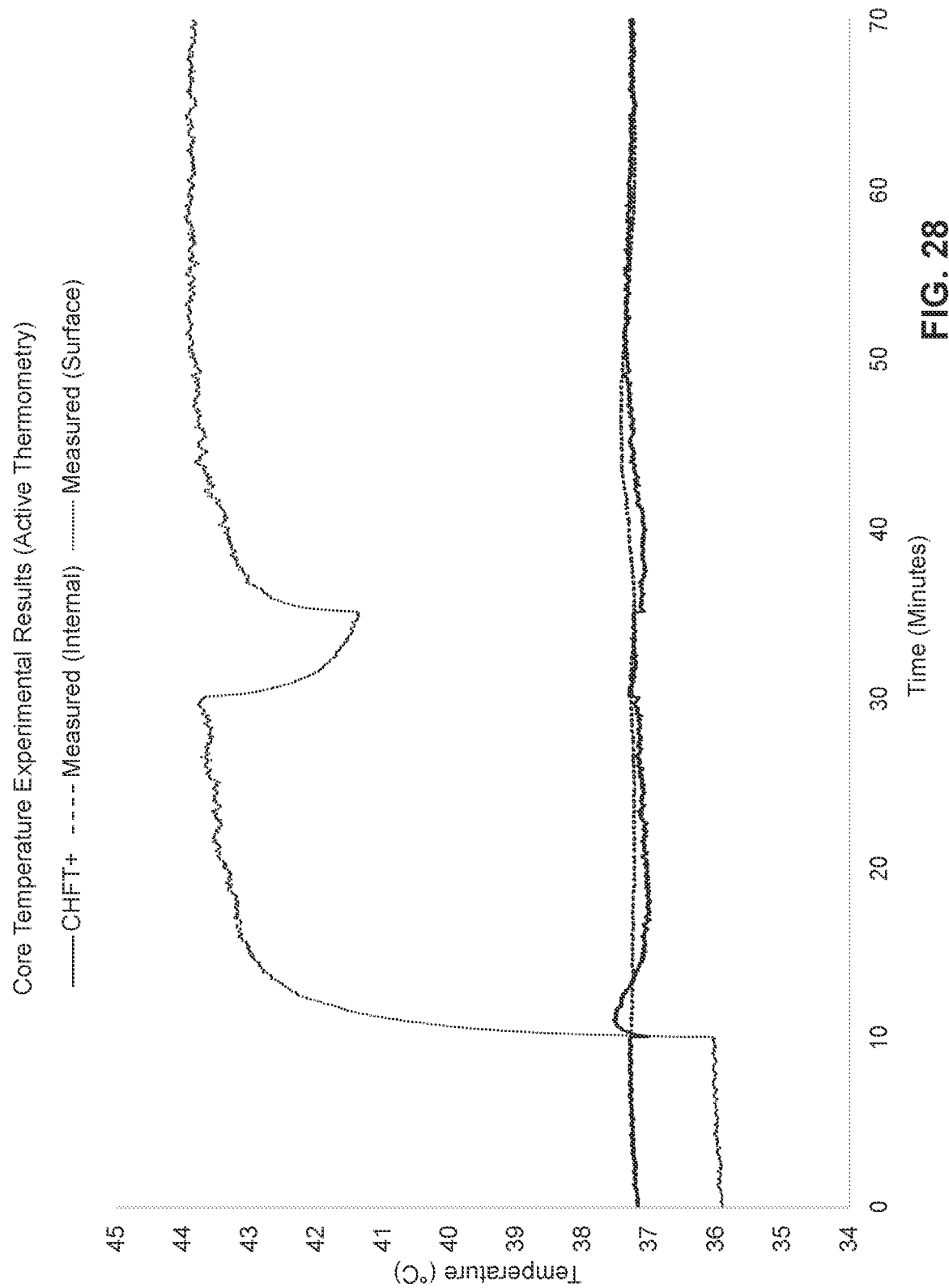
FIG. 28 is a graph showing results of an example CHFT+ embodiment (Active Thermometry) when used to measure the core temperature of perfusing pseudo tissue.

FIG. 28 is a graph showing results of an example CHFT+ embodiment (with integrated heater) when used to measure the core temperature ($T_{Core,m}$) of pseudo tissue on the phantom at a flowrate of 2 CC/min. In this graph, it is shown that the example CHFT+ embodiment is capable of determining the core temperature ($T_{Core,m}$) of pseudo tissue on the phantom (i.e., Measured (Internal)) regardless of surface temperature conditions. Specifically, the surface temperature increases initially as a result of the integrated heater being turned on. Subsequently, after a period of time, the surface temperature decreases as a result of an external fan (i.e., thermal disturbance) being blown on the example CHFT+ embodiment. Regardless of these sudden and unexpected changes in the ambient thermal conditions, the example CHFT+ embodiment measures the core temperature ($T_{Core,m}$) of the pseudo tissue with close agreement to an internal probe placed within the phantom and under the pseudo tissue.

Core Temperature of Tissue—CHFT− (Passive Thermometry) Embodiment

A CHFT− embodiment uses external thermal events such as, for example, body heat dissipation from a mammal to perform NITI. When subject to an external thermal event, Equation [54], for example, would output the core tissue temperature ($T_{Core,m}$), accurately and in real-time when values for blood perfusion (w), tissue thermal conductivity (k), tissue density (ρ), tissue heat capacity (C), and estimated thermal contact resistance ($R_C''$) are input on the right side. These values could be determined by, for example, using a data processing method (e.g., that includes a parameter estimation scheme) or otherwise determined and accounted for. In some cases, the thermal contact resistance ($R_C''$) may be estimated to be negligible. Although not required, it may be beneficial to cover the CHFT− with insulating material to prevent erroneous signals from external stimuli such as running, contact, etc.

Figure 29:
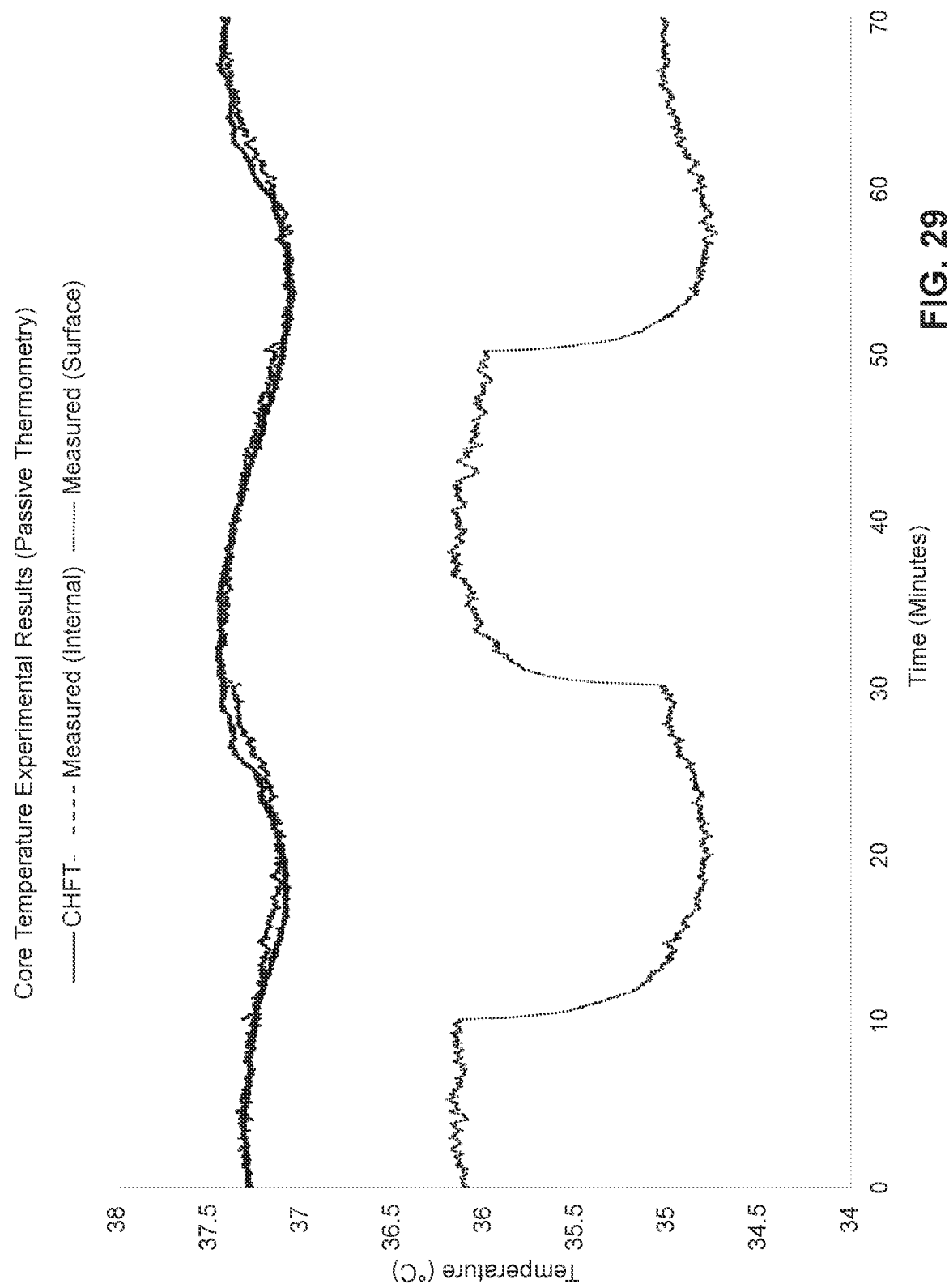
FIG. 29 is a graph showing results of an example CHFT− embodiment (Passive Thermometry) when used to measure the core temperature of perfusing pseudo tissue.

FIG. 29 is a graph showing results of an example CHFT− embodiment when used to measure the core temperature ($T_{Core,m}$) of pseudo tissue on the phantom at a flowrate of 2 CC/min. In this graph it is shown that the example CHFT− embodiment is capable of determining the core temperature ($T_{Core,m}$) of pseudo tissue on the phantom (i.e., Measured (Internal)) regardless of surface temperature conditions. Specifically, although the surface temperature is initially stable, an external fan (i.e., thermal disturbance) is cycled (i.e., turned on and off) to blow air on the example CHFT− embodiment and pseudo tissue. Regardless of these sudden and unexpected changes in the ambient thermal conditions, the example CHFT− embodiment measures the core temperature ($T_{Core,m}$) of the pseudo tissue with close agreement to an internal probe placed within the phantom and under the pseudo tissue.

Core Temperature of Tissue—CHFT+(Periodic Measurement) Embodiment

In addition to the example real-time methods and embodiments for Core Temperature of Tissue Measurement above, a NITI sensor (e.g., CHFT+ or CHFT−) can be used to make periodic measures of core tissue temperature ($T_{Core}$) when operating in differing steady-state conditions. For example, steady-state measurements prior to a thermal event ($T_{Sensor,0}$, $q_{Sensor,0}''$) can be compared with steady-state measurements during, after, or at the end of a thermal event ($T_{Sensor,END}$, $q_{Sensor,END}''$) in order to determine core tissue temperature ($T_{Core}$) using:

$$T_{Core} = \frac{T_{Sensor,0} \times q''_{Sensor,END} - T_{Sensor,END} \times q''_{Sensor,0}}{q''_{Sensor,END} - q''_{Sensor,0}} \qquad [55]$$

CHFT+ and/or CHFT− example embodiments can both be subject to differing steady-state conditions over time. However, CHFT+ embodiments are preferred due to the increased operational control of the one or more external thermal devices that may be used to create differing steady-state conditions.

Core Temperature—CHFT+(Zero Heat-Flux Thermometry) Embodiment

Using control circuitry, an example CHFT+ embodiment may be used to create a zero heat-flux environment where no heat transfer occurs between the tissue and the sensor surfaces, i.e., where no heat enters or leaves the tissue as measured by the heat flux sensor (minimal voltage output, i.e., "zero"). In steady-state conditions, a zero heat-flux environment simplifies Equation [54] to:

$$T_{Core,m} = T_{Sensor,m} \quad [56]$$

where the measured sensor temperature ($T_{Sensor,m}$) is equivalent to the core temperature of the tissue ($T_{Core,m}$).

An advantage of this method is the independence of core tissue temperature ($T_{Core,m}$) measurement from the internal parameter values (e.g., blood perfusion (w), tissue thermal inertia ($\sqrt{k\rho C}$), etc.) and thermal contact resistance ($R_C''$) once a steady-state zero heat-flux environment is obtained. The amount of time required to achieve such steady-state conditions, as determined by the measured sensor temperature ($T_{Sensor,m}$) output, varies depending on the example embodiment used and is a common limitation of existing Zero Heat-Flux technologies that do not utilize NITI technology. Until a steady-state zero heat-flux environment is obtained, example NITI Zero Heat-Flux Thermometry embodiments may utilize other example embodiments, such as an example Active Thermometry embodiment for Core Temperature of Tissue Measurement, to make accurate measurements of core tissue temperature ($T_{Core,m}$).

Figure 30:
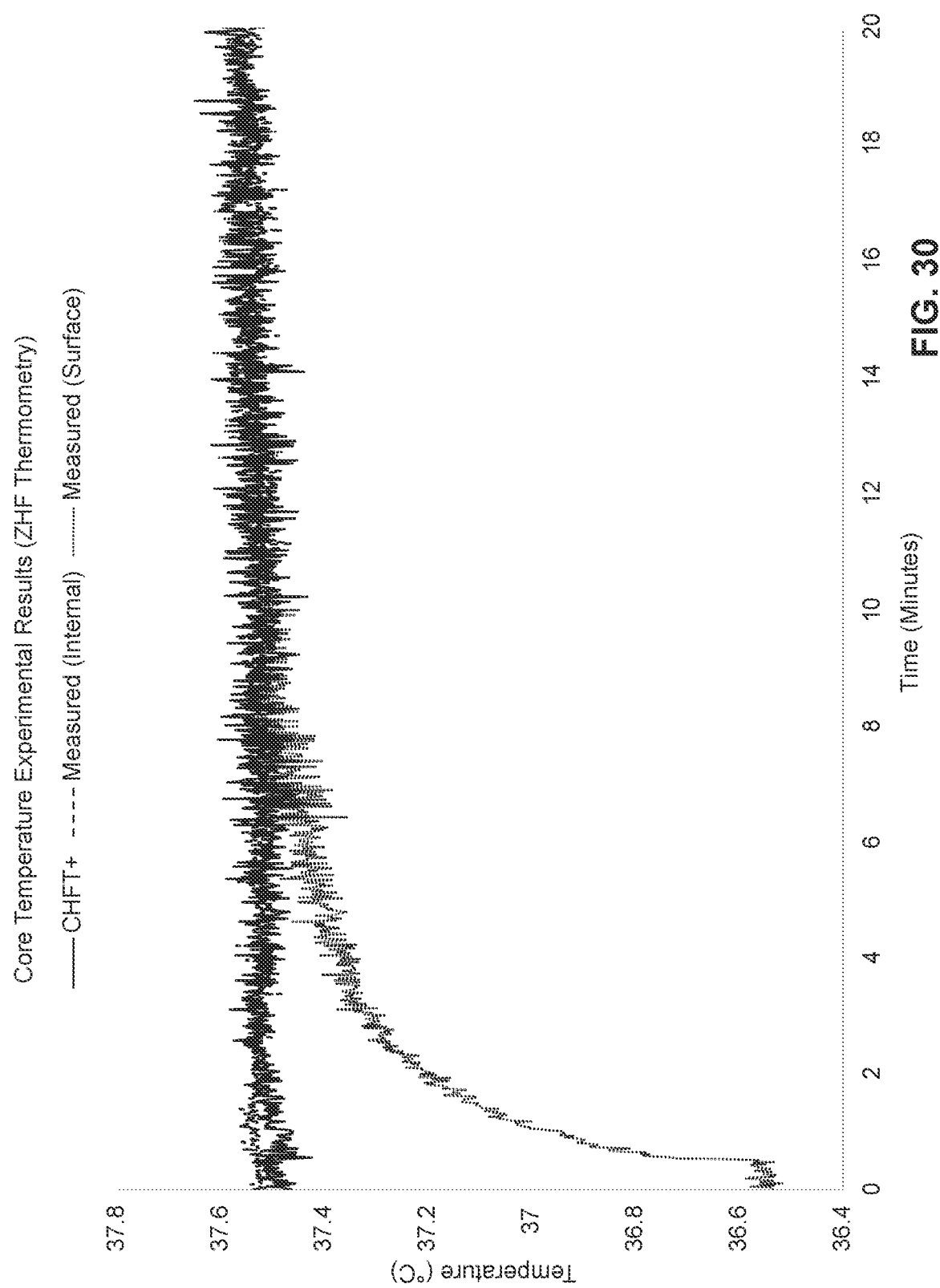
FIG. 30 is a graph showing results of an example CHFT+ ZHF embodiment (Zero Heat-Flux Thermometry) when used to measure the core temperature of perfusing pseudo tissue.

FIG. 30 is a graph showing results of an example CHFT+ Zero Heat-Flux (ZHF) embodiment when used to measure the core temperature ($T_{Core,m}$) of pseudo tissue on the phantom at a flowrate of 2 CC/min. This graph shows that the example CHFT+ ZHF embodiment is capable of determining the core temperature ($T_{Core,m}$) of pseudo tissue on the phantom regardless of surface temperature conditions and without delay. Specifically, although the surface temperature takes approximately 8 minutes to achieve an output indicative of the pseudo tissue core temperature ($T_{Core,m}$), the example CHFT+ ZHF embodiment measures the core temperature ($T_{Core,m}$) of the pseudo tissue from the onset with close agreement when compared to an internal probe placed within the phantom and under the tissue.

Core Temperature—Duo NITI (Dual Thermometry) Embodiment

For an example DUO NITI embodiment when using first and second parallel NITI sensor nodes (each node having a heat flux sensor-temperature sensor pair), two independent equations are formed:

$$(T_{Sensor1,m} - q''_{Sensor1,m} \times R''_{C1}) - T_{Core,m} = \quad [57]$$
$$\frac{1}{k}\sqrt{\frac{\alpha}{w}}\left(q''_{Sensor1,0} + \sum_{j=1}^{m}\Delta q''_{Sensor1,j} \times Erf(\sqrt{w(t_m - t_{j-1})})\right)$$

$$(T_{Sensor2,m} - q''_{Sensor2,m} \times R''_{C2}) - T_{Core,m} = \quad [58]$$
$$\frac{1}{k}\sqrt{\frac{\alpha}{w}}\left(q''_{Sensor2,0} + \sum_{j=1}^{m}\Delta q''_{Sensor2,j} \times Erf(\sqrt{w(t_m - t_{j-1})})\right)$$

Using a quotient based data processing method, Equation [57]/Equation [58] yields:

$$\frac{(T_{Sensor1,m} - q''_{Sensor1,m} \times R''_{C1}) - T_{Core,m}}{(T_{Sensor2,m} - q''_{Sensor2,m} \times R''_{C2}) - T_{Core,m}} = \quad [59]$$

$$\frac{(q''_{Sensor1,0} + \sum_{j=1}^{m}\Delta q''_{Sensor1,j} \times Erf(\sqrt{w(t_m - t_{j-1})}))}{(q''_{Sensor2,0} + \sum_{j=1}^{m}\Delta q''_{Sensor2,j} \times Erf(\sqrt{w(t_m - t_{j-1})}))}$$

Rearranging:

$$T_{Core,m} = \frac{\begin{aligned}&(T_{Sensor2,m} - q''_{Sensor2,m} + R''_{C2}) \times \\ &(q''_{Sensor1,0} + \sum_{j=1}^{m}\Delta q''_{Sensor1,j} \times Erf(\sqrt{w(t_m - t_{j-1})})) - \\ &(T_{Sensor1,m} - q''_{Sensor1,m} + R''_{C1}) \times \\ &(q''_{Sensor2,0} + \sum_{j=1}^{m}\Delta q''_{Sensor2,j} \times Erf(\sqrt{w(t_m - t_{j-1})}))\end{aligned}}{\begin{aligned}&(q''_{Sensor1,0} + \sum_{j=1}^{m}\Delta q''_{Sensor1,j} \times Erf(\sqrt{w(t_m - t_{j-1})})) - \\ &(q''_{Sensor2,0} + \sum_{j=1}^{m}\Delta q''_{Sensor2,j} \times Erf(\sqrt{w(t_m - t_{j-1})}))\end{aligned}} \quad [60]$$

This transient equation is a result of the DUO NITI configuration and allows for real time core tissue temperature ($T_{Core,m}$) measurement when inputting typical values for tissue thermal conductivity (k), tissue density ($\rho$), tissue specific heat capacity (C), and blood perfusion (w) on the right side.

Estimated values for the thermal contact resistances ($R_{C1}''$ and $R_{C2}''$) between each NITI sensor node (e.g., CHFT+ or CHFT−) and the tissue surfaces can be determined (e.g., via NITI procedures described above) or otherwise determined and accounted for. In some cases, the thermal contact resistances ($R_{C1}''$ and/or $R_{C2}''$) may be estimated to be negligible.

In steady-state conditions, and where $R_{C1}'' \approx R_{C1}'' \approx R_{C2}''$ or $R_{C1}''$ and $R_{C2}''$ are estimated to be negligible, Equation [60] reduces to:

$$T_{Core,m} = \frac{T_{Sensor2,m} \times q''_{Sensor1,m} - T_{Sensor1,m} \times q''_{Sensor2,m}}{q''_{Sensor1,m} - q''_{Sensor2,m}} \quad [61]$$

where typical values for tissue thermal conductivity (k), tissue density ($\rho$), tissue specific heat capacity (C), and blood perfusion (w) are no longer required on the right side. Steady-state conditions could be achieved in a variety of ways including a control circuitry that regulates the heat flux and/or temperature occurring at the tissue surface via external thermal devices (e.g., heaters, coolers, etc.).

Pipe Parameter Determination Application

Figure 31:
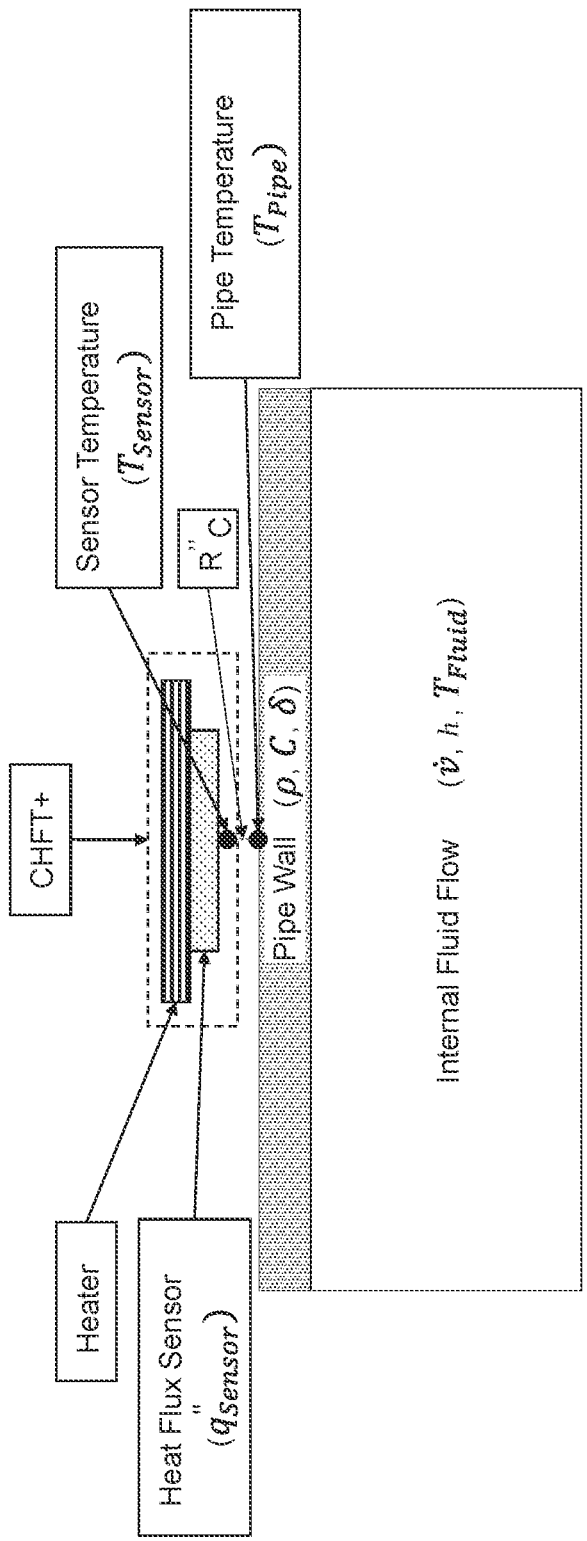
FIG. 31 shows another application of the technology to determining one or more parameters related to fluid flowing in a pipe or other conduit.

FIG. 31 shows another application of NITI technology to determine one or more internal parameters related to fluid flowing in a pipe or other conduit. In this example, a heater is used (example CHFT+ embodiment), but in other examples, the heater (i.e., external thermal device) is optional.

An example thermal mathematical solution for a pipe or other conduit (e.g., a copper pipe) with internal flow when subject to surface heat flux is:

$$T_{Pipe,m} = T_{Pipe,0} + \sum_{j=1}^{m}\left(\frac{q''_{Sensor,j} - q''_{Sensor,j-1}}{h}\right)(1 - e^{-\left(\frac{t_m - t_{j-1}}{\tau}\right)}) \quad [62]$$

where the initial pipe surface temperature is:

$$T_{Pipe,0} = T_{Fluid} + \frac{q''_{Sensor,0}}{h} \quad [63]$$

where heat flux is defined to be positive when entering the pipe/conduit and where $$\tau = \frac{\rho C \delta}{h}$$

is the thermal time constant (i.e., time constant) of the pipe/conduit, $\rho$ is the density of the pipe/conduit, C is the specific heat capacity of the pipe/conduit, $\delta$ is the wall thickness of the pipe/conduit, h is the internal convection heat transfer coefficient (i.e., convection coefficient) of the pipe/conduit and related to the internal flowrate (i.e., flowrate) of the pipe/conduit, $T_{Pipe}$ is the pipe/conduit surface temperature, and $T_{Fluid}$ is the core (i.e., internal) fluid temperature.

Rewriting Equation [62] in terms of NITI sensor outputs and including effects of the thermal contact resistance ($R_C''$) between the NITI sensor and the pipe/conduit surfaces yields:

$$T_{Pipe,m} = \qquad \qquad [64]$$
$$T_{Sensor,0} - q_{Sensor,0}'' \times R_C'' + \sum_{j=1}^{m}\left(\frac{q_{Sensor,j}'' - q_{Sensor,j-1}''}{h}\right)\left(1 - e^{-\left(\frac{t_m - t_{j-1}}{\tau}\right)}\right)$$

where $\frac{1}{h}$ is the steady-state thermal resistance (R") of convective internal flowrate.

Equation [62] and Equation [64] are valid for pipes or conduits made of materials with high thermal conductivity. For other materials, such as PVC, a different thermal model and corresponding solution may need to be developed. Other thermal models and solutions may also be developed for materials with high thermal conductivity.

In this example, the greater the flowrate ($\dot{v}$), the greater the convection heat transfer coefficient (h). The relationship between 1, and h is typically not linear, unless at low (e.g., laminar) flowrates, and a correlation function between the two variables is therefore desirable. This correlation function can be found, for example, through experimental testing. One example of a correlation experimentally found when a CHFT+ was operated on a ¾" (0.01905 m) inner diameter L type copper pipe with a 0.05" (0.00127 m) wall thickness is:

$$h = 1035.2\left[\frac{W}{m^2 - {}^\circ C}\left(\frac{min}{gal}\right)^{0.2137}\right]\dot{v}^{0.2137} \qquad [65]$$

Rearranging:

$$\dot{v} = 1 * 10^{-14}\left[\frac{gal}{min}\left(\frac{m^2 - {}^\circ C}{W}\right)^{4.6475}\right]h^{4.6475} \qquad [66]$$

Thus, an example general form of a correlation between convection coefficient (h) and flowrate ($\dot{v}$), may be:

$$h = Z\left[\frac{W}{m^2 - {}^\circ C}\left(\frac{min}{gal}\right)^P\right]\dot{v}^P \qquad [67]$$

where Z and P are correlation values.

Other forms of correlations can be developed depending on mathematical techniques used (e.g., logarithmic functions, exponentials, etc.).

Figure 32:
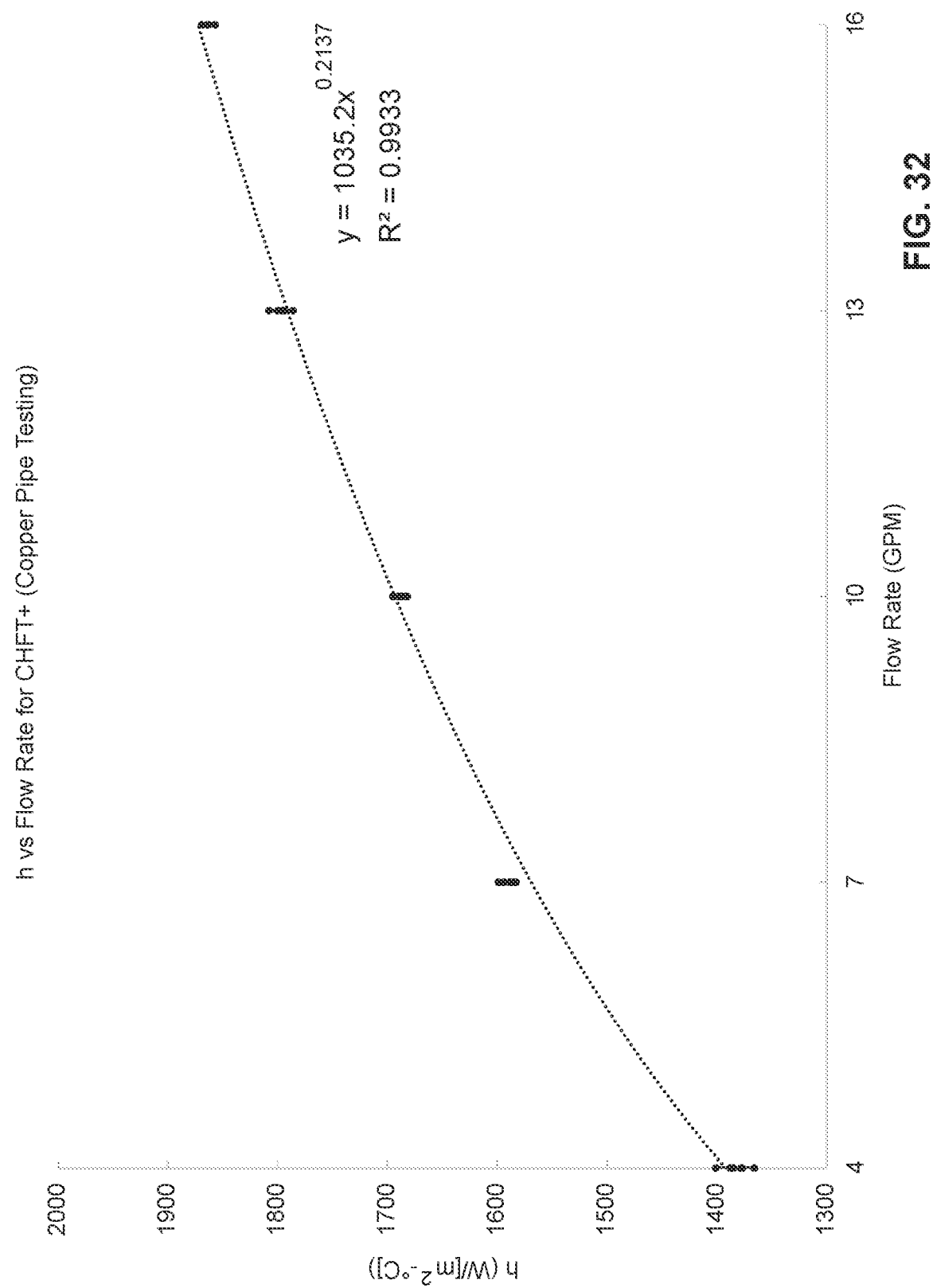
FIG. 32 is a graph showing an example correlation developed with experimental measurements for fluid flow in a copper pipe.

FIG. 32 is a graph showing how the example correlation may be developed with experimental measurements. In this example, the correlation is found by plotting the experimental results for measurements made at different flowrates. Once a sufficient number of measurements are made at different flowrates, a best fit curve (e.g., trend line) can be used to find a correlation (i.e., equation) relating measured convection coefficient (h) to flowrate ($\dot{v}$) or vice versa.

In other example embodiments, correlations functions and/or other methods of relating the convection heat transfer coefficient (h) to the flowrate ($\dot{v}$), or vice versa, may be determined using machine learning methods (e.g., neural networks, etc.).

Pipe Application—Periodic Measurements Using Parameter Estimation Embodiment

For an example NITI sensor embodiment (e.g., CHFT+ or CHFT−) with a periodic data processing method, Equation [64] may be used in a parameter estimation scheme to determine the internal parameter of convection coefficient (h), core (i.e., internal) fluid temperature ($T_{Fluid}$), and/or the thermal contact resistance ($R_C''$) between the NITI sensor and the pipe/conduit surfaces. This is similar to the general case presented as an example for example NITI system embodiments with one or more heat flux sensor-temperature sensor pairs section above but with a different thermal model for a different NITI application. In this example, predetermined constant values for the internal parameters of pipe density ($\rho$), pipe heat capacity (C), and pipe wall thickness ($\delta$) were used. In this example, the predetermined values were obtained from the pipe manufacturer specification. An example objective function to be minimized in this example application is:

$$RMSE = \sqrt{\frac{1}{M-1}\sum_{m=1}^{M-1}(T_{sensor,m} - T_{Calculated,m})^2} \qquad [68]$$

where:

$$T_{Calculated,m} = T_{Pipe,m} + q_{Sensor,m}'' \times R_C'' \qquad [69]$$

$$R_C'' = \frac{\sum_{n=1}^{N-1}\frac{T_{Sensor,n} - T_{Pipe,n}}{q_{sensor,n}}}{N-1} \qquad [70]$$

and where:

An example CHFT+ embodiment (with heater) was tested on a ¾" (0.01905 m) inner diameter L type copper pipe with a 0.05" (0.00127 m) wall thickness with water flowing through it at different flowrates and temperatures. The CHFT+ was attached to the pipe surface and measurements were made as follows:

10 seconds of steady-state data was recorded.

Heater turned on for approximately 65 seconds, resulting in a transient thermal response of the pipe wall as measured by the CHFT+ via surface heat flux and surface temperature signals.

The entirety of the data was processed via a periodic data processing method that included a parameter estimation scheme in less than 1 second, resulting in outputs of convection coefficient (h), core water temperature ($T_{Fluid}$), and thermal contact resistance ($R_C''$) between the CHFT+ and the pipe surfaces.

Once the convection coefficient (h) is determined, it is used in a correlation equation (e.g., Equation [66]) to determine flowrate which is related to fluid mass flowrate and speed (e.g., kg/s and m/s). Results are tabulated in Table 4 below.

construct the calculated (output) sensor temperature curve via Equation [69] are the same as the actual values occurring in the pipe (i.e., object).

As mentioned previously, in this example, predetermined values for pipe density (ρ), pipe heat capacity (C), and pipe wall thickness (δ) were determined using the manufacturer's specification of the copper piping and input as constant values in the example data processing method performed for pipe parameter determination. Although it was determined as a part of the data processing method in this example, the value for the estimated thermal contact resistance ($R_C''$) can

TABLE 4

Results of Pipe Parameter Determination
(Example CHFT+ Embodiment with Periodic Parameter Estimation)

| Flowrate $\left(\frac{gal}{min}\right)$ | $h\left(\frac{W}{m^{2\circ}C.}\right)$ | $\tau(s)$ | $R_C''\left(\circ C.\frac{m^2}{W}\right)$ | RMSE (° C.) | CHFT+ Estimated Flowrate $\left(\frac{gal}{min}\right)$ |
|---|---|---|---|---|---|
| 1 | 838 | 5.22 | 0.000331 | 0.126 | 0.9 |
|   | 829 | 5.27 | 0.000327 | 0.134 | 0.9 |
|   | 825 | 5.30 | 0.000334 | 0.134 | 0.9 |
|   | 826 | 5.29 | 0.000331 | 0.143 | 0.9 |
|   | 826 | 5.29 | 0.000334 | 0.137 | 0.9 |
|   | 826 | 5.29 | 0.000329 | 0.041 | 0.9 |
| 4 | 1378 | 3.17 | 0.000329 | 0.041 | 3.9 |
|   | 1385 | 3.16 | 0.000329 | 0.038 | 4.0 |
|   | 1377 | 3.17 | 0.000329 | 0.043 | 3.9 |
|   | 1366 | 3.20 | 0.000328 | 0.041 | 3.7 |
|   | 1388 | 3.15 | 0.000328 | 0.037 | 4.0 |
|   | 1401 | 3.12 | 0.000331 | 0.036 | 4.2 |
| 7 | 1588 | 2.75 | 0.000331 | 0.023 | 7.5 |
|   | 1585 | 2.76 | 0.000328 | 0.023 | 7.4 |
|   | 1583 | 2.76 | 0.000329 | 0.024 | 7.4 |
|   | 1594 | 2.74 | 0.000328 | 0.021 | 7.6 |
|   | 1589 | 2.75 | 0.000331 | 0.022 | 7.5 |
|   | 1599 | 2.73 | 0.00033 | 0.023 | 7.8 |
| 10 | 1687 | 2.59 | 0.000332 | 0.020 | 10.0 |
|   | 1695 | 2.58 | 0.000333 | 0.021 | 10.2 |
|   | 1690 | 2.59 | 0.000331 | 0.021 | 10.0 |
|   | 1688 | 2.59 | 0.000333 | 0.023 | 10.0 |
|   | 1683 | 2.60 | 0.000331 | 0.022 | 9.8 |
|   | 1682 | 2.60 | 0.000331 | 0.025 | 9.8 |
| 13 | 1786 | 2.45 | 0.000332 | 0.019 | 13.0 |
|   | 1796 | 2.43 | 0.000331 | 0.019 | 13.3 |
|   | 1808 | 2.42 | 0.000331 | 0.020 | 13.7 |
|   | 1794 | 2.44 | 0.000329 | 0.019 | 13.2 |
|   | 1794 | 2.44 | 0.000329 | 0.020 | 13.2 |
|   | 1800 | 2.43 | 0.00033 | 0.020 | 13.5 |
| 16 | 1869 | 2.34 | 0.000329 | 0.019 | 16.0 |
|   | 1864 | 2.35 | 0.00033 | 0.020 | 15.8 |
|   | 1863 | 2.35 | 0.000331 | 0.021 | 15.8 |
|   | 1857 | 2.35 | 0.00033 | 0.020 | 15.6 |
|   | 1863 | 2.35 | 0.000331 | 0.025 | 15.8 |
|   | 1857 | 2.35 | 0.00033 | 0.021 | 15.6 |

Figure 33:
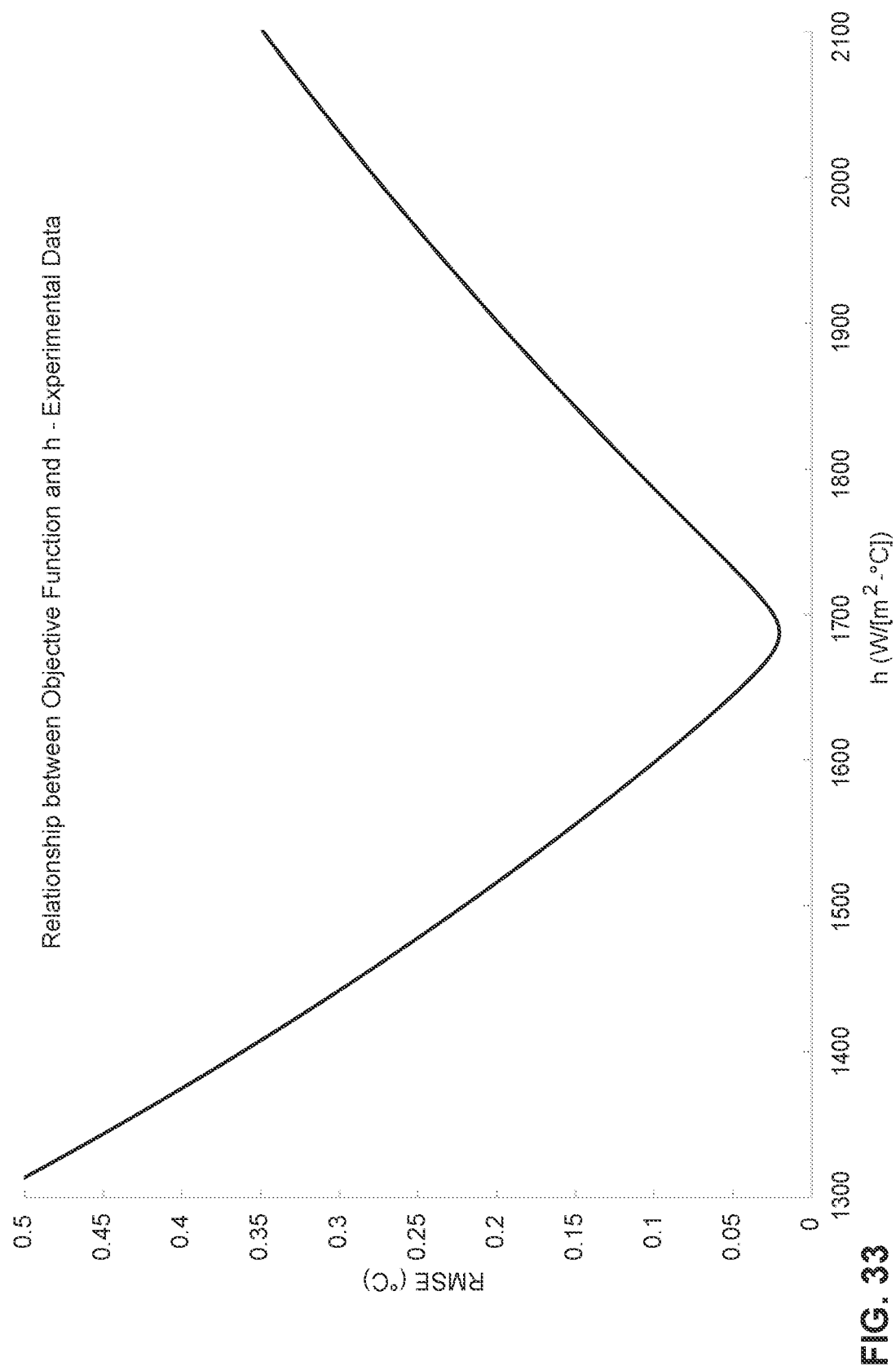
FIG. 33 is a graph showing the parameter estimation scheme's ability in determining the optimal convection coefficient (h) value when used with experimental data.

In order to demonstrate the ability of the parameter estimation scheme used in this data processing method in determining an optimal convection coefficient (h) value when used with experimental data, the relationship between the example objective function in Equation [68] (i.e., RMSE) and convection coefficient (h) for the 10 gal/man case is displayed in FIG. 33. The graph in FIG. 33 illustrates that the relationship has a global minimum at the convection coefficient (h) value of 1690 w/m²C. This corresponds to the estimated value for the 10 gal/min case, as documented in Table 4.

Figure 34:
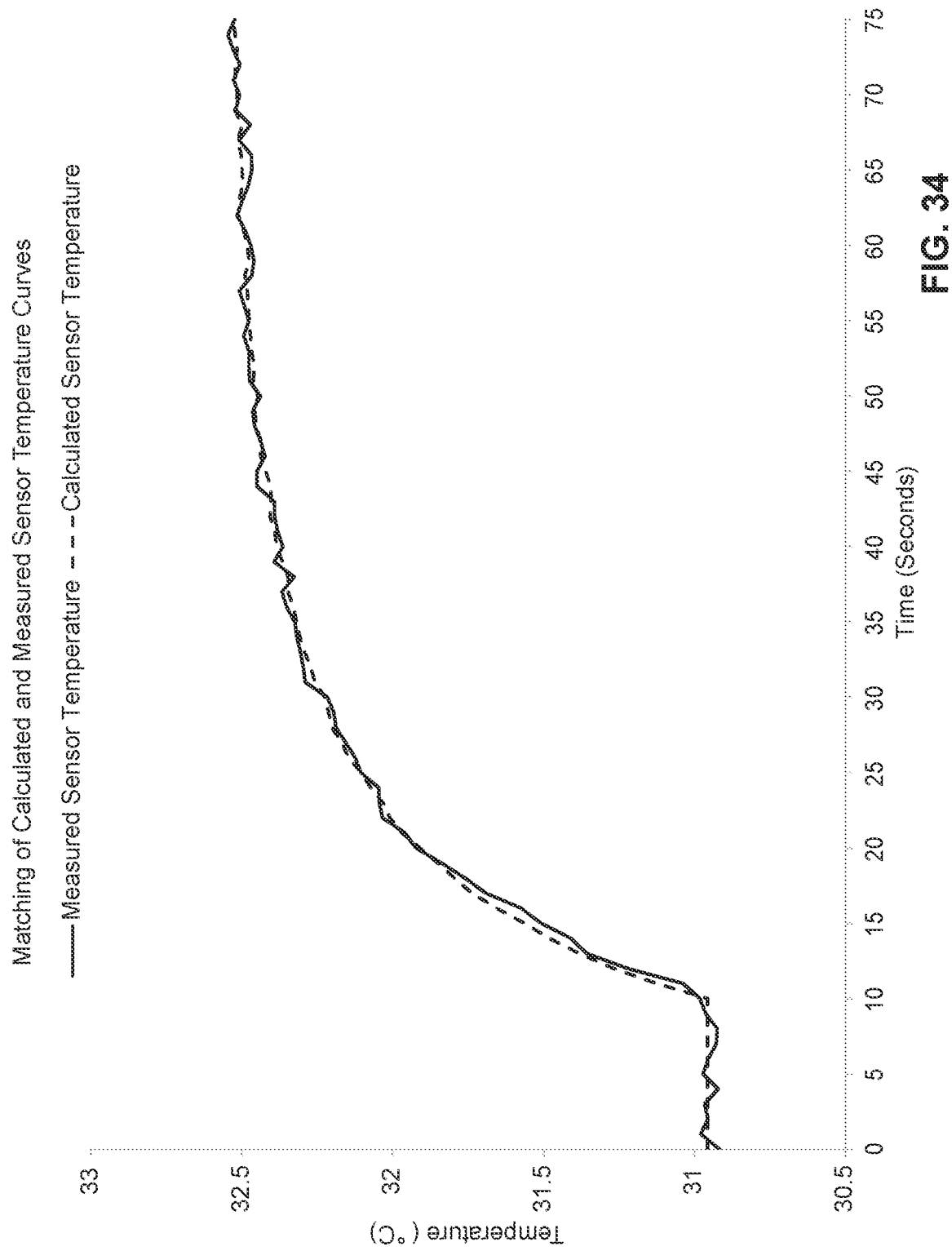
FIG. 34 is a graph showing an example of matching between a calculated (output) sensor temperature curve and a measured (input) sensor temperature for an example CHFT+ fluid flow in copper piping embodiment.
Figure 35:
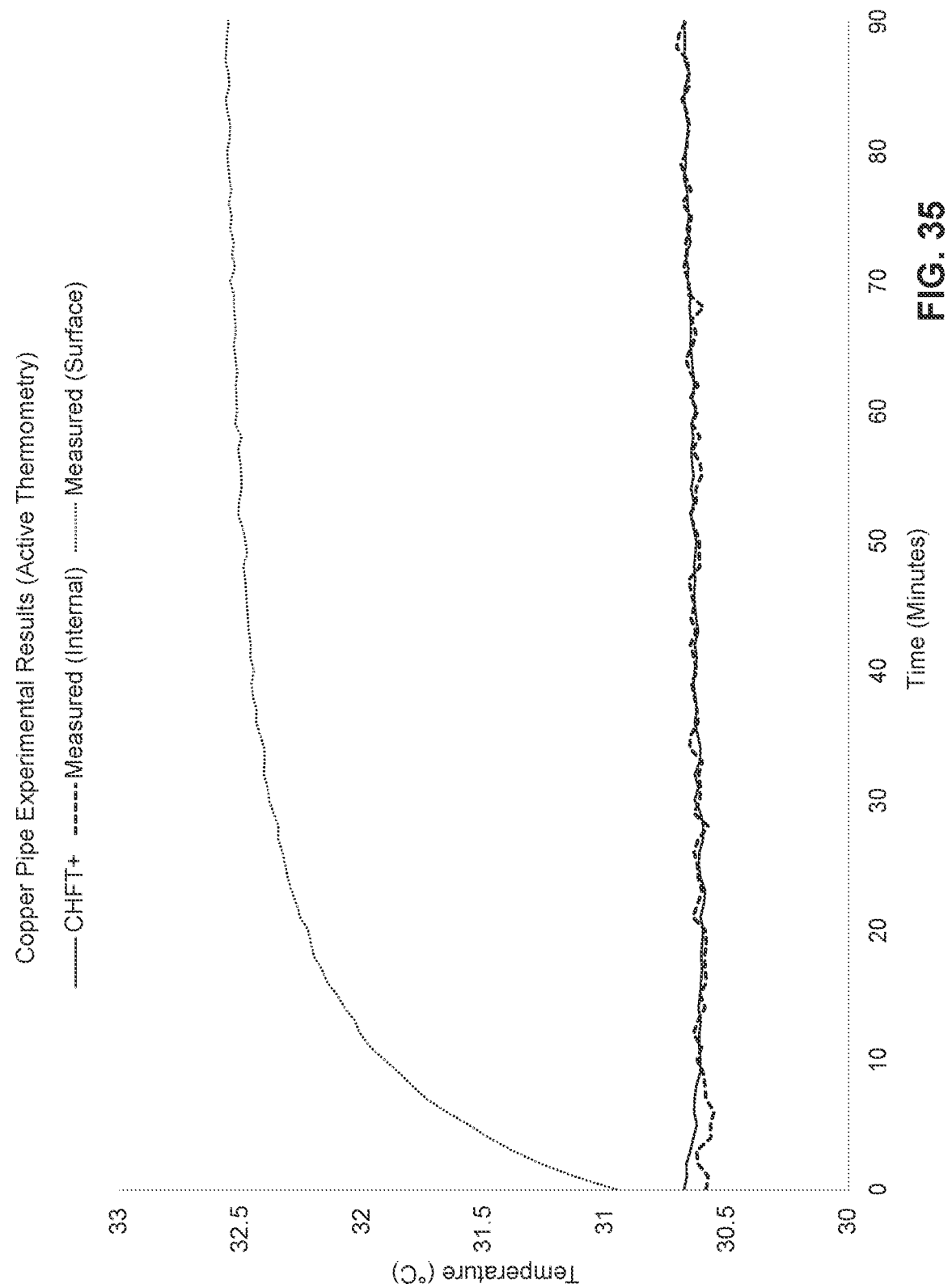
FIG. 35 is a graph showing results of an example CHFT+ embodiment (Active Thermometry) when used to measure the internal temperature of fluid flow within a copper pipe.

For the 10 gal/min case, FIG. 34 is a graph illustrating an example of matching between a calculated (output) sensor temperature curve and a measured (input) sensor temperature curve. The matching between the two temperature curves indicates that the internal parameter values (h, ρ, C, δ) and the thermal contact resistance ($R_C''$) value used to also be input as a predetermined value beforehand and still achieve similar results. In this example embodiment, whether the predetermined value for the thermal contact resistance ($R_C''$) is accurate or not, the flowrate ($\dot{v}$) results output may be accurate because the effect of any inaccuracies in the predetermined value of the thermal contact resistance ($R_C''$) is compensated by the subsequently developed correlation.

Another way to define and determine the thermal contact resistance ($R_C''$) is by using the overall definition of heat transfer coefficient, U, where:

$$\frac{1}{U} = \frac{1}{h} + R_C'' \qquad [71]$$

U (i.e., the total steady-state thermal resistance of the object) can be determined via a number of methods. One example method is to use the measurements made in steady-state conditions (e.g., before, after, or at the end of a thermal event) where, for example:

$$U = \frac{q''_{Sensor,END}}{T_{Sensor,END} - T_{Fluid,END}} \quad [72]$$

Thus, thermal contact resistance ($R_C''$) can be defined as:

$$R_C'' = \frac{T_{Sensor,END} - T_{Fluid,END}}{q''_{Sensor,END}} - \frac{1}{h} \quad [73]$$

and substituted instead of Equation [70]. In order to utilize Equation [73], the value of $T_{Fluid,END}$ typically needs to be determined. Some example methods of determining $T_{Fluid,END}$ (i.e., $T_{Fluid,m}$) are described below. In other example embodiments, $T_{Fluid,m}$ may be assumed or otherwise determined using, for example, surface mounted temperature sensors that may be insulated.

Another example method in determining U is to use measurements made in differing steady-state conditions (e.g., before, at the end of, or after a thermal event):

$$U = \frac{q''_{Sensor,END} - q''_{Sensor,0}}{T_{Sensor,END} - T_{Sensor,0}} \quad [74]$$

where $q''_{Sensor,END}$ and $T_{Sensor,END}$ represent heat flux and surface temperature measurements made in steady-state conditions at the end of a thermal event.

It should be noted that Equation [74] requires differing steady-state conditions which, for example, can be obtained by making measurements before and after a thermal event is generated via, for example, an external thermal device.

Using Equation [74] and Equation [71]:

$$R_C'' = \frac{T_{Sensor,END} - T_{Sensor,0}}{q''_{Sensor,END} - q''_{Sensor,0}} - \frac{1}{h} \quad [75]$$

A data processing method that includes a parameter estimation scheme and flowrate ($\dot{v}$) correlation may also be performed without differentiating between the convection heat transfer coefficient (h) and the thermal contact resistance ($R_C''$). Instead, the data processing method may be based on a thermal solution that is expressed using the overall heat transfer coefficient (U) as, for example, illustrated in Equation [76]:

$$T_{Calculated\_U,m} = T_{Sensor,0} + \sum_{j=1}^{m} \frac{(q''_{Sensor,j} - q''_{Sensor,j-1})}{U}(1 - e^{-\left(\frac{t_m - t_{j-1}}{\tau}\right)}) \quad [76]$$

where $T_{Calculated\_U,m}$ is the calculated (output) temperature curve found when using the overall heat transfer coefficient (U). Furthermore, the example objective function in this example embodiment may be:

$$RMSE = \sqrt{\frac{1}{M-1} \sum_{m=1}^{M-1} (T_{sensor,m} - T_{Calculated\_U,m})^2} \quad [77]$$

This method is especially useful when the estimated thermal contact resistance ($R_C''$) is minimal or otherwise estimated to be negligible.

Pipe Application—Real-Time Measurements Using Parameter Estimation Embodiment

In the example Pipe Application—Periodic Measurements using Parameter Estimation embodiment, data processing by the control circuitry starts after all measurements are made. Thus, in the experimental pipe testing above, measurements were output about every 75 seconds in a periodic manner. NITI sensor (e.g., CHFT+ or CHFT−) data may alternatively be processed in real-time to provide for real-time outputs of convection coefficient (h), core fluid temperature ($T_{Fluid}$), and/or thermal contact resistance ($R_C''$) between the NITI sensor and the pipe/conduit surfaces. As time goes on, more data points are added to the surface heat flux and surface temperature curves that are processed in real-time by a data processing method that includes a parameter estimation scheme and outputs values in less than 1 second.

Pipe Application—Real-Time Measurements without Parameter Estimation Embodiment

Equation [64] can be rearranged as:

$$\frac{1}{h} = \frac{T_{Pipe,m} - (T_{Sensor,0} - q''_{Sensor,0} \times R_C'')}{\sum_{j=1}^{m} \Delta q''_{Sensor,j} \times (1 - e^{-\left(\frac{t_m - t_{j-1}}{\tau}\right)})} \quad [78]$$

$$T_{Pipe,m} = T_{Sensor,m} - q''_{Sensor,m} \times R_C'' \quad [79]$$

Combining Equation [78] and Equation [79]:

$$h = \frac{\sum_{j=1}^{m} \Delta q''_{Sensor,j} \times (1 - e^{-\left(\frac{t_m - t_{j-1}}{\tau}\right)})}{(T_{Sensor,m} - q''_{Sensor,m} \times R_C'') - (T_{Sensor,0} - q''_{Sensor,0} \times R_C'')} \quad [80]$$

When the thermal contact resistance ($R_C''$) between the NITI sensor (e.g., CHFT+ or CHFT−) and the pipe/conduit surfaces is known, Equation [80] may be used for real time convection coefficient (h) measurement when a typical value for the thermal time constant ($\tau$) is input on the right side. As mentioned previously, the thermal time constant ($\tau$) is a function of convection coefficient (h). Thus, a typical value for convection coefficient (h) needs to be determined. In some example embodiments, for example when change in convection coefficient (h) is of interest, the quantity $T_{Sensor,0} - Q_{Sensor,0}'' \times R_C''$ may be assumed at one or more specified times. In other example embodiments, the quantity $T_{Sensor,0} - q_{Sensor,0}'' \times R_C''$ may be determined by, for example, using an additional temperature sensor; the output of which is indicative of pipe surface and/or core (i.e., internal) fluid temperature.

Although the calculated convection coefficient (h) value on the left side will not be exact, it will still suffice for accurate quantitative and/or qualitative measurements. Furthermore, for most accurate results, the typical value for convection coefficient (h), as relates to the thermal time constant ($\tau$), on the right side may be updated over time to reflect the most recent and/or accurate value calculated via Equation [80]. In other methods, the values for convection coefficient (h) on the right and left sides may be determined simultaneously, providing for accurate quantitative measurements. This may omit the need to input a typical convection coefficient (h) value on the right side. If the thermal contact resistance ($R_C''$) value is unknown, it can be determined (e.g., via the NITI procedures described above) or otherwise determined and accounted for. In some cases, the thermal contact resistance ($R_C''$) may be estimated to be negligible.

Inputting the determined convection coefficient (h) value from Equation [80] into a correlation equation (e.g., Equation [66]) results in corresponding flowrate ($\dot{v}$) values in real-time.

Furthermore, in steady-state conditions, Equation [80] reduces to:

$$h = \frac{q''_{Sensor,m} - q''_{Sensor,0}}{\left(T_{Sensor,m} - q''_{Sensor,m} \times R_C''\right) - \left(T_{Sensor,0} - q''_{Sensor,0} \times R_C''\right)} \quad [81]$$

Equation [80] no longer requires a typical thermal time constant ($\tau$) value on the right side. Steady-state conditions could be achieved in a variety of ways including a control circuitry that regulates the heat flux and/or temperature occurring at the surface via external thermal devices (e.g., heaters, coolers, etc.).

Similar rearrangement can be done for Equation [76] where the overall heat transfer coefficient (U) is utilized and yields:

$$U = \frac{\sum_{j=1}^{m} \Delta q''_{Sensor,j} \times (1 - e^{-\left(\frac{t_m - t_{j-1}}{\tau}\right)})}{T_{Sensor,m} - T_{Sensor,0}} \quad [82]$$

and in steady-state conditions:

$$U = \frac{q''_{Sensor,m} - q''_{Sensor,0}}{T_{Sensor,m} - T_{Sensor,0}} \quad [83]$$

Pipe Application—Duo NITI Sensor Embodiment

For an example DUO NITI sensor embodiment when using first and second parallel NITI sensor nodes (each node having a heat flux sensor-temperature sensor pair), two independent equations are formed:

$$T_{Sensor1,m} - q''_{Sensor1,m} \times R_{C1}'' = \quad [84]$$

$$T_{Fluid} + q''_{Sensor1,0} \times \frac{1}{h} + \sum_{j=1}^{m} \left(\frac{q''_{Sensor,j} - q''_{Sensor,j-1}}{h}\right)(1 - e^{-\left(\frac{t_m - t_{j-1}}{\tau}\right)})$$

$$T_{Sensor2,m} - q''_{Sensor2,m} \times R_{C1}'' = \quad [85]$$

$$T_{Fluid} + q''_{Sensor2,0} \times \frac{1}{h} + \sum_{j=1}^{m} \left(\frac{q''_{Sensor,j} - q''_{Sensor,j-1}}{h}\right)(1 - e^{-\left(\frac{t_m - t_{j-1}}{\tau}\right)})$$

Using an example differential based data processing method, Equation [84]-Equation [85] yields:

$$h = \frac{\begin{array}{c}(q''_{Sensor1,0} - q''_{Sensor2,0} + \Sigma_{j=1}^{m} \Delta q''_{Sensor1,j} \times \\ (1 - e^{-\left(\frac{t_m - t_{j-1}}{\tau}\right)}) - \sum_{i=1}^{m} \Delta q''_{Sensor2,j} \times (1 - e^{-\left(\frac{t_m - t_{j-1}}{\tau}\right)}))\end{array}}{\left(\left(T_{Sensor1,m} - q''_{Sensor1,m} \times R_{C1}''\right) - \left(T_{Sensor2,m} - q''_{Sensor2,m} \times R_{C2}''\right)\right)} \quad [86]$$

This transient equation is a result of the DUO NITI sensor configuration and allows for real time convection coefficient (h) measurement regardless of core fluid temperature ($T_{Fluid}$), when inputting a typical value for the thermal time constant ($\tau$), a function of convection coefficient (h), on the right side.

Although the calculated convection coefficient (h) value on the left side will not be exact, it will still suffice for accurate quantitative and/or qualitative measurements. Furthermore, for most accurate results, the typical value for convection coefficient (h), as relates to the thermal time constant ($\tau$), on the right side may be updated over time to reflect the most recent and/or accurate value calculated via Equation [86]. In other methods, the values for convection coefficient (h) on the right and left sides may be determined simultaneously, providing for accurate quantitative measurements. This may omit the need to input a typical convection coefficient (h) value on the right side.

Estimated values for the thermal contact resistances ($R_{C1}''$ and $R_{C2}''$) between each NITI sensor node (e.g., CHFT+ or CHFT−) and the pipe/conduit surfaces can be determined (e.g., via NITI procedures described above) or otherwise determined and accounted for. In some cases, the thermal contact resistances ($R_{C1}''$ and/or $R_{C2}''$) may be estimated to be negligible.

In steady-state conditions, Equation [86] reduces to:

$$h = \frac{(q''_{Sensor1,m} - q''_{Sensor2,m})}{\left(T_{Sensor1,m} - q''_{Sensor1,m} \times R_{C1}''\right) - \left(T_{Sensor2,m} - q''_{Sensor2,m} \times R_{C1}''\right)} \quad [87]$$

where a typical thermal time constant ($\tau$) value is no longer required on the right side. Steady-state conditions may be maintained in a variety of ways including a control circuitry that regulates the heat flux and/or temperature occurring at the surface of each sensor node via external thermal devices (e.g., heaters, coolers, etc.).

An example DUO CHFT+/− embodiment with one sensor node having a heater (CHFT+) and another sensor node without a heater (CHFT−) was tested on a ¾" (0.01905 m) inner diameter L type copper pipe with a 0.05" (0.00127 m) wall thickness with water flowing through it at different flowrates and temperatures. The DUO CHFT+/− arrangement was attached to the pipe surface and measurements were compared against an example CHFT+ embodiment as well as an inline flowmeter.

TABLE 5

Results of an example DUO CHFT+/−Embodiment

| Flowmeter Flowrate $\left(\frac{gal}{min}\right)$ | CHFT+ Flowrate $\left(\frac{gal}{min}\right)$ | DUO CHFT+/− Flowrate $\left(\frac{gal}{min}\right)$ |
|---|---|---|
| 4.0 | 3.8 | 3.9 |
| 7.0 | 7.3 | 7.5 |
| 10.0 | 9.8 | 10.4 |
| 13.0 | 13.1 | 12.9 |
| 16.0 | 15.9 | 15.6 |

Similar rearrangement can be done for Equation [76], where the overall heat transfer coefficient (U) is utilized, and yield:

$$h = \frac{(q''_{Sensor1,0} - q''_{Sensor2,0} + \sum_{j=1}^{m} \Delta q''_{Sensor1,j} \times (1 - e^{-\left(\frac{t_m - t_{j-1}}{\tau}\right)}) - \sum_{i=1}^{m} \Delta q''_{Sensor2,j} \times (1 - e^{-\left(\frac{t_m - t_{j-1}}{\tau}\right)}))}{T_{Sensor1,m} - T_{Sensor2,m}} \quad [88]$$

and at steady-state:

$$U = \frac{q''_{Sensor1,m} - q''_{Sensor2,m}}{T_{Sensor1,m} - T_{Sensor2,m}} \quad [89]$$

In addition to flowrate ($\dot{v}$), and core fluid temperature ($T_{Fluid}$), this NITI application (i.e., Pipe Parameter Determination) may be capable of determining the thermal energy being transferred by the flow inside of the pipe, a function of $\dot{v}$ and $T_{Fluid}$.

Corrosion/Fouling Detection Application

All of the example methods and example embodiments for Pipe Parameter Determination above determined h or U which is then input into a correlation function to determine flowrate (12). Monitoring the value of h or U independently may also be used to determine the occurrence of corrosion or fouling of a pipe/conduit over time. This is because the value of h or U should be consistent for a given amount of flowrate occurring in the pipe. As corrosion or fouling occurs, the values start to change and thus, corrosion or fouling can be detected. Monitoring the thermal time constant ($\tau$) of a pipe/conduit made, for example, of high thermal conductivity materials also yields similar capability. For example, in this example application, the thermal time constant ($\tau$) is a function of pipe/conduit properties including density ($\rho$), specific heat capacity (C), and wall thickness ($\delta$). The values of these properties are impacted by corrosion or fouling which consequently affect the thermal time constant ($\tau$) of the pipe/conduit.

Internal Temperature of Pipe or Conduit Measurement Application

Combining Equation [62] and Equation [63]:

$$T_{Pipe,m} = T_{Fluid} + \frac{q''_{Sensor,0}}{h} + \sum_{j=1}^{m}\left(\frac{q''_{Sensor,j} - q''_{Sensor,j-1}}{h}\right)(1 - e^{-\left(\frac{t_m - t_{j-1}}{\tau}\right)}) \quad [90]$$

Rewriting Equation [90] in terms of NITI sensor outputs and including effects of the thermal contact resistance ($R_C''$) between the NITI sensor and the pipe/conduit surfaces:

$$T_{Sensor,m} - q''_{Sensor,m} \times R_C'' = \quad [91]$$
$$T_{Fluid} + \frac{q''_{Sensor,0}}{h} + \sum_{j=1}^{m}\left(\frac{q''_{Sensor,j} - q''_{Sensor,j-1}}{h}\right)(1 - e^{-\left(\frac{t_m - t_{j-1}}{\tau}\right)})$$

Rearranging and realizing that $T_{Fluid}$ is dependent on values that change over time (measurement index (m)):

$$T_{Fluid,m} = T_{Sensor,m} - q''_{Sensor,m} \times R_C'' - \quad [92]$$
$$\frac{q''_{Sensor,0}}{h} - \sum_{j=1}^{m}\left(\frac{q''_{Sensor,j} - q''_{Sensor,j-1}}{h}\right)(1 - e^{-\left(\frac{t_m - t_{j-1}}{\tau}\right)})$$

Equation [92] is an example equation for core fluid temperature ($T_{Fluid,m}$) measurement in pipes or conduits with high thermal conductivity (e.g., copper) and is used in the following example embodiments below. For some of these example embodiments, values of convection coefficient (h), estimated thermal contact resistance ($R_C''$) between the NITI sensor and the pipe/conduit surfaces, and/or thermal time constant ($\tau$) need to be determined. This can be done by, for example, determining these values (e.g., via the CHFT+ or CHFT− methods described prior) or by inputting predetermined values (e.g., values from a textbook).

Similar example embodiments to those below can be used with Equation [76], where the overall heat transfer coefficient (U) is utilized instead of a combination of convection coefficient (h) and thermal contact resistance ($R_C''$) between the NITI sensor and the pipe/conduit surfaces.

Pipe Internal Temperature—CHFT+(Active Thermometry) Embodiment

A CHFT+ embodiment uses an integrated external thermal device such as a heater to create a thermal event (i.e., heat transfer) that can be used to perform NITI. For core fluid temperature ($T_{Fluid,m}$) measurement, the heater may operate in any manner (steady, periodic, cycled, etc.) and, in this example, Equation [92] would output the core fluid temperature ($T_{Fluid,m}$) accurately and in real-time when values for convection coefficient (h), thermal time constant ($\tau$), and estimated thermal contact resistance ($R_C''$) are input on the right side. These values could be determined by, for example, using a data processing method (e.g., that includes a parameter estimation scheme) or otherwise determined and accounted for. In some cases, the thermal contact resistance ($R_C''$) may be estimated to be negligible. Although not required, it may be beneficial to cover the CHFT+ with insulating material to prevent erroneous signals from external stimuli such as ambient changes, contact, etc.

Table 6 provides experimental results from an example CHFT+ embodiment (with integrated heater) when used to measure the core fluid temperature ($T_{Fluid,m}$) of a ¾" (0.01905 m) inner diameter L type copper pipe with a 0.05" (0.00127 m) wall thickness at different flowrates where the measurements of core fluid temperature measurement ($T_{Fluid,m}$) have been averaged over time:

TABLE 6

Example CHFT+ Embodiment Results for Internal Pipe Temperature

| Flowrate $\left(\frac{gal}{min}\right)$ | CHFT+ Output (° C.) | $T_{Fluid}$ Measured (° C.) | $\|\Delta T\|$ (° C.) |
|---|---|---|---|
| 1 | 24.76 | 24.86 | 0.10 |
|   | 24.98 | 25.09 | 0.11 |
|   | 25.18 | 25.30 | 0.12 |
|   | 25.42 | 25.52 | 0.10 |
|   | 25.62 | 25.73 | 0.11 |
|   | 25.85 | 25.95 | 0.10 |
| 4 | 22.28 | 22.41 | 0.13 |
|   | 22.45 | 22.58 | 0.13 |
|   | 22.75 | 22.86 | 0.11 |
|   | 22.95 | 23.10 | 0.15 |
|   | 23.25 | 23.31 | 0.06 |
|   | 23.70 | 23.84 | 0.14 |
| 7 | 22.65 | 22.68 | 0.03 |
|   | 22.86 | 22.91 | 0.05 |
|   | 23.14 | 23.19 | 0.05 |
|   | 23.40 | 23.46 | 0.06 |
|   | 23.77 | 23.85 | 0.08 |
|   | 24.12 | 24.17 | 0.05 |
| 10 | 25.46 | 25.58 | 0.12 |
|   | 25.66 | 25.76 | 0.10 |
|   | 29.24 | 29.27 | 0.03 |
|   | 29.63 | 29.69 | 0.06 |
|   | 29.89 | 29.86 | 0.03 |
|   | 30.34 | 30.32 | 0.02 |
| 13 | 25.47 | 25.61 | 0.14 |
|   | 25.65 | 25.77 | 0.12 |
|   | 25.86 | 25.99 | 0.13 |
|   | 26.04 | 26.13 | 0.09 |
|   | 26.25 | 26.40 | 0.15 |
|   | 26.51 | 26.66 | 0.15 |
| 16 | 26.24 | 26.42 | 0.18 |
|   | 26.38 | 26.49 | 0.11 |
|   | 26.51 | 26.60 | 0.09 |
|   | 26.68 | 26.79 | 0.11 |
|   | 26.83 | 27.01 | 0.18 |
|   | 27.02 | 27.19 | 0.17 |

FIG. 354 is a graph showing results of an example CHFT+ embodiment (with integrated and controlled heater) when used to measure the core fluid temperature ($T_{Fluid,m}$) of a ¾" (0.01905 m) inner diameter L type copper pipe with a 0.05" (0.00127 m) wall thickness undergoing fluid flow at 15 gal/min. In this graph it is shown that the example CHFT+ embodiment is capable of determining the core fluid temperature ($T_{Fluid,m}$) of a pipe regardless of surface temperature conditions. Specifically, in this example, the surface temperature increases with time as a result of the integrated heater being turned on. Regardless of this consistent increase in surface temperature over time, the example CHFT+ embodiment measures the core fluid temperature ($T_{Fluid,m}$) within the copper pipe with close agreement to an internal probe placed inside the pipe and within the pipe flow.

Pipe Internal Temperature—CHFT− (Passive Thermometry) Embodiment

A CHFT− embodiment uses external thermal events such as pipe heat dissipation to the environment to perform NITI. When subject to an external thermal event, Equation [92], for example, would output the core fluid temperature ($T_{Fluid,m}$) accurately and in real-time when values for convection coefficient (h), thermal time constant (τ), and estimated thermal contact resistance ($R_C''$) are input on the right side. These values could be determined by, for example, using a data processing method (e.g., that includes a parameter estimation scheme) or otherwise determined and accounted for. In some cases, the thermal contact resistance ($R_C''$) may be estimated to be negligible. Although not required, it may be beneficial to cover the CHFT− with insulating material to prevent erroneous signals from external stimuli such as ambient changes, contact, etc.

Pipe Internal Temperature—CHFT+ (Periodic Measurement) Embodiment

In addition to the example real-time methods and example embodiments for Internal Temperature of Pipe or Conduit Measurement above, a NITI sensor can be used to make periodic measures of core fluid temperature ($T_{Fluid}$) when operating in differing steady-state conditions. For example, steady-state measurements prior to a thermal event ($T_{Sensor,0}$, $q_{Sensor,0}''$) can be compared with steady-state measurements during, after, or at the end of a thermal event ($T_{Sensor,END}$, $q_{Sensor,END}''$) in order to determine core fluid temperature ($T_{Fluid}$) using:

$$T_{Fluid} = \frac{T_{Sensor,0} \times q_{Sensor,END}'' - T_{Sensor,END} \times q_{Sensor,0}''}{q_{Sensor,END}'' - q_{Sensor,0}''} \quad [93]$$

CHFT+ and/or CHFT− example embodiments can both be subject to differing steady-state conditions over time. However, CHFT+ example embodiments are preferred due to the increased operational control of the one or more thermal event devices that may be used to create differing steady-state conditions.

Pipe Internal Temperature—CHFT+(Zero Heat-Flux Thermometry) Embodiment

Using control circuitry, an example CHFT+ embodiment may be used to create a zero heat-flux environment where no heat transfer occurs between the pipe and the sensor surfaces, i.e., where no heat enters or leaves the pipe as measured by the heat flux sensor (minimal voltage output, i.e., "zero").

In steady-state conditions, a zero heat-flux environment simplifies Equation [92] to:

$$T_{Fluid,m} = T_{Sensor,m} \quad [94]$$

where the measured sensor temperature ($T_{Sensor,m}$) is equivalent to the core fluid temperature ($T_{Fluid,m}$). The advantage of this method is the independence of core fluid temperature ($T_{Fluid,m}$) measurement from the internal parameter values (e.g., convection coefficient (h), thermal time constant (τ), etc.) and thermal contact resistance ($R_C''$) once a steady-state zero heat-flux environment is obtained. Until a steady-state zero heat-flux environment is obtained, other embodiments, such as the Active Thermometry embodiment for Internal Temperature of Pipe or Conduit Measurement, can be utilized to make accurate measurements of core fluid temperature ($T_{Fluid,m}$). The amount of time required to achieve such steady-state conditions, as determined by the measured sensor temperature ($T_{Sensor,m}$) output, varies depending on the example embodiment used and is a common limitation of existing Zero Heat-Flux technologies that do not utilize NITI technology. Until a steady-state zero heat-flux environment is obtained, example Zero Heat-Flux Thermometry embodiments may utilize other example NITI embodiments, such as an example Active Thermometry embodiment for Pipe Internal Temperature Measurement, to make accurate measurements of core fluid temperature ($T_{Fluid,m}$).

Pipe Internal Temperature—Duo NITI (Dual Thermometry) Embodiment

For an example DUO NITI sensor embodiment when using first and second parallel NITI sensor nodes (each node having a heat flux sensor-temperature sensor pair), two independent equations are formed when placed on a pipe/conduit made of material with high thermal conductivity:

$$\left(T_{Sensor1,m} - q''_{Sensor1,m} \times R''_{C1}\right) - T_{Fluid,m} = \frac{1}{h}\left(q''_{Sensor1,0} + \sum_{j=1}^{m} \Delta q''_{Sensor1,j} \times (1 - e^{-\left(\frac{t_m - t_{j-1}}{\tau}\right)})\right) \quad [95]$$

$$\left(T_{Sensor2,m} - q''_{Sensor2,m} \times R''_{C2}\right) - T_{Fluid,m} = \frac{1}{h}\left(q''_{Sensor2,0} + \sum_{j=1}^{m} \Delta q''_{Sensor1,j} \times (1 - e^{-\left(\frac{t_m - t_{j-1}}{\tau}\right)})\right) \quad [96]$$

Using a quotient based data processing method, Equation [95]/Equation [96] yields:

$$\frac{\left(T_{Sensor1,m} - q''_{Sensor1,m} \times R''_{C1}\right) - T_{Fluid \cdot m}}{\left(T_{Sensor2,m} - q''_{Sensor2,m} \times R''_{C2}\right) - T_{Fluid \cdot m}} = \frac{\left(q''_{Sensor1,0} + \sum_{j=1}^{m} \Delta q''_{Sensor1,j} \times (1 - e^{-\left(\frac{t_m - t_{j-1}}{\tau}\right)})\right)}{\left(q''_{Sensor2,0} + \sum_{j=1}^{m} \Delta q''_{Sensor2,j} \times (1 - e^{-\left(\frac{t_m - t_{j-1}}{\tau}\right)})\right)} \quad [97]$$

Rearranging:

$$T_{Fluid \cdot m} = \frac{\left(T_{Sensor2,m} - q''_{Sensor2,m} \times (R''_{C2})\right) \times \left(q''_{Sensor1,0} + \sum_{j=1}^{m} \Delta q''_{Sensor1,j} \times (1 - e^{-\left(\frac{t_m - t_{j-1}}{\tau}\right)})\right) - \left(T_{Sensor1,m} - q''_{Sensor1,m} \times R''_{C1}\right) \times \left(q''_{Sensor2,0} + \sum_{j=1}^{m} \Delta q''_{Sensor2,j} \times (1 - e^{-\left(\frac{t_m - t_{j-1}}{\tau}\right)})\right)}{\left(q''_{Sensor1,0} + \sum_{j=1}^{m} \Delta q''_{Sensor1,j} \times (1 - e^{-\left(\frac{t_m - t_{j-1}}{\tau}\right)})\right) - \left(q''_{Sensor2,0} + \sum_{j=1}^{m} \Delta q''_{Sensor2,j} \times (1 - e^{-\left(\frac{t_m - t_{j-1}}{\tau}\right)})\right)} \quad [98]$$

This transient equation is a result of the DUO NITI configuration and allows for real time core fluid temperature ($T_{Fluid,m}$) measurement when inputting typical values for convection coefficient (h) and thermal time constant ($\tau$) on the right side.

Estimated values for the thermal contact resistances ($R_{C1}''$ and $R_{C2}''$) between each NITI sensor node (e.g., CHFT+ or CHFT−) and the pipe/conduit surfaces can be determined (e.g., via NITI procedures described above) or otherwise determined and accounted for. In some cases, the thermal contact resistances ($R_{C1}''$ and/or $R_{C2}''$) may be estimated to be negligible.

In steady-state conditions, and where $R_{C1}'' \approx R_{C1}'' \approx R_{C2}''$ or $R_{C1}''$ and $R_{C2}''$ are estimated to be negligible, Equation [98] reduces to:

$$T_{Fluid \cdot m} = \frac{T_{Sensor2,m} \times q''_{Sensor 1,m} - T_{Sensor1,m} \times q''_{Sensor2,m}}{q''_{Sensor1,m} - q''_{Sensor2,m}} \quad [99]$$

where typical values for convection coefficient (h) and thermal time constant ($\tau$) are no longer required on the right side. This implies that, when in steady-state conditions, Equation [99] can be used for pipes or conduits regardless of the pipe/conduit material, wall thickness, etc. Steady-state conditions could be achieved in a variety of ways including a control circuitry that regulates the heat flux and/or temperature occurring at the tissue surface via external thermal devices (e.g., heaters, coolers, etc.).

Figure 36:
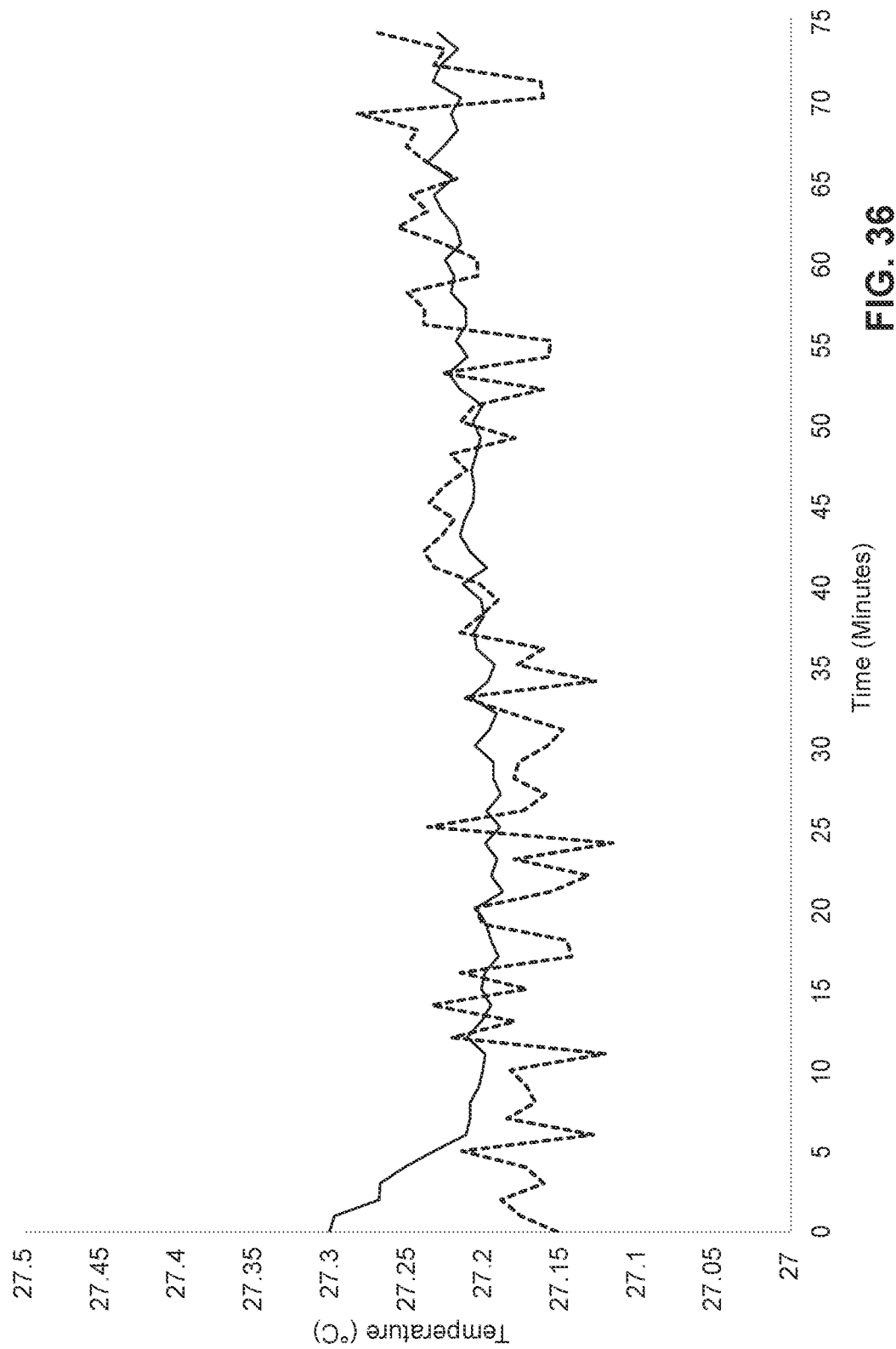
FIG. 36 is a graph showing results of an example DUO CHFT+/− embodiment (one sensor node with heater and one sensor node without) when used to measure the internal temperature of fluid flow within a copper pipe.

FIG. 36 is a graph showing results of an example DUO CHFT+/− embodiment (one sensor node with heater and one sensor node without) when used to measure the internal temperature of a ¾" (0.01905 m) inner diameter L type copper pipe with a 0.05" (0.00127 m) wall thickness undergoing fluid flow at 15 gal/min. In this example, both sensor nodes were covered with insulation in order to prevent sporadic heat transfer and temperature signals from impacting the quality of measurement. This example was conducted in both steady-state and transient conditions. As shown in the graph, there is close agreement between the example DUO CHFT+/− embodiment and an internal probe (placed inside the pipe and within the pipe flow).

Figure 37:
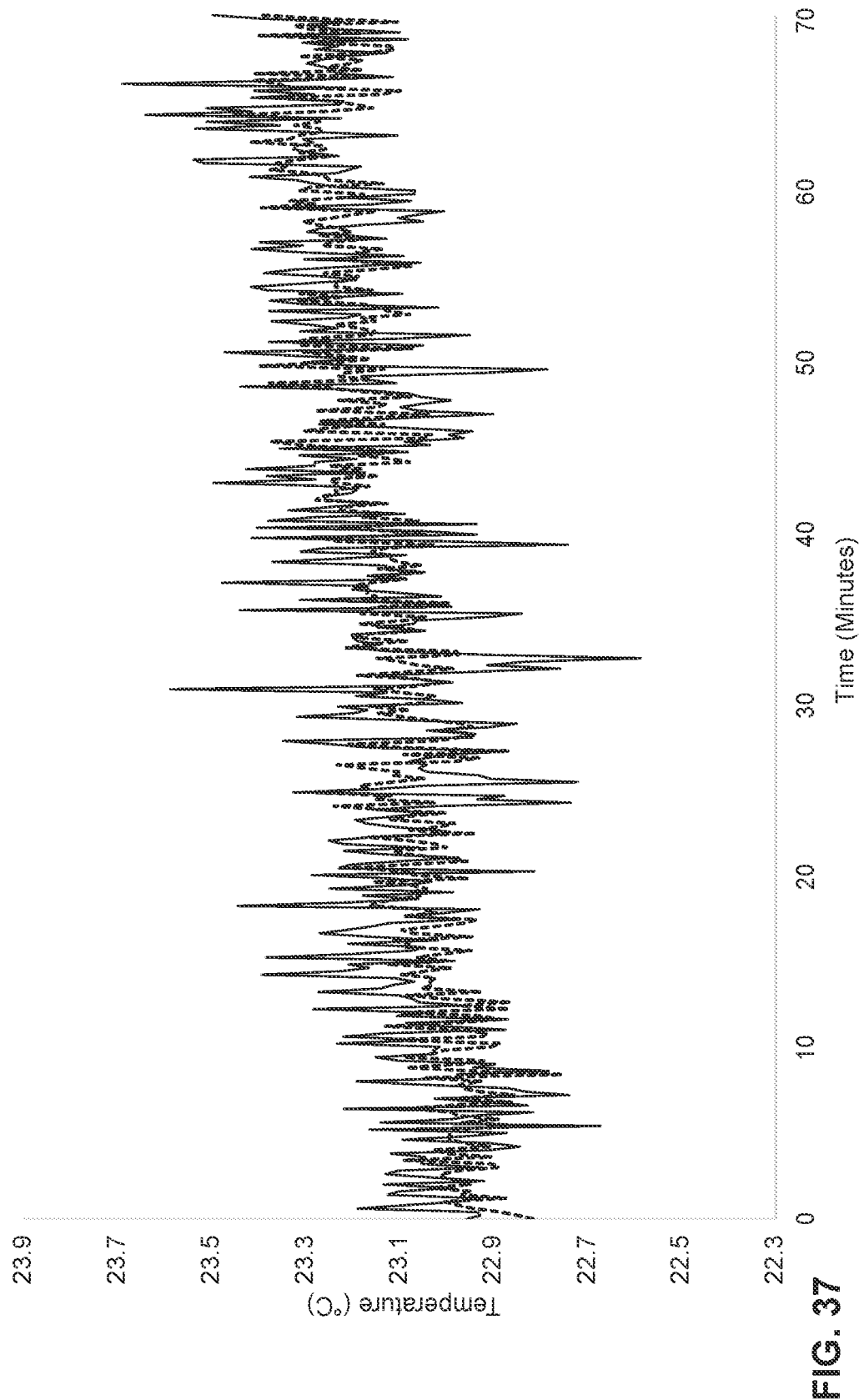
FIG. 37 is a graph showing results of an example DUO CHFT+/− embodiment (one sensor node with heater and one sensor node without) when used to measure the internal temperature of fluid flow within a CPVC pipe.

FIG. 37 is a graph showing results of an example DUO CHFT+/− embodiment (one sensor node with heater and one sensor node without) when used to measure the internal temperature of a 1.939" (0.0492506 m) inner diameter Schedule 80 CPVC pipe with a 0.218" (0.0055372 m) wall thickness undergoing fluid flow at 50 gal/min. In min this example, both sensor nodes were not covered with insulation. This example was conducted in steady-state conditions where the internal parameters of the pipe are not required to make accurate measurements. As shown in the graph, there is close agreement between the example DUO CHFT+/− embodiment and an internal probe (placed inside the pipe and within the pipe flow). There are, however, more sporadic measurements as a result of not covering the sensors nodes with insulation.

Although various example embodiments have been shown and described in detail, the claims are not limited to any particular embodiment or example. Moreover, example embodiments above use thermal signals (e.g., heat transfer and temperature signals) combined with analytical solutions that are based on thermal mathematical models to determine one or more internal properties of an object. Other example embodiments may utilize other methods including, but not limited to, empirical methods, machine learning methods (e.g., neural networks), regression based methods, artificial intelligence based methods, moving average based methods, etc. in order to determine one or more internal properties of an object based on thermal signals measured at the object surface.

In other example embodiments, the output of other non-NITI based devices may be used in conjunction with NITI techniques to determine one or more internal properties of the internal region of an object. For example, the output of an internal temperature probe within a pipe may be used with a surface mounted NITI sensor to determine flowrate within the pipe.

In the present application, the words "configured to . . . " are used to mean that an element of an apparatus has a configuration able to carry out the defined operation. A "configuration" may also refer to an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

None of the above description should be read as implying that any particular member, step, range, or function is essential. All structural and functional equivalents to the members of the above-described embodiments that are known to those of ordinary skill in the art are incorporated herein by reference and are intended to be encompassed. Furthermore, no embodiment, feature, component, or step in this specification is intended to be dedicated to the public.

Although illustrative embodiments have been described in detail herein with reference to the accompanying drawings, it is to be understood that the invention is not limited to those precise embodiments, and that various changes and modifications can be effected therein by one skilled in the art without departing from the scope of the appended claims.

The invention claimed is:

1. An apparatus for non-invasively sensing a temperature of a fluid contained within a pipe or tank object, the apparatus comprising:
    a temperature sensor having one or more output terminals;
    a heat-flux sensor having one or more output terminals; and circuitry coupled to the output terminals and adapted to:
    receive a temperature signal from the temperature sensor;
    receive a heat-flux signal from the heat-flux sensor, wherein the heat-flux signal indicates thermal energy leaving or entering the pipe or tank object; and
    determine the temperature of the fluid contained within the pipe or tank object at one or more specified times based on at least the temperature signal and the heat-flux signal;
    wherein the apparatus is adapted to be placed on or near a surface of the pipe or tank object.

2. The apparatus of claim 1, wherein the circuitry is adapted to determine a measure of heat transfer leaving or entering the surface based on the heat-flux signal.

3. The apparatus of claim 1, wherein a thermally conductive material is placed between the surface and the apparatus.

4. The apparatus of claim 1, wherein the circuitry is adapted to determine the fluid temperature using one or more thermal mathematical models.

5. The apparatus of claim 1, further comprising thermal insulation, wherein the heat-flux sensor and the temperature sensor are both disposed between the surface of the object and the thermal insulation.

6. The apparatus of claim 1, wherein the temperature sensor is an RTD temperature sensor.

7. The apparatus of claim 1, wherein the heat-flux sensor is a thin-film thermopile heat-flux sensor.

8. The apparatus of claim 1, wherein the heat-flux sensor is a thin-film heat-flux sensor.

9. The apparatus of claim 1, wherein the heat-flux sensor is a flexible heat-flux sensor.

10. The apparatus of claim 1, wherein the heat-flux sensor is next to the temperature sensor.

11. The apparatus of claim 1, wherein the circuitry is adapted to determine the temperature of the fluid based on at least the temperature signal, the heat-flux signal, and one or more indicative quantities for one or more of the following parameters:
    a wall thickness of the object,
    a radius of the object,
    a diameter of the object, and
    a thermal conductivity of the object.

12. The apparatus of claim 1, wherein the circuitry is adapted to generate information for an output indicating the fluid temperature.

13. The apparatus of claim 12, wherein the circuitry is adapted to communicate the information using wired or wireless communication.

14. The apparatus of claim 12, wherein the circuitry is adapted to output the fluid temperature to a display using wired or wireless communication.

15. The apparatus of claim 1, wherein the circuitry is adapted to determine the temperature of the fluid based on at least the temperature signal, the heat-flux signal, and one or more indicative quantities for one or more of the following parameters:
    a wall thickness of the object,
    a radius of the object,
    a diameter of the object,
    a cross-sectional measure of the object,
    a thermal conductivity of the object,
    a density of the object,
    a heat capacity of the object,
    a heat transfer coefficient of the fluid,
    a flowrat eof the fluid,
    a flow velocity of the fluid,
    a thermal conductivity of the fluid,
    a density of the fluid,
    a heat capacity of the fluid, and
    one or more effects associated with a thermal contact conductance between the apparatus and the surface.

16. The apparatus of claim 15, wherein the circuitry is adapted to generate information for an output indicating one or more of the parameters.

17. The apparatus of claim 15, wherein the circuitry is adapted to receive information for one or more of the indicative quantities based on data input to the circuitry.

18. The apparatus of claim 15, wherein the circuitry is adapted to determine the fluid temperature using one or more thermal mathematical models.

19. A system for non-invasively sensing a temperature of a fluid contained within a pipe or tank object, the system comprising:
    a non-invasive sensor adapted to be placed on or near a surface of the pipe or tank object including:
    a temperature sensor having one or more output terminals;
    a heat-flux sensor having one or more output terminals; and network or cloud connected circuitry coupled to the output terminals and adapted to:
    receive a temperature signal from the temperature sensor;
    receive a heat-flux signal from the heat-flux sensor, wherein the heat-flux signal indicates thermal energy leaving or entering the pipe or tank object;
    determine the temperature of the fluid contained within the pipe or tank object at one or more specified times based on at least the temperature signal and the heat-flux signal; and
    generate information indicating the fluid temperature.

20. The system of claim 19, wherein the circuitry includes wired or wireless communication.

21. The system of claim 19, wherein the circuitry includes a display to output the information.

22. The system of claim 19, wherein the system is used for one or more of remote monitoring, data logging, data display, analytics, or diagnostics.

23. The system of claim 19, wherein the circuitry is adapted to determine a measure of heat transfer leaving or entering the surface based on the heat-flux signal.

24. The system of claim 19, wherein a thermally conductive material is placed between the surface and the non-invasive sensor.

25. The system of claim 19, wherein the circuitry is adapted to determine the fluid temperature using one or more thermal mathematical models.

26. The system of claim 19, further comprising thermal insulation, wherein the non-invasive sensor is disposed between the surface and the thermal insulation.

27. The system of claim 19, wherein the temperature sensor is an RTD temperature sensor.

28. The system of claim 19, wherein the heat-flux sensor is a thin-film thermopile heat-flux sensor.

29. The system of claim 19, wherein the heat-flux sensor is a thin-film heat-flux sensor.

30. The system of claim 19, wherein the heat-flux sensor is a flexible heat-flux sensor.

31. The system of claim 19, wherein the heat-flux sensor is next to the temperature sensor.

32. The system of claim 19, wherein the circuitry is adapted to determine the temperature of the fluid based on at least the temperature signal, the heat-flux signal, and one or more indicative quantities for one or more of the following parameters:
 a wall thickness of the object,
 a radius of the object,
 a diameter of the object,
 a cross-sectional measure of the object,
 a thermal conductivity of the object,
 a density of the object,
 a heat capacity of the object,
 a heat transfer coefficient of the fluid,
 a flowrate of the fluid,
 a flow velocity of the fluid,
 a thermal conductivity of the fluid,
 a density of the fluid,
 a heat capacity of the fluid, and
 one or more effects associated with a thermal contact conductance between the non-invasive sensor and the surface.

33. The system of claim 32, wherein the circuitry is adapted to generate information for an output indicating one or more of the parameters.

34. The system of claim 32, wherein the circuitry is adapted to receive information for one or more of the indicative quantities based on data input to the circuitry.

35. An internet-of-things system, the system comprising:
 a non-invasive sensor adapted to be placed on or near a surface of a pipe or tank object containing fluid, the non-invasive sensor including:
  a temperature sensor having one or more output terminals;
  a heat-flux sensor having one or more output terminals; and circuitry coupled to the output terminals and adapted to:
   receive a temperature signal from the temperature sensor;
   receive a heat-flux signal from the heat-flux sensor, wherein the heat-flux signal indicates thermal energy leaving or entering the pipe or tank object;
   determine a temperature of the fluid contained within the pipe or tank object at one or more specified times based on at least the temperature signal and the heat-flux signal; and
   generate information indicating the fluid temperature.

36. The system of claim 35, wherein the circuitry includes wired or wireless communication.

37. The system of claim 35, wherein the circuitry includes a display to output the information.

38. The system of claim 35, wherein the system is used for one or more of remote monitoring, data logging, data display, analytics, or diagnostics.

39. The system of claim 35, wherein the circuitry is adapted to determine a measure of heat transfer leaving or entering the surface based on the heat-flux signal.

40. The system of claim 35, wherein a thermally conductive material is placed between the surface and the non-invasive sensor.

41. The system of claim 35, wherein the circuitry is adapted to determine the fluid temperature using one or more thermal mathematical models.

42. The system of claim 35, further comprising thermal insulation, wherein the non-invasive sensor is disposed between the surface and the thermal insulation.

43. The system of claim 35, wherein the temperature sensor is an RTD temperature sensor.

44. The system of claim 35, wherein the heat-flux sensor is a thin-film thermopile heat-flux sensor.

45. The system of claim 35, wherein the heat-flux sensor is a thin-film heat-flux sensor.

46. The system of claim 35, wherein the heat-flux sensor is a flexible heat-flux sensor.

47. The system of claim 35, wherein the heat-flux sensor is next to the temperature sensor.

48. The system of claim 35, wherein the circuitry is adapted to determine the temperature of the fluid based on at least the temperature signal, the heat-flux signal, and one or more indicative quantities for one or more of the following parameters:
 a wall thickness of the object,
 a radius of the object,
 a diameter of the object,
 a cross-sectional measure of the object,
 a thermal conductivity of the object,
 a density of the object,
 a heat capacity of the object,
 a heat transfer coefficient of the fluid,
 a flowrate of the fluid,
 a flow velocity of the fluid,
 a thermal conductivity of the fluid,
 a density of the fluid,
 a heat capacity of the fluid, and
 one or more effects associated with a thermal contact conductance between the non-invasive sensor and the surface.

49. The system of claim 48, wherein the circuitry is adapted to generate information for an output indicating one or more of the parameters.

50. The system of claim 48, wherein the circuitry is adapted to receive information for one or more of the indicative quantities based on data input to the circuitry.

51. A non-invasive sensor adapted to be placed on or near a surface of a pipe or tank object containing fluid, the non-invasive sensor comprising:
- a heat-flux sensor having one or more output terminals and
- a temperature sensor having one or more output terminals,
- wherein the heat-flux sensor and the temperature sensor is are used to determine a temperature of the fluid contained within the pipe or tank object under conditions where heat transfer is occurring through the non-invasive sensor.

52. The non-invasive sensor of claim 51, wherein the temperature sensor is an RTD temperature sensor.

53. The non-invasive sensor of claim 52, wherein the heat-flux sensor is a thin-film heat-flux sensor.

54. The non-invasive sensor of claim 52, wherein the heat-flux sensor is a thin-film thermopile heat-flux sensor.

55. The non-invasive sensor of claim 54, wherein the heat-flux sensor is a flexible heat-flux sensor.

56. The non-invasive sensor of claim 55, wherein the heat-flux sensor is next to the temperature sensor.

57. The non-invasive sensor of claim 55, wherein the non-invasive sensor is used in a system for one or more of internet of things, remote monitoring, data logging, data display, analytics, or diagnostics.

58. The non-invasive sensor of claim 55, further comprising thermal insulation, wherein the non-invasive sensor is disposed between the surface and the thermal insulation.

59. The non-invasive sensor of claim 55, wherein the heat-flux sensor and the temperature sensor are affixed to a metal object.

60. The non-invasive sensor of claim 59, wherein the non-invasive sensor is adapted to ensure that a mismatch does not exist between a heat-flux signal from the heat-flux sensor and a temperature signal from the temperature sensor.

* * * * *

UNITED STATES PATENT AND TRADEMARK OFFICE
CERTIFICATE OF CORRECTION

| | | |
|---|---|---|
| PATENT NO. | : 12,313,477 B2 | Page 1 of 1 |
| APPLICATION NO. | : 18/132508 | |
| DATED | : May 27, 2025 | |
| INVENTOR(S) | : Ali R. Roghanizad | |

It is certified that error appears in the above-identified patent and that said Letters Patent is hereby corrected as shown below:

In the Claims

Column 68, Line 32, Claim 15 "flowrat eof" should read -- flowrate of --

Column 71, Line 7, Claim 51 delete "is" following "temperature sensor"

Signed and Sealed this
Eighteenth Day of November, 2025

John A. Squires
*Director of the United States Patent and Trademark Office*